United States Patent
Langer et al.

(10) Patent No.: US 12,377,153 B2
(45) Date of Patent: Aug. 5, 2025

(54) POLY(BETA-THIOESTER) POLYMERS AND POLYMERIC NANOPARTICLES

(71) Applicants: MASSACHUSETTS INSTITUTE OF TECHNOLOGY, Cambridge, MA (US); THE BRIGHAM AND WOMEN'S HOSPITAL, INC., Boston, MA (US)

(72) Inventors: Robert Langer, Newton, MA (US); Carlo Traverso, Newton, MA (US); Ameya Kirtane, Somerville, MA (US); Daniel Reker, Somerville, MA (US); Lewis Scott Jones, Cambridge, MA (US); Hyunjoon Kim, Cambridge, MA (US); Netra Rajesh, Cambridge, MA (US)

(73) Assignees: MASSACHUSETTS INSTITUTE OF TECHNOLOGY, Cambridge, MA (US); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 644 days.

(21) Appl. No.: 17/597,974

(22) PCT Filed: Jul. 31, 2020

(86) PCT No.: PCT/US2020/044551
§ 371 (c)(1),
(2) Date: Jan. 31, 2022

(87) PCT Pub. No.: WO2021/022185
PCT Pub. Date: Feb. 4, 2021

(65) Prior Publication Data
US 2022/0175938 A1 Jun. 9, 2022

Related U.S. Application Data

(60) Provisional application No. 62/881,755, filed on Aug. 1, 2019.

(51) Int. Cl.
*A61K 47/58* (2017.01)
*C08F 222/10* (2006.01)
*C08F 228/02* (2006.01)
*B82Y 20/00* (2011.01)

(52) U.S. Cl.
CPC .......... *A61K 47/58* (2017.08); *C08F 222/102* (2020.02); *C08F 228/02* (2013.01); *B82Y 20/00* (2013.01)

(58) Field of Classification Search
CPC .... A61K 47/58; C08F 222/102; C08F 228/02
See application file for complete search history.

(56) References Cited

U.S. PATENT DOCUMENTS

| | | |
|---|---|---|
| 8,980,295 B2 | 3/2015 | Kao et al. |
| 2011/0159025 A1 | 6/2011 | Littman et al. |
| 2017/0136108 A1 | 5/2017 | Mahr et al. |
| 2018/0046751 A1 | 2/2018 | Vaske et al. |

OTHER PUBLICATIONS

Zaquen et al., "Facile Design of Degradable Poly(β-thioester)s with Tunable Structure and Functionality", 2014, Journal of Polymer Science, Part A: Polymer Chemistry, vol. 52, pp. 178-187. (Year: 2014).*
Vandenbergh et al., "Synthesis of (Bio)-Degradable Poly(β-thioester)s via Amine Catalyzed Thiol-Ene Click Polymerization", 2012, Macromolecular Chemistry and Physics, vol. 213, pp. 2611-2617. (Year: 2012).*
PCT Application No. US2021/044551, International Search Report and Written Opinion dated Jan. 4, 2021.
Grippin et al., Dendritic Cell-Activating Magnet Nanoparticles Enable Early Prediction of Antitumor Response with Magnet Resonance Imaging ACS Nano. Nov. 15, 2019, vol. 13, pp. 13884-13898.

* cited by examiner

*Primary Examiner* — Michael B. Pallay
(74) *Attorney, Agent, or Firm* — Lathrop GPM LLP; Laura A. Labeots

(57) ABSTRACT

The disclosure describes poly(β-thioester) polymers and polymeric nanoparticles, pharmaceutical compositions comprising these materials, their use in the treatment of cancer and infectious disease, and machine learning methods for identifying and selecting them.

3 Claims, 20 Drawing Sheets

POLY(BETA-THIOESTER) POLYMERS AND POLYMERIC NANOPARTICLES

CROSS REFERENCE TO RELATED APPLICATIONS

This application is a 371 US national stage application, which claims priority to pending PCT/US2020/044551 filed on Jul. 31, 2020, which claims the benefit of U.S. Provisional Application No. 62/881,755, filed on Aug. 1, 2019. The entire contents of the above-referenced patent applications are incorporated by reference in their entirety herein.

BACKGROUND

The goal of a therapeutic cancer vaccine is to stimulate specific immunity against tumors whilst sparring normal tissues, leading to tumor lysis and long lasting, system immunological memory which protects against recurrent disease and metastasis. After over two years of experimental cancer vaccine research, immunization with peptide antigens has demonstrated excellent feasibility and safety. Further, tumor regression has been repeatedly observed in various malignancies. Accordingly, vaccination remains a promising cancer treatment, particularly in combination with checkpoint inhibitor therapies. This is because patients who lack CD8$^+$ cytotoxic T lymphocytes do not respond to checkpoint inhibition. Therefore, combining checkpoint inhibitor therapy with cancer vaccination will likely benefit a significant patient population.

Therapeutic cancer vaccines achieve tumor immunity by delivery cancer peptide antigens to antigen presenting cells (APCs), the primary of which are dendritic cells (DCs). DCs which express co-stimulatory molecules and cytokines, alongside presenting antigenic fragments on the MHCI complex, induce the activation of CD8$^+$ cytotoxic T lymphocytes (CTLs). CTLs then recognize cancer cells and induce cell death through the release of perfornin and granzyme. Typically, cancer peptides are administered alongside adjuvants, which enhance delivery of antigen to APCs and induce the expression of co-stimulatory molecules and cytokines. Therefore, vaccine adjuvants dictate the type and magnitude of T cell response after vaccination.

The handful of adjuvants which are currently approved by the FDA overcome few of the challenges associated with peptide antigens. For example, alum, the most widely used vaccine adjuvant, is effective at improving antigen delivery to dendritic cells, but predominantly elicits a humoral (B-cell mediated) immune response. This type of immune response is mediated by antibodies and is most effective against extracellular bacteria and parasites. Conversely, Polyriboinosinic-polyribocytidylic acid (poly(I:C)) is a toll-like receptor (TLR) agonist which induces cell-mediated immunity (leading to CTL activation) but does not improve antigen delivery to dendritic cells. Further, the widespread applicability of many adjuvants is limited by factors such as high cost of goods, limited freedom to operate and compliance with regulatory issues. In aggregate, there is an urgent demand to develop adjuvants which overcome all challenges associated with peptide vaccines, alongside using sustainable formulations which have long product lifetimes. There is a need for improved vaccine adjuvants.

SUMMARY

Provided herein are polymers of Formula (I):

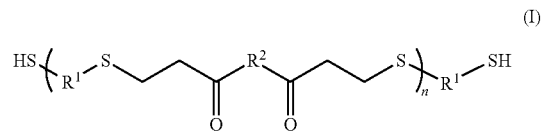

(I)

or a pharmaceutically acceptable salt thereof, wherein, $R^1$ is

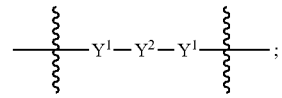

$Y^1$ is $C_{1-3}$ alkyl, ($C_{1-6}$ alkyl)-NHC(=O), C=O, 5 to 10-membered heteroaryl, or absent, wherein heteroaryl is optionally substituted, independently for each occurrence, one, two, or three times with $C_{1-3}$ alkyl, $C_{1-3}$ alkoxy, $C_{1-3}$ haloalkyl, halogen, or 6 to 10-membered aryl;

$Y^2$ is $C_{1-6}$ alkyl, 6 to 10-membered aryl, biphenyl, 5 to 10-membered heteroaryl, $(CH_2CH_2O)_pCH_2CH_2$, C=N—($C_{1-6}$ alkyl)-N=C, O, S, or $SO_2$, wherein the alkyl, aryl, biphenyl, and heteroaryl are optionally substituted, independently for each occurrence, one, two, or three times with $C_{1-6}$ alkyl, $C_{1-6}$ alkoxy, $C_{1-6}$ haloalkyl, ($C_{0-3}$ alkyl)-OH, $NH_2$, $NH(C_{1-6}$ alkyl), $N(C_{1-6}$ alkyl)$_2$, halogen, or carboxylic acid;

$R^2$ is $C_{1-6}$ alkyl, 6 to 10-membered aryl, O, or

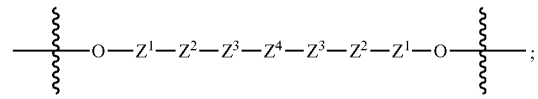

$Z^1$ is $C_{1-6}$ alkyl or 6 to 10-membered aryl;

$Z^2$ is O, O(C=O)O, or absent;

$Z^3$ is 6 to 10-membered aryl, 5 to 10-membered heteroaryl, or absent;

$Z^4$ is $C_{1-6}$ alkyl, 5 to 15-membered cycloalkyl, 5 to 15-membered heterocyclyl, 6 to 14-membered aryl, 5 to 15-membered heteroaryl, or (C=O)O-(6 to 10-membered aryl)-O(C=O), each of which are optionally substituted, independently for each occurrence, one, two, or three times with $C_{1-3}$ alkyl, $C_{1-3}$ haloalkyl, or halogen;

n is 25-250;

p is 1, 2, 3, or 4; and wherein $R^1$, $R^2$, $Y^1$, $Y^2$, $Z^1$, $Z^2$, $Z^3$, and $Z^4$ are each, independently, the same for every occurrence in the polymer.

The disclosure also provides polymers of Formula (II):

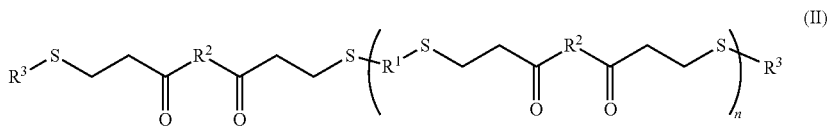

or a pharmaceutically acceptable salt thereof, wherein, $R^1$ is

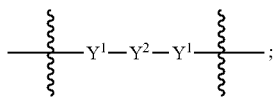

$Y^1$ is $C_{1-3}$ alkyl, ($C_{1-6}$ alkyl)-NHC(=O), C=O, 5 to 10-membered heteroaryl, or absent, wherein heteroaryl is optionally substituted, independently for each occurrence, one, two, or three times with $C_{1-3}$ alkyl, $C_{1-3}$ alkoxy, $C_{1-3}$ haloalkyl, halogen, or 6 to 10-membered aryl;

$Y^2$ is $C_{1-6}$ alkyl, 6 to 10-membered aryl, biphenyl, 5 to 10-membered heteroaryl, $(CH_2CH_2O)_pCH_2CH_2$, C=N—($C_{1-6}$ alkyl)-N=C, O, S, or $SO_2$, wherein the alkyl, aryl, biphenyl, and heteroaryl are optionally substituted, independently for each occurrence, one, two, or three times with $C_{1-6}$ alkyl, $C_{1-6}$ alkoxy, $C_{1-6}$ haloalkyl, ($C_{0-3}$ alkyl)-OH, $NH_2$, NH($C_{1-6}$ alkyl), N($C_{1-6}$ alkyl)$_2$, halogen, or carboxylic acid;

$R^2$ is $C_{1-6}$ alkyl, 6 to 10-membered aryl, O, or

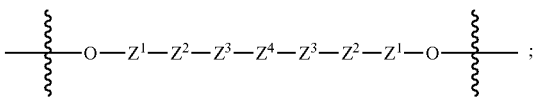

$Z^1$ is $C_{1-6}$ alkyl or 6 to 10-membered aryl;
$Z^2$ is O, O(C=O)O, or absent;
$Z^3$ is 6 to 10-membered aryl, 5 to 10-membered heteroaryl, or absent;
$Z^4$ is $C_{1-6}$ alkyl, 5 to 15-membered cycloalkyl, 5 to 15-membered heterocyclyl, 6 to 14-membered aryl, 5 to 15-membered heteroaryl, or (C=O)O-(6 to 10-membered aryl)-O(C=O), each of which are optionally substituted, independently for each occurrence, one, two, or three times with $C_{1-3}$ alkyl, $C_{1-3}$ haloalkyl, or halogen;

$R^3$ is $C_{1-6}$ alkyl, C(=O)—$C_{1-6}$ alkyl, 6 to 10-membered aryl, 5 to 10-membered heteroaryl, ($C_{1-6}$ alkyl)-(6 to 10-membered aryl), ($C_{1-6}$ alkyl)-(5 to 10-membered heteroaryl), and 5 to 15-membered heterocyclyl, each of which is optionally substituted, independently for each occurrence, one, two, or three times, independently, with $C_{1-3}$ alkyl, $C_{1-3}$ alkoxy, $C_{1-3}$ haloalkyl, acetamide, carboxylic acid, silyl, hydroxyl, cyano, nitro, and halogen;

n is 25-250;
p is 1, 2, 3, or 4; and
wherein $R^1$, $R^2$, $R^3$, $Y^1$, $Y^2$, $Z^1$, $Z^2$, $Z^3$, and $Z^4$ are each, independently, the same for every occurrence in the polymer.

In an embodiment, of the polymers of the disclosure, $Y^2$ is $C_{1-6}$ alkyl, 6 to 10-membered aryl, biphenyl 5 to 10-membered heteroaryl, C=N—($C_{1-6}$ alkyl)-N=C, S, or $SO_2$, wherein the alkyl is substituted, independently for each occurrence, one, two, or three times with $C_{1-6}$ alkyl, $C_{1-6}$ alkoxy, $C_{1-6}$ haloalkyl, ($C_{0-3}$ alkyl)-OH, $NH_2$, NH($C_{1-6}$ alkyl), N($C_{1-6}$ alkyl)$_2$, halogen, or carboxylic acid, and wherein the aryl, and heteroaryl are optionally substituted, independently for each occurrence, one, two, or three times with $C_{1-6}$ alkyl, $C_{1-6}$ alkoxy, $C_{1-6}$ haloalkyl, ($C_{0-3}$ alkyl)-OH, $NH_2$, NH($C_{1-6}$ alkyl), N($C_{1-6}$ alkyl)$_2$, halogen, or carboxylic acid.

In another embodiment, $R^2$ is 6 to 10-membered aryl, O, or

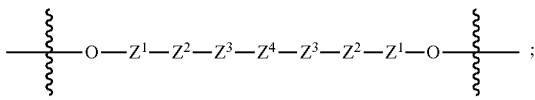

$Z^1$ is $C_{1-6}$ alkyl or 6 to 10-membered aryl;
$Z^2$ is O, O(C=O)O, or absent;
$Z^3$ is 6 to 10-membered aryl, 5 to 10-membered heteroaryl, or absent; and
$Z^4$ is $C_{1-6}$ alkyl, 5 to 15-membered cycloalkyl, 5 to 15-membered heterocyclyl, 6 to 14-membered aryl, 5 to 15-membered heteroaryl, or (C=O)O-(6 to 10-membered aryl)-O(C=O), each of which are optionally substituted, independently for each occurrence, one, two, or three times with $C_{1-3}$ alkyl, $C_{1-3}$ haloalkyl, or halogen.

In another embodiment, $R^1$ is selected from the group consisting of R-101, R-102, R-103, R-104, R-105, R-106, R-107, R-108, R-109, R-110, R-111, R-112, R-113, R-114, R-115, R-116, R-117, R-118, R-119, and R-120. In another embodiment, $R^2$ is selected from the group consisting of R-201, R-202, R-203, R-204, R-205, R-206, R-207, R-208, R-209, R-210, R-211, R-212, R-213, R-214, R-215, R-216, and R-217. In another embodiment, $R^3$ is selected from the group consisting of R-301, R-302, R-303, R-304, R-305, R-306, R-307, R-308, and R-309.

In another embodiment, the polymer is selected from the group consisting of A1-A80. In another embodiment, the polymer is selected from the group consisting of B1-B84. In yet another embodiment, the polymer is B18.

The disclosure also provides a population of polymeric nanoparticles comprising one or more of the polymers of the disclosure and PLGA-PEG.

The disclosure also provides a method of treating cancer, comprising administering to a subject in need a polymer of the disclosure or a population of nanoparticles of the disclosure. In an embodiment, the cancer is selected from the group consisting of breast cancer, lung cancer, prostate cancer, colorectal cancer, skin cancer, bladder cancer, non-Hodgkin's lymphoma, kidney cancer, uterine cancer, leukemia, pancreatic cancer, thyroid cancer, and liver cancer. In another embodiment, the cancer is skin cancer. In another embodiment, the cancer is melanoma.

The disclosure also provides a method of treating an infectious disease, comprising administering to a subject in need a polymer of the disclosure or a population of nanoparticles of the disclosure.

The disclosure also provides a method of modulating the immune system, comprising administering to a subject in need a polymer of the disclosure or a population of nanoparticles of the disclosure. In an embodiment, modulation of the immune system is accomplished by upregulating or downregulating the activity of dendritic cells.

The disclosure also provides a method of enhancing dendritic cell-mediated T cell activation by contacting one or more dendritic cells with a polymer of the disclosure or a population of nanoparticles of the disclosure.

The disclosure also provides a method of inducing the expression of CD86, CD80, and/or CD40 in a subject in need thereof, the method comprising administering to the subject a polymer of the disclosure or a population of nanoparticles of the disclosure. In some embodiments, increase in expression of CD86, CD80 and/or CD40 occurs in dendritic cells.

The disclosure also provides a method of increasing cross-presentation of antigen. In some embodiments, the increased cross-presentation of antigen occurs in dendritic cells. In some embodiments, an increase of cross-presentation of antigen is demonstrated by increased cell surface presentation of antigen in an MHCI molecule on the surface of a cell. In some embodiments, the cell is a dendritic cell.

The disclosure also provides a method of increasing the levels interferon-γ in a subject in need thereof, the method comprising administering to the subject a polymer of the disclosure or a population of nanoparticles of the disclosure.

The disclosure also provides a method of increasing the fraction of antigen-specific CD8+ T cells in a subject in need thereof, the method comprising administering to the subject a polymer of the disclosure or a population of nanoparticles of the disclosure.

The disclosure also provides a method of synthesizing a nanoparticle library comprising: (1) selecting a dithiol and a diacrylate; (2) reacting the dithiol and the diacrylate with triethylamine to produce a polymer; (3) precipitating the polymer; (4) washing the polymer; (5) preparing a mixture comprising the polymer and PLGA-PEG in solvent; (6) precipitating the mixture to produce nanoparticles; and (7) repeating steps 2-6 at least one more time, selecting, during each repetition, a different combination of dithiol and diacrylate.

In an embodiment, step (2) is carried out in THF, dichloromethane, DMF, DMSO, or without solvent. In another embodiment, step (2) is carried out in THF. In an embodiment, precipitating the polymer in step (3) is performed in water, methanol, petroleum ether, or diethyl ether. In another embodiment, washing the polymer in step (4) is performed with water, methanol, petroleum ether, or diethyl ether.

In an embodiment, the method further comprises the follow steps after step (4): (4.1) selecting a monothiol; (4.2) reacting the polymer with the monothiol and triethylamine to produce a capped polymer; (4.3) precipitating the capped polymer; (4.4) washing the capped polymer; wherein the capped polymer is used in place of the polymer in subsequent steps 5-7.

In an embodiment, precipitating the polymer in step (4.3) is performed in water, methanol, petroleum ether, or diethyl ether. In another embodiment, washing the polymer in step (4.4) is performed with water, methanol, petroleum ether, or diethyl ether.

In an embodiment, the solvent of step (5) is DMSO, DMF, acetone, acetonitrile, or THF. In another embodiment, the solvent of step (5) is DMSO. In an embodiment, precipitation of the mixture in step (6) is performed in water. In another embodiment, precipitation of the mixture in step (6) is performed in water containing a surfactant. In a further embodiment, the surfactant is selected from the group consisting of tween 80, tween 20, and poly(vinyl alcohol).

In an embodiment, the polymer is not centrifuged prior to precipitation into nanoparticles.

The disclosure also provides a method of predicting dendritic cell activation by a test polymer comprising: identifying the monomeric units of the test polymer and of a training set of polymers, wherein the training set of polymers have known activity in at least one immune activation pathway; categorizing the monomeric units into chemically distinct groups; generating a set of molecular descriptors of the monomeric units in the training set; deriving an algorithm for each chemically distinct group, wherein each algorithm determines the ability of the monomeric units to activate a dendritic cell by configuring the molecular descriptors of the monomeric units with experimentally derived biological data for the polymers in the training set; combining the algorithms for each chemically distinct group into a combined algorithm; determining a set of molecular descriptors for the test polymer; and predicting dendritic cell activation of the test polymer using the combined algorithm.

In an embodiment, the activity in at least one immune activation pathway is selected from the group consisting of MHCI upregulation, MHCII upregulation, CD40 upregulation, CD80 upregulation, and CD86 upregulation. In another embodiment, the chemically distinct groups are diacrylates, dithiols, acrylates, and monothiols. In an embodiment, the algorithms are derived using random forest regression.

In an embodiment, the experimentally derived biological data is represented as "percentage activation compared to positive control" using equation (I):

$$\frac{[\% \text{ activated cells}]_{polymer} - [\% \text{ activated cells}]_{antigen}}{[\% \text{ activated cells}]_{LPS} - [\% \text{ activated cells}]_{antigen}} \quad (I)$$

wherein, [% activated cells]$_{polymer}$ is defined as the percentage of dendritic cells exhibiting activation of the at least one immune activation pathway upon stimulation with a polymer of the training set; [% activated]$_{antigen}$ is defined as the percentage of dendritic cells exhibiting activation of the at least one immune activation pathway upon stimulation with an antigen; and [% activated cells]$_{LPS}$ is defined as the percentage of dendritic cells exhibiting activation of the at least one immune activation pathway upon stimulation with lipopolysaccharide.

In an embodiment, the experimentally derived biological data is represented as "absolute activation" using equation (II):

$$[\% \text{ activated cells}]_{polymer} - [\% \text{ activated cells}]_{antigen} \quad \text{(II)}$$

wherein, [% activated cells]$_{polymer}$ is defined as the percentage of dendritic cells exhibiting activation of the at least one immune activation pathway upon stimulation with a polymer of the training set, and [% activated cells]$_{antigen}$ is defined as the percentage of dendritic cells exhibiting activation of the at least one immune activation pathway upon stimulation with an antigen.

In an embodiment, the experimentally derived biological data is represented as "relative activation" using equation (III):

$$\frac{[\% \text{ activated cells}]_{polymer}}{[\% \text{ activated cells}]_{antigen}} \quad \text{(III)}$$

wherein, [% activated cells]$_{polymer}$ is defined as the percentage of dendritic cells exhibiting activation of the at least one immune activation pathway upon stimulation with a polymer of the training set, and [% activated cells]$_{antigen}$ is defined as the percentage of dendritic cells exhibiting activation of the at least one immune activation pathway upon stimulation with an antigen The disclosure also provides a method of identifying a polymer-based adjuvant for a vaccine comprising: selecting one or more test polymers with unknown activity in the activation of dendritic cells; determining a set of molecular descriptors for the one or more test polymers; by machine, accessing a body of data comprising molecular descriptors and dendritic cell activation data of a set of training polymers, wherein the body of data has been configured to derive an algorithm for determining the ability of a polymer to activate a dendritic cell based on its molecular descriptors; applying the set of molecular descriptors for the one or more test polymers to the algorithm; and identifying a polymer from the one or more test polymers for development into an adjuvant for a vaccine.

In an embodiment, the vaccine is for the treatment of cancer. In a further embodiment, the cancer is skin cancer. In a further embodiment, the cancer is melanoma.

In an embodiment, the one or more test polymers comprise monomeric units selected from the group consisting of diacrylates, dithiols, acrylates, and monothiols.

The disclosure also provides a method of preparing an adjuvant for a vaccine comprising: by machine, accessing a body of data comprising molecular descriptors and dendritic cell activation data of a set of training polymers, wherein the body of data has been configured to derive an algorithm for predicting the ability of a polymer to activate a dendritic cell based on its molecular descriptors; using said algorithm to select a polymer with predicted activity in the activation of dendritic cells; synthesizing the polymer; and precipitating the polymer into nanoparticles.

In an embodiment, the vaccine is for the treatment of cancer. In a further embodiment, the cancer is skin cancer. In a further embodiment, the cancer is melanoma.

In an embodiment, the polymer comprises monomeric units selected from the group consisting of diacrylates, dithiols, acrylates, and monothiols.

In an embodiment, the method further comprises validating the ability of the nanoparticles to activate dendritic cells. In another embodiment, the validation step comprises in vitro determination of the activation of an immune activation pathway selected from MHCI activation, MHCII activation, CD40 activation, CD80 activation, and CD86 activation.

DETAILED DESCRIPTION

Figure 1:
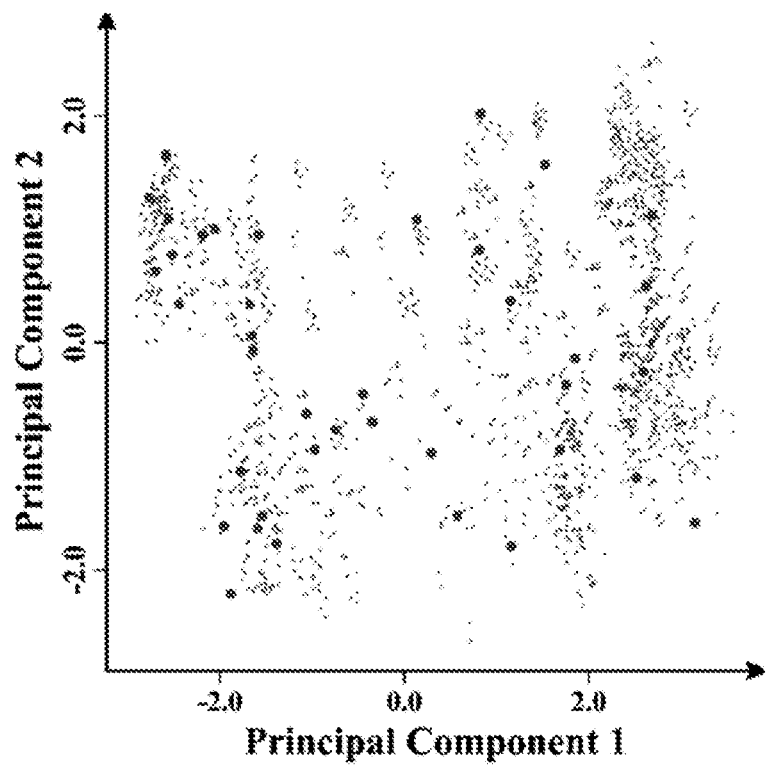
FIG. 1 is a plot displaying principal component analysis of selected base polymers (large dots) against the entire base polymer library (small dots).

Provided herein are poly(β-thioester) polymers of Formula (I):

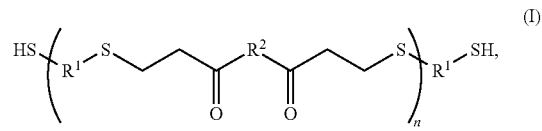

of Formula (II):

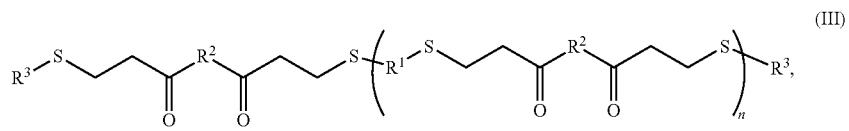

and of Formula (III):

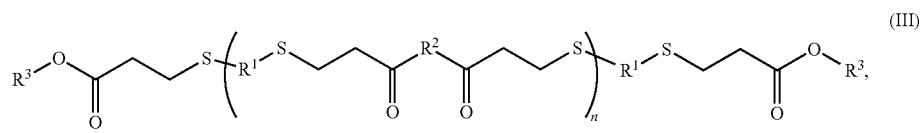

which are useful in the treatment of cancer, infectious diseases, and autoimmune disorders.

Definitions

Listed below are definitions of various terms used to describe this invention. These definitions apply to the terms as they are used throughout this specification and claims, unless otherwise limited in specific instances, either individually or as part of a larger group. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "a polymer" means one polymer or more than one polymer. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

As used in the specification and in the claims, the term "comprising" can include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

The term "administration" or the like as used herein refers to the provision of a therapeutic agent to a subject. Multiple techniques of administering a therapeutic agent exist in the art including, but not limited to, oral, aerosol, parenteral (e.g., intravenous, intramuscular, intraperitoneal, or subcutaneous), ophthalmic, pulmonary, and topical administration. A therapeutic agent may be administered, by nonlimiting example, in the form of a vaccine, a capsule or tablet, a suppository, or an implant. Preferably, the polymers and nanoparticles disclosed herein are administered in the form of a vaccine.

The term "treat," "treated," "treating," or "treatment" includes the diminishment or alleviation of at least one symptom associated or caused by the state, disorder, or disease being treated. In certain methods disclosed herein, treatment comprises bringing into contact with a dendritic cell an effective amount of a polymer or a population of nanoparticles of the disclosure.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed polymers wherein the parent polymer is modified by converting one or more existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent polymer formed, for example, from non-toxic inorganic or organic acids. The pharmaceutically acceptable salts of the present disclosure can be synthesized from the parent polymer which contains a basic or acidic moiety by conventional chemical methods. Generally, such salts can be prepared by reacting the free acid or base forms of these polymers with a stoichiometric amount of the appropriate base or acid in water or in an organic solvent, or in a mixture of the two. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of one or more polymers or populations of nanoparticles useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

The term "pharmaceutical combination" as used herein means a product that results from the mixing or combining of more than one active ingredient and includes both fixed and non-fixed combinations of the active ingredients. The term "fixed combination" means that the active ingredients, e.g., a population of nanoparticles of the disclosure and a co-agent, are both administered to a patient simultaneously in the form of a single entity or dosage. The term "non-fixed combination" means that the active ingredients, e.g., a population of nanoparticles of the disclosure and a co-agent, are both administered to a patient as separate entities either simultaneously, concurrently or sequentially with no specific time limits, wherein such administration provides therapeutically effective levels of the two agents in the body of the patient. The latter also applies to cocktail therapy, e.g., the administration of three or more active ingredients.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a polymer or a population of nanoparticles within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the polymer or population of nanoparticles of the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other nontoxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the polymer or population of nanoparticles of the disclosure, and are physiologically acceptable to the patient. Supplementary active agents may also be incorporated into the compositions. The "pharmaceutically acceptable carrier" may further include a pharmaceutically acceptable salt of a polymer of the invention. Other additional ingredients that may be included in the pharmaceutical compositions used in the practice of the invention are known in the art and described, for example, in Remington's Pharmaceutical Sciences (Genaro, Ed., Mack Publishing Co., 1985, Easton, Pa.), which is incorporated herein by reference.

As used herein, the term "alkyl," by itself or as part of another substituent means, unless otherwise stated, a straight or branched chain hydrocarbon having the number of carbon atoms designated (i.e., $C_1$-$C_6$ alkyl means an alkyl having one to six carbon atoms) and includes straight and branched chains. Examples of alkyl groups include methyl, ethyl, propyl, isopropyl, butyl, isobutyl, tert butyl, pentyl, neopentyl, and hexyl. Examples of $C_1$-$C_6$ alkyl include ethyl, methyl, isopropyl, isobutyl, n-pentyl, and n-hexyl. Examples of branched alkyl groups include 1-methylethyl, 1-methylpropyl, neopentyl, 2-methylpropyl, 2-methylbutyl, and 3-ethylpentyl.

As used herein, the term "haloalkyl" refers to an alkyl group, as defined above, substituted with one or more halo substituents, wherein alkyl and halo are as defined herein. Haloalkyl includes, by way of example, chloromethyl, trifluoromethyl, bromoethyl, chlorofluoroethyl, and the like.

As used herein, the term "alkoxy" refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like.

As used herein, the term "halo" or "halogen" alone or as pad of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is partially or fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic or tricyclic structures that may be bridged or spirocyclic in nature with each individual ring within the bi- or tricycle varying from 3-8 atoms. The term "cycloalkyl" includes, but is not limited to, cyclopropyl, cyclobutyl, cyclopentyl, cyclohexyl, cyclohexenyl, bicyclo[3.1.0]hexyl, spiro[3.3]heptanyl, bicyclo[1.1.1]pentyl, and tricyclo[5.2.1.0$^{2,6}$]decane.

As used herein, the term "heterocyclyl" or "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocyclyl also includes bicyclic structures that may be bridged or spirocyclic in nature with each individual ring within the bicycle varying from 3-8 atoms, and containing 0, 1, or 2 N, O, or S atoms. The term "heterocyclyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, anthracenyl, acenaphthyl, fluorenyl, indenyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. If the rings are fused, one of the rings must be fully unsaturated and the fused ring(s) may be fully saturated, partially unsaturated or fully unsaturated. The term "heteroaryl" includes, but is not limited to, furanyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

It is to be understood that if an aryl, heteroaryl, cycloalkyl, or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thienyl, and so forth.

As used herein, the term "substituted" means that an atom or group of atoms has replaced hydrogen as the substituent attached to another group.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

Polymers and Nanoparticles of the Disclosure

Provided herein are polymers that are useful in the modulation of dendritic cell activity and may, therefore, be effective in the treatment of cancer, infectious diseases, and autoimmune disorders. The polymers may be formed into nanoparticles and used, for instance, as an adjuvant in the formulation of a vaccine.

A first aspect of the disclosure relates to compounds of Formula (I):

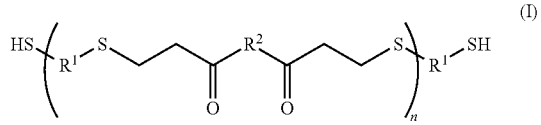

(I)

or a pharmaceutically acceptable salt thereof, wherein,
$R^1$ is

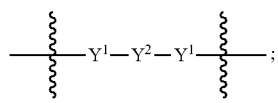

$Y^1$ is $C_{1-3}$ alkyl, $(C_{1-6}$ alkyl$)$-NHC(=O), C=O, 5 to 10-membered heteroaryl, or absent, wherein heteroaryl is optionally substituted, independently for each occurrence, one, two, or three times with $C_{1-3}$ alkyl, $C_{1-3}$ alkoxy, $C_{1-3}$ haloalkyl, halogen, or 6 to 10-membered aryl;

$Y^2$ is $C_{1-6}$ alkyl, 6 to 10-membered aryl, biphenyl, 5 to 10-membered heteroaryl, $(CH_2CH_2O)_pCH_2CH_2$, C=N—$(C_{1-6}$ alkyl$)$-N=C, O, S, or $SO_2$, wherein the alkyl, aryl, biphenyl, and heteroaryl are optionally substituted, independently for each occurrence, one, two, or three times with $C_{1-6}$ alkyl, $C_{1-6}$ alkoxy, $C_{1-6}$ haloalkyl, $(C_{0-3}$ alkyl$)$-OH, $NH_2$, $NH(C_{1-6}$ alkyl$)$, $N(C_{1-6}$ alkyl$)_2$, halogen, or carboxylic acid;

$R^2$ is $C_{1-6}$ alkyl, 6 to 10-membered aryl, O, or

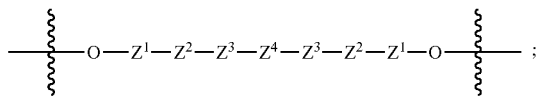

$Z^1$ is $C_{1-6}$ alkyl or 6 to 10-membered aryl;

$Z^2$ is O, O(C=O)O, or absent;

$Z^3$ is 6 to 10-membered aryl, 5 to 10-membered heteroaryl, or absent;

$Z^4$ is $C_{1-6}$ alkyl, 5 to 15-membered cycloalkyl, 5 to 15-membered heterocyclyl, 6 to 14-membered aryl, 5 to 15-membered heteroaryl, or (C=O)O-(6 to 10-membered aryl)-O(C=O), each of which are optionally substituted, independently for each occurrence, one, two, or three times with $C_{1-3}$ alkyl, $C_{1-3}$ haloalkyl, or halogen;

n is 25-250;

p is 1, 2, 3, or 4; and wherein $R^1$, $R^2$, $Y^1$, $Y^2$, $Z^1$, $Z^2$, $Z^3$, and $Z^4$ are each, independently, the same for every occurrence in the polymer.

In an embodiment, $Y^2$ is branched $C_{3-6}$ alkyl, 6 to 10-membered aryl, biphenyl, 5 to 10-membered heteroaryl, $(CH_2CH_2O)_pCH_2CH_2$, C=N—$(C_{1-6}$ alkyl$)$-N=C, O, S, or $SO_2$, wherein the alkyl, aryl, biphenyl, and heteroaryl are optionally substituted, independently for each occurrence, one, two, or three times with $C_{1-6}$ alkyl, $C_{1-6}$ alkoxy, $C_{1-6}$ haloalkyl, $(C_{0-3}$ alkyl$)$-OH, $NH_2$, $NH(C_{1-6}$ alkyl$)$, $N(C_{1-6}$ alkyl$)_2$, halogen, or carboxylic acid.

In an embodiment, $Y^2$ is $C_{1-6}$ alkyl, 6 to 10-membered aryl, biphenyl 5 to 10-membered heteroaryl, C=N—$(C_{1-6}$ alkyl$)$-N=C, S, or $SO_2$, wherein the alkyl is substituted, independently for each occurrence, one, two, or three times with $C_{1-6}$ alkyl, $C_{1-6}$ alkoxy, $C_{1-6}$ haloalkyl, $(C_{0-3}$ alkyl$)$-OH, $NH_2$, $NH(C_{1-6}$ alkyl$)$, $N(C_{1-6}$ alkyl$)_2$, halogen, or carboxylic acid, and wherein the aryl, and heteroaryl are optionally substituted, independently for each occurrence, one, two, or three times with $C_{1-6}$ alkyl, $C_{1-6}$ alkoxy, $C_{1-6}$ haloalkyl, $(C_{0-3}$ alkyl$)$-OH, $NH_2$, $NH(C_{1-6}$ alkyl$)$, $N(C_{1-6}$ alkyl$)_2$, halogen, or carboxylic acid.

In an embodiment, $Y^2$ is $C_{1-6}$ alkyl, wherein alkyl is substituted one, two, or three times with $C_{1-6}$ alkyl, thereby forming a branched linker.

In an embodiment, $Y^2$ is 6 to 10-membered aryl, biphenyl 5 to 10-membered heteroaryl, C=N—$(C_{1-6}$ alkyl$)$-N=C, S, or $SO_2$, wherein the aryl and heteroaryl are optionally substituted, independently for each occurrence, one, two, or three times with $C_{1-6}$ alkyl, $C_{1-6}$ alkoxy, $C_{1-6}$ haloalkyl, $(C_{0-3}$ alkyl$)$-OH, $NH_2$, $NH(C_{1-6}$ alkyl$)$, $N(C_{1-6}$ alkyl$)_2$, halogen, or carboxylic acid.

In an embodiment, $R^2$ is branched $C_{3-6}$ alkyl, 6 to 10-membered aryl, O, or

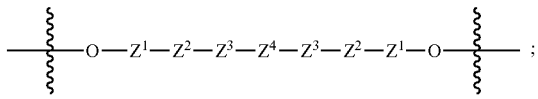

In an embodiment, $R^2$ is 6 to 10-membered aryl, O, or

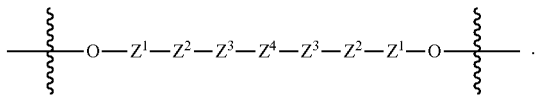

In an embodiment, $Z^1$ is branched $C_{3-6}$ alkyl or 6 to 10-membered aryl

In an embodiment, $Z^4$ is branched $C_{3-6}$ alkyl, 5 to 15-membered cycloalkyl, 5 to 15-membered heterocyclyl, 6 to 14-membered aryl, 5 to 15-membered heteroaryl, or (C=O)O-(6 to 10-membered aryl)-O(C=O), each of which are optionally substituted, independently for each occurrence, one, two, or three times with $C_{1-3}$ alkyl, $C_{1-3}$ haloalkyl, or halogen.

In preferred embodiments of Formula (I), $R^1$, $R^2$, $Y^1$, $Y^2$, $Z^1$, $Z^2$, $Z^3$, and $Z^4$ are each, independently, the same for every occurrence in the polymer. For instance, in a polymer wherein $Y^1$ is selected to be absent and $Y^2$ is selected to be butyl, $Y^1$ must be absent for every occurrence of $Y^1$ and $Y^2$ must be butyl for every occurrence of $Y^2$. By way of further example, every time variable $R^1$ appears in a given polymer of Formula (I), it represents a conserved group, wherein each of $Y^1$ and $Y^2$ are consistently and respectively selected to be the same for every occurrence within the polymer.

In an embodiment, $Y^1$ is absent, and $Y^2$ is 5 to 10-membered heteroaryl.

In an embodiment, $Y^1$ is $C_{1-3}$ alkyl, and $Y^2$ is 6 to 10-membered aryl, optionally substituted one, two, or three times with $C_{1-6}$ alkyl.

In an embodiment, $Y^1$ is absent, and $Y^2$ is $C_{1-6}$ alkyl.

In an embodiment, $Y^1$ is absent, and $Y^2$ is branched $C_{1-6}$ alkyl.

In an embodiment, $Y^1$ is absent, and $Y^2$ is $C_{1-6}$ alkyl substituted one, two, or three times with $C_{1-6}$ alkyl, thereby forming a branched linker.

In an embodiment, $Y^1$ is absent, and $Y^2$ is $C_{1-6}$ alkyl substituted, independently for each occurrence, one, two, or three times with $C_{1-6}$ alkyl, $C_{1-6}$ alkoxy, $C_{1-6}$ haloalkyl, $(C_{0-3}$ alkyl)-OH, $NH_2$, $NH(C_{1-6}$ alkyl), $N(C_{1-6}$ alkyl$)_2$, halogen, or carboxylic acid.

In an embodiment, $Y^1$ is absent, and $Y^2$ is propyl.

In an embodiment, $Y^1$ is absent, and $Y^2$ is butyl.

In an embodiment, $Y^1$ is absent, and $Y^2$ is pentyl.

In an embodiment, $Y^1$ is absent, and $Y^2$ is hexyl.

In an embodiment, $Y^1$ is absent, and $Y^2$ is $(CH_2CH_2O)_pCH_2CH_2$.

In an embodiment, $Y^1$ is absent, and $Y^2$ is $C_{1-6}$ alkyl substituted with $(C_{0-3}$ alkyl)-OH.

In an embodiment, $Y^1$ is $C_{1-3}$ alkyl, and $Y^2$ is S.

In an embodiment, $Y^1$ is absent, and $Y^2$ is 6 to 10-membered aryl, optionally substituted one, two, or three times with $C_{1-6}$ alkyl.

In an embodiment, $Y^1$ is 5 to 10-membered heteroaryl, optionally substituted, independently for each occurrence, one, two, or three times with $C_{1-3}$ alkyl, $C_{1-3}$ alkoxy, $C_{1-3}$ haloalkyl, halogen, or 6 to 10-membered aryl, and $Y^2$ is C=N—$(C_{1-6}$ alkyl)-N=C.

In an embodiment, $Y^1$ is absent, and $Y^2$ is 5 to 10-membered heteroaryl optionally substituted, independently for each occurrence, one, two, or three times with $C_{1-6}$ alkyl, $C_{1-6}$ alkoxy, $C_{1-6}$ haloalkyl, $(C_{0-3}$ alkyl)-OH, $NH_2$, $NH(C_{1-6}$ alkyl), $N(C_{1-6}$ alkyl$)_2$, halogen, or carboxylic acid.

In an embodiment, $Y^1$ is $(C_{1-6}$ alkyl)-NHC(=O), and $Y^2$ is 6 to 10-membered aryl.

In an embodiment, $Y^1$ is C=O, and $Y^2$ is 6 to 10-membered aryl.

In an embodiment, $Y^1$ is $C_{1-3}$ alkyl, and $Y^2$ is $SO_2$.

In an embodiment, $Y^1$ is absent, and $Y^2$ is biphenyl.

In an embodiment, $R^2$ is $C_{1-6}$ alkyl.

In an embodiment, $R^2$ is propyl.

In an embodiment, $R^2$ is butyl.

In an embodiment, $R^2$ is pentyl.

In an embodiment, $R^2$ is hexyl.

In an embodiment, $R^2$ is branched $C_{3-6}$ alkyl.

In an embodiment, $R^2$ is 1-methypropyl.

In an embodiment, $R^2$ is neopentyl.

In an embodiment, $R^2$ is 6 to 10-membered aryl.

In an embodiment, $R^2$ is O.

In an embodiment, $R^2$ is

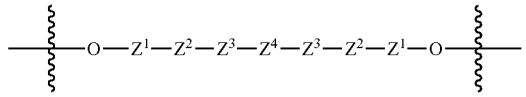

In an embodiment, $Z^1$ is $C_{1-6}$ alkyl, $Z^2$ is O, $Z^3$ is 6 to 10-membered aryl, and $Z^4$ is 6 to 14-membered aryl.

In an embodiment, $Z^1$ is $C_{1-6}$ alkyl, $Z^2$ is O, $Z^3$ is 6 to 10-membered aryl, and $Z^4$ is 5 to 15-membered cycloalkyl.

In an embodiment, $Z^1$ is $C_{1-6}$ alkyl, $Z^2$ is O, $Z^3$ is 6 to 10-membered aryl, and $Z^4$ is $C_{1-6}$ alkyl.

In an embodiment, $Z^1$ is $C_{1-6}$ alkyl, $Z^2$ is O, $Z^3$ is absent, and $Z^4$ is $C_{1-6}$ alkyl.

In an embodiment, $Z^1$ is $C_{1-6}$ alkyl, $Z^2$ is absent, $Z^3$ is absent, and $Z^4$ is 5 to 15-membered cycloalkyl.

In an embodiment, $Z^1$ is 6 to 10-membered aryl, $Z^2$ is absent, $Z^3$ is absent, and $Z^4$ is $C_{1-6}$ alkyl optionally substituted, independently for each occurrence, one, two, or three times with $C_{1-3}$ alkyl, $C_{1-3}$ haloalkyl, or halogen.

In an embodiment, $Z^1$ is $C_{1-6}$ alkyl, $Z^2$ is O, $Z^3$ is absent, and $Z^4$ is $C_{1-6}$ alkyl.

In an embodiment, $Z^1$ is branched $C_{3-6}$ alkyl, $Z^2$ is O, $Z^3$ is absent, and $Z^4$ is branched $C_{3-6}$ alkyl.

In an embodiment, $Z^1$ is $C_{1-6}$ alkyl, $Z^2$ is O, $Z^3$ is absent, and $Z^4$ is $C_{1-6}$ alkyl.

In an embodiment, $Z^1$ is $C_{1-6}$ alkyl, $Z^2$ is O(C=O)O, $Z^3$ is 6 to 10-membered aryl, and $Z^4$ is (C=O)O-(6 to 10-membered aryl)-O(C=O) optionally substituted, independently for each occurrence, one, two, or three times with $C_{1-3}$ alkyl, $C_{1-3}$ haloalkyl, or halogen.

In some embodiments of the polymer of Formula (I), $R^1$ has a structure of one of the following:

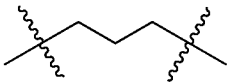

R-101

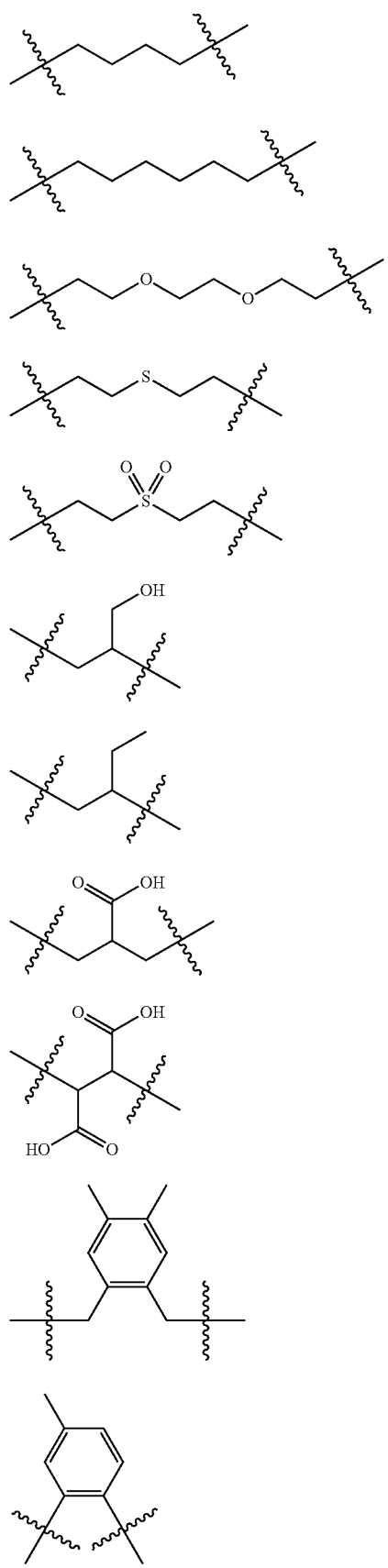

In some embodiments of the polymer of Formula (I), $R^2$ has a structure of one of the following:
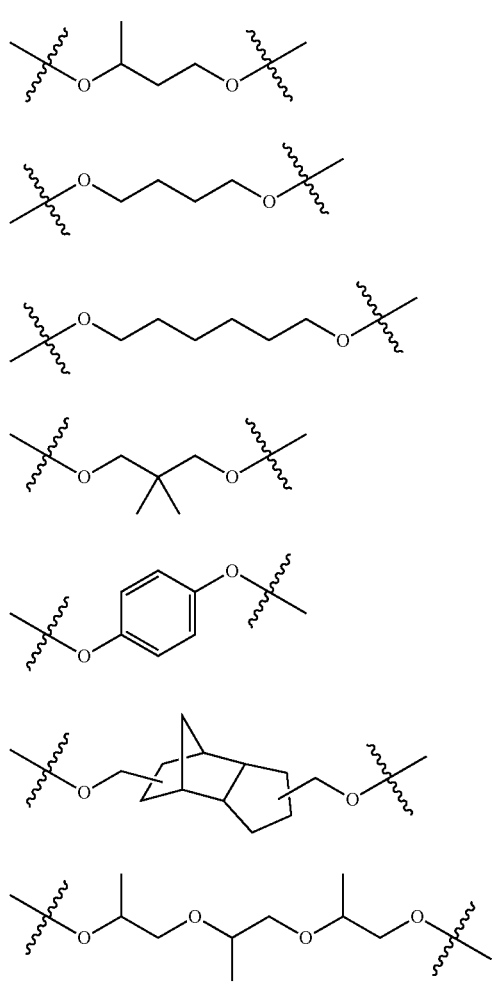
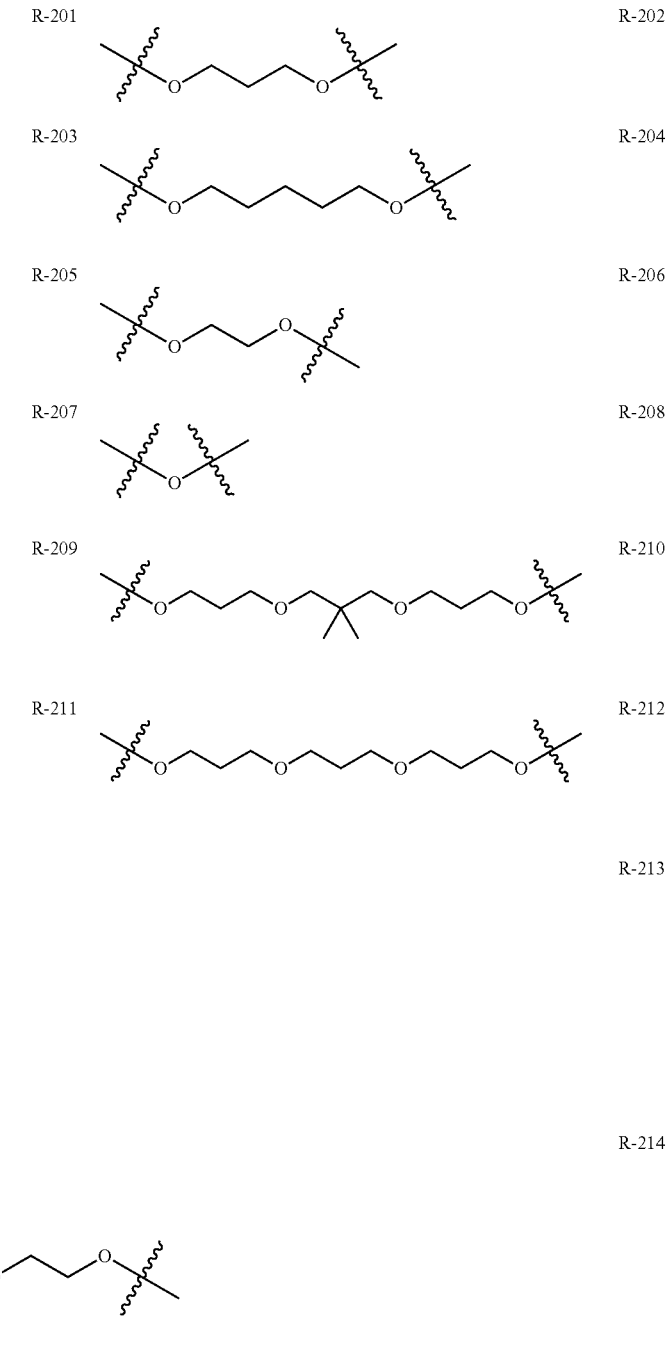
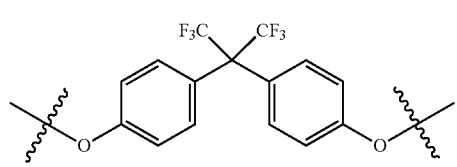

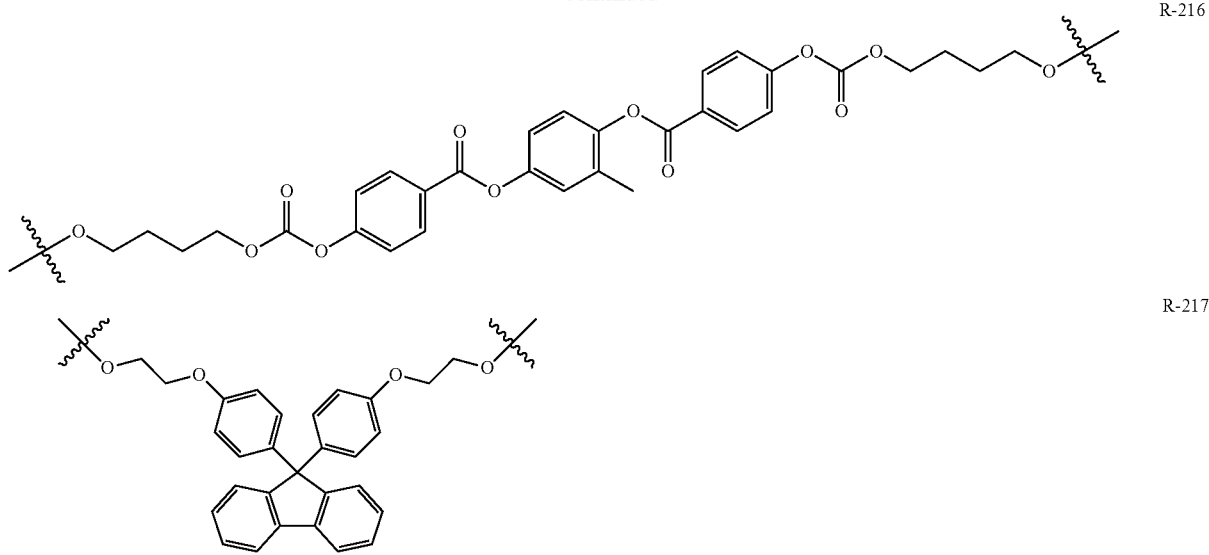

Non-limiting illustrative compounds of Formula (I) are exemplified in Table 1.

TABLE 1

| Peptide Identifier | R¹ | R² |
| --- | --- | --- |
| A1 | R-101 | R-201 |
| A2 | R-101 | R-214 |
| A3 | R-101 | R-204 |
| A4 | R-101 | R-207 |
| A5 | R-101 | R-211 |
| A6 | R-101 | R-210 |
| A7 | R-101 | R-203 |
| A8 | R-101 | R-205 |
| A9 | R-101 | R-202 |
| A10 | R-104 | R-201 |
| A11 | R-104 | R-214 |
| A12 | R-104 | R-204 |
| A13 | R-104 | R-207 |
| A14 | R-104 | R-211 |
| A15 | R-104 | R-210 |
| A16 | R-104 | R-203 |
| A17 | R-104 | R-205 |
| A18 | R-104 | R-202 |
| A19 | R-103 | R-201 |
| A20 | R-103 | R-214 |
| A21 | R-103 | R-204 |
| A22 | R-103 | R-207 |
| A23 | R-103 | R-211 |
| A24 | R-103 | R-210 |
| A25 | R-103 | R-203 |
| A26 | R-103 | R-205 |
| A27 | R-103 | R-202 |
| A28 | R-102 | R-201 |
| A29 | R-102 | R-214 |
| A30 | R-102 | R-204 |
| A31 | R-102 | R-207 |
| A32 | R-102 | R-211 |
| A33 | R-102 | R-210 |
| A34 | R-102 | R-203 |
| A35 | R-102 | R-205 |
| A36 | R-102 | R-202 |
| A37 | R-105 | R-201 |
| A38 | R-105 | R-214 |
| A39 | R-105 | R-204 |
| A40 | R-105 | R-207 |
| A41 | R-105 | R-211 |
| A42 | R-105 | R-210 |
| A43 | R-105 | R-203 |
| A44 | R-105 | R-205 |
| A45 | R-105 | R-202 |
| A46 | R-113 | R-201 |
| A47 | R-113 | R-214 |
| A48 | R-113 | R-204 |
| A49 | R-113 | R-207 |
| A50 | R-113 | R-211 |
| A51 | R-113 | R-210 |
| A52 | R-113 | R-203 |
| A53 | R-113 | R-205 |
| A54 | R-113 | R-202 |
| A55 | R-107 | R-201 |
| A56 | R-107 | R-214 |
| A57 | R-107 | R-204 |
| A58 | R-107 | R-207 |
| A59 | R-107 | R-211 |
| A60 | R-107 | R-210 |
| A61 | R-107 | R-203 |
| A62 | R-107 | R-205 |
| A63 | R-107 | R-202 |
| A64 | R-101 | R-217 |
| A65 | R-107 | R-217 |
| A66 | R-102 | R-217 |
| A67 | R-104 | R-217 |
| A68 | R-105 | R-217 |
| A69 | R-115 | R-201 |
| A70 | R-115 | R-205 |
| A71 | R-115 | R-211 |
| A72 | R-115 | R-207 |
| A73 | R-115 | R-214 |
| A74 | R-118 | R-216 |
| A75 | R-119 | R-217 |
| A76 | R-111 | R-209 |
| A77 | R-114 | R-208 |
| A78 | R-115 | R-213 |
| A79 | R-110 | R-209 |
| A80 | R-117 | R-212 |

A second aspect of the disclosure relates to compounds of Formula (II):

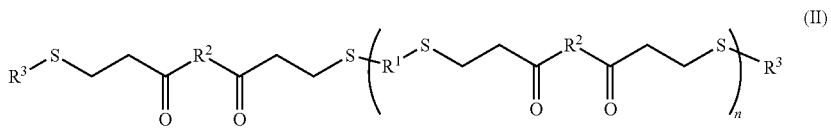

or a pharmaceutically acceptable salt thereof, wherein, $R^1$ is

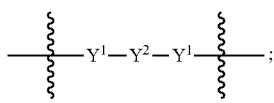

$Y^1$ is $C_{1-3}$ alkyl, $(C_{1-6}$ alkyl$)$-NHC($=$O), C$=$O, 5 to 10-membered heteroaryl, or absent, wherein heteroaryl is optionally substituted, independently for each occurrence, one, two, or three times with $C_{1-3}$ alkyl, $C_{1-3}$ alkoxy, $C_{1-3}$ haloalkyl, halogen, or 6 to 10-membered aryl;

$Y^2$ is $C_{1-6}$ alkyl, 6 to 10-membered aryl, biphenyl, 5 to 10-membered heteroaryl, $(CH_2CH_2O)_pCH_2CH_2$, C$=$N—$(C_{1-6}$ alkyl$)$-N$=$C, O, S, or $SO_2$, wherein the alkyl, aryl, biphenyl, and heteroaryl are optionally substituted, independently for each occurrence, one, two, or three times with $C_{1-6}$ alkyl, $C_{1-6}$ alkoxy, $C_{1-6}$ haloalkyl, $(C_{0-3}$ alkyl$)$-OH, $NH_2$, NH$(C_{1-6}$ alkyl$)$, N$(C_{1-6}$ alkyl$)_2$, halogen, or carboxylic acid;

$R^2$ is $C_{1-6}$ alkyl, 6 to 10-membered aryl, O, or

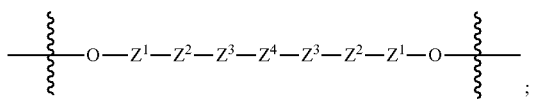

$Z^1$ is $C_{1-6}$ alkyl or 6 to 10-membered aryl;
$Z^2$ is O, O(C$=$O)O, or absent;
$Z^3$ is 6 to 10-membered aryl, 5 to 10-membered heteroaryl, or absent;
$Z^4$ is $C_{1-6}$ alkyl, 5 to 15-membered cycloalkyl, 5 to 15-membered heterocyclyl, 6 to 14-membered aryl, 5 to 15-membered heteroaryl, or (C$=$O)O-(6 to 10-membered aryl)-O(C$=$O), each of which are optionally substituted, independently for each occurrence, one, two, or three times with $C_{1-3}$ alkyl, $C_{1-3}$ haloalkyl, or halogen;
$R^3$ is $C_{1-6}$ alkyl, C($=$O)—$C_{1-6}$ alkyl, 6 to 10-membered aryl, 5 to 10-membered heteroaryl, $(C_{1-6}$ alkyl$)$-(6 to 10-membered aryl), $(C_{1-6}$ alkyl$)$-(5 to 10-membered heteroaryl), and 5 to 15-membered heterocyclyl, each of which is optionally substituted, independently for each occurrence, one, two, or three times, independently, with $C_{1-3}$ alkyl, $C_{1-3}$ alkoxy, $C_{1-3}$ haloalkyl, acetamide, carboxylic acid, silyl, hydroxyl, cyano, nitro, and halogen;
n is 25-250;
p is 1, 2, 3, or 4; and
wherein $R^1$, $R^2$, $R^3$, $Y^1$, $Y^2$, $Z^1$, $Z^2$, $Z^3$, and $Z^4$ are each, independently, the same for every occurrence in the polymer.

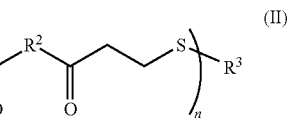

In an embodiment, $Y^2$ is branched $C_{3-6}$ alkyl, 6 to 10-membered aryl, biphenyl, 5 to 10-membered heteroaryl, $(CH_2CH_2O)_pCH_2CH_2$, C$=$N—$(C_{1-6}$ alkyl$)$-N$=$C, O, S, or $SO_2$, wherein the alkyl, aryl, biphenyl, and heteroaryl are optionally substituted, independently for each occurrence, one, two, or three times with $C_{1-6}$ alkyl, $C_{1-6}$ alkoxy, $C_{1-6}$ haloalkyl, $(C_{0-3}$ alkyl$)$-OH, $NH_2$, NH$(C_{1-6}$ alkyl$)$, N$(C_{1-6}$ alkyl$)_2$, halogen, or carboxylic acid.

In an embodiment, $Y^2$ is $C_{1-6}$ alkyl, 6 to 10-membered aryl, biphenyl 5 to 10-membered heteroaryl, C$=$N—$(C_{1-6}$ alkyl$)$-N$=$C, S, or $SO_2$, wherein the alkyl is substituted, independently for each occurrence, one, two, or three times with $C_{1-6}$ alkyl, $C_{1-6}$ alkoxy, $C_{1-6}$ haloalkyl, $(C_{0-3}$ alkyl$)$-OH, $NH_2$, NH$(C_{1-6}$ alkyl$)$, N$(C_{1-6}$ alkyl$)_2$, halogen, or carboxylic acid, and wherein the aryl, and heteroaryl are optionally substituted, independently for each occurrence, one, two, or three times with $C_{1-6}$ alkyl, $C_{1-6}$ alkoxy, $C_{1-6}$ haloalkyl, $(C_{0-3}$ alkyl$)$-OH, $NH_2$, NH$(C_{1-6}$ alkyl$)$, N$(C_{1-6}$ alkyl$)_2$, halogen, or carboxylic acid.

In an embodiment, $Y^2$ is $C_{1-6}$ alkyl, wherein alkyl is substituted one, two, or three times with $C_{1-6}$ alkyl, thereby forming a branched linker.

In an embodiment, $Y^2$ is 6 to 10-membered aryl, biphenyl 5 to 10-membered heteroaryl, C$=$N—$(C_{1-6}$ alkyl$)$-N$=$C, S, or $SO_2$, wherein the aryl and heteroaryl are optionally substituted, independently for each occurrence, one, two, or three times with $C_{1-6}$ alkyl, $C_{1-6}$ alkoxy, $C_{1-6}$ haloalkyl, $(C_{0-3}$ alkyl$)$-OH, $NH_2$, NH$(C_{1-6}$ alkyl$)$, N$(C_{1-6}$ alkyl$)_2$, halogen, or carboxylic acid.

In an embodiment, $R^2$ is branched $C_{3-6}$ alkyl, 6 to 10-membered aryl, O, or

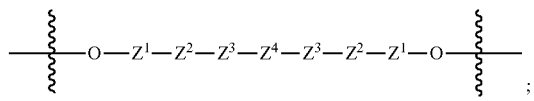

In an embodiment, $R^2$ is 6 to 10-membered aryl, O, or

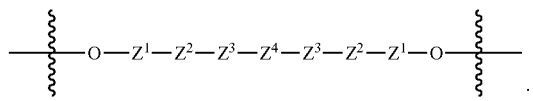

In an embodiment, $Z^1$ is branched $C_{3-6}$ alkyl or 6 to 10-membered aryl

In an embodiment, $Z^4$ is branched $C_{3-6}$ alkyl, 5 to 15-membered cycloalkyl, 5 to 15-membered heterocyclyl, 6 to 14-membered aryl, 5 to 15-membered heteroaryl, or (C$=$O)O-(6 to 10-membered aryl)-O(C$=$O), each of which are optionally substituted, independently for each occurrence, one, two, or three times with $C_{1-3}$ alkyl, $C_{1-3}$ haloalkyl, or halogen.

In preferred embodiments of Formula (II), $R^1$, $R^2$, $R^3$, $Y^1$, $Y^2$, $Z^1$, $Z^2$, $Z^3$, and $Z^4$ are each, independently, the same for every occurrence in the polymer. For instance, in a polymer wherein $Y^1$ is selected to be absent and $Y^2$ is selected to be butyl, $Y^1$ must be absent for every occurrence of $Y^1$ and $Y^2$ must be butyl for every occurrence of $Y^2$. By way of further example, every time variable $R^1$ appears in a given polymer of Formula (II), it represents a conserved group, wherein each of $Y^1$ and $Y^2$ are consistently and respectively selected to be the same for every occurrence within the polymer.

In an embodiment, $Y^1$ is absent, and $Y^2$ is 5 to 10-membered heteroaryl.

In an embodiment, $Y^1$ is $C_{1-3}$ alkyl, and $Y^2$ is 6 to 10-membered aryl, optionally substituted one, two, or three times with $C_{1-6}$ alkyl.

In an embodiment, $Y^1$ is absent, and $Y^2$ is $C_{1-6}$ alkyl.

In an embodiment, $Y^1$ is absent, and $Y^2$ is branched $C_{1-6}$ alkyl.

In an embodiment, $Y^1$ is absent, and $Y^2$ is $C_{1-6}$ alkyl substituted one, two, or three times with $C_{1-6}$ alkyl, thereby forming a branched linker.

In an embodiment, $Y^1$ is absent, and $Y^2$ is $C_{1-6}$ alkyl substituted, independently for each occurrence, one, two, or three times with $C_{1-6}$ alkyl, $C_{1-6}$ alkoxy, $C_{1-6}$ haloalkyl, ($C_{0-3}$ alkyl)-OH, $NH_2$, $NH(C_{1-6}$ alkyl), $N(C_{1-6}$ alkyl)$_2$, halogen, or carboxylic acid.

In an embodiment, $Y^1$ is absent, and $Y^2$ is propyl.
In an embodiment, $Y^1$ is absent, and $Y^2$ is butyl.
In an embodiment, $Y^1$ is absent, and $Y^2$ is pentyl.
In an embodiment, $Y^1$ is absent, and $Y^2$ is hexyl.
In an embodiment, $Y^1$ is absent, and $Y^2$ is $(CH_2CH_2O)_pCH_2CH_2$.

In an embodiment, $Y^1$ is absent, and $Y^2$ is $C_{1-6}$ alkyl substituted with ($C_{0-3}$ alkyl)-OH.

In an embodiment, $Y^1$ is $C_{1-3}$ alkyl, and $Y^2$ is S.

In an embodiment, $Y^1$ is absent, and $Y^2$ is 6 to 10-membered aryl, optionally substituted one, two, or three times with $C_{1-6}$ alkyl.

In an embodiment, $Y^1$ is 5 to 10-membered heteroaryl, optionally substituted, independently for each occurrence, one, two, or three times with $C_{1-3}$ alkyl, $C_{1-3}$ alkoxy, $C_{1-3}$ haloalkyl, halogen, or 6 to 10-membered aryl, and $Y^2$ is C=N—($C_{1-6}$ alkyl)-N=C.

In an embodiment, $Y^1$ is absent, and $Y^2$ is 5 to 10-membered heteroaryl optionally substituted, independently for each occurrence, one, two, or three times with $C_{1-6}$ alkyl, $C_{1-6}$ alkoxy, $C_{1-6}$ haloalkyl, ($C_{0-3}$ alkyl)-OH, $NH_2$, $NH(C_{1-6}$ alkyl), $N(C_{1-6}$ alkyl)$_2$, halogen, or carboxylic acid.

In an embodiment, $Y^1$ is ($C_{1-6}$ alkyl)-NHC(=O), and $Y^2$ is 6 to 10-membered aryl.

In an embodiment, $Y^1$ is C=O, and $Y^2$ is 6 to 10-membered aryl.

In an embodiment, $Y^1$ is $C_{1-3}$ alkyl, and $Y^2$ is $SO_2$.
In an embodiment, $Y^1$ is absent, and $Y^2$ is biphenyl.
In an embodiment, $R^2$ is $C_{1-6}$ alkyl.
In an embodiment, $R^2$ is propyl.
In an embodiment, $R^2$ is butyl.
In an embodiment, $R^2$ is pentyl.
In an embodiment, $R^2$ is hexyl.
In an embodiment, $R^2$ is branched $C_{3-6}$ alkyl.
In an embodiment, $R^2$ is 1-methypropyl.
In an embodiment, $R^2$ is neopentyl.
In an embodiment, $R^2$ is 6 to 10-membered aryl.
In an embodiment, $R^2$ is O.
In an embodiment, $R^2$ is In an embodiment, $Z^1$ is $C_{1-6}$ alkyl, $Z^2$ is O, $Z^3$ is 6 to 10-membered aryl, and $Z^4$ is 6 to 14-membered aryl.

In an embodiment, $Z^1$ is $C_{1-6}$ alkyl, $Z^2$ is O, $Z^3$ is 6 to 10-membered aryl, and $Z^4$ is 5 to 15-membered cycloalkyl.

In an embodiment, $Z^1$ is $C_{1-6}$ alkyl, $Z^2$ is O, $Z^3$ is 6 to 10-membered aryl, and $Z^4$ is $C_{1-6}$ alkyl.

In an embodiment, $Z^1$ is $C_{1-6}$ alkyl, $Z^2$ is O, $Z^3$ is absent, and $Z^4$ is $C_{1-6}$ alkyl.

In an embodiment, $Z^1$ is $C_{1-6}$ alkyl, $Z^2$ is absent, $Z^3$ is absent, and $Z^4$ is 5 to 15-membered cycloalkyl.

In an embodiment, $Z^1$ is 6 to 10-membered aryl, $Z^2$ is absent, $Z^3$ is absent, and $Z^4$ is $C_{1-6}$ alkyl optionally substituted, independently for each occurrence, one, two, or three times with $C_{1-3}$ alkyl, $C_{1-3}$ haloalkyl, or halogen.

In an embodiment, $Z^1$ is $C_{1-6}$ alkyl, $Z^2$ is O, $Z^3$ is absent, and $Z^4$ is $C_{1-6}$ alkyl.

In an embodiment, $Z^1$ is branched $C_{3-6}$ alkyl, $Z^2$ is O, $Z^3$ is absent, and $Z^4$ is branched $C_{3-6}$ alkyl.

In an embodiment, $Z^1$ is $C_{1-6}$ alkyl, $Z^2$ is O, $Z^3$ is absent, and $Z^4$ is $C_{1-6}$ alkyl.

In an embodiment, $Z^1$ is $C_{1-6}$ alkyl, $Z^2$ is O(C=O)O, $Z^3$ is 6 to 10-membered aryl, and $Z^4$ is (C=O)O-(6 to 10-membered aryl)-O(C=O) optionally substituted, independently for each occurrence, one, two, or three times with $C_{1-3}$ alkyl, $C_{1-3}$ haloalkyl, or halogen.

In an embodiment, $R^3$ is ($C_{1-6}$ alkyl)-(6 to 10-membered aryl) optionally substituted, independently for each occurrence, one, two, or three times with $C_{1-3}$ alkyl, $C_{1-3}$ alkoxy, $C_{1-3}$ haloalkyl, acetamide, carboxylic acid, silyl, hydroxyl, cyano, nitro, and halogen.

In an embodiment, $R^3$ is $CH_2$-(6 to 10-membered aryl) optionally substituted, independently for each occurrence, one, two, or three times with $C_{1-3}$ alkyl, $C_{1-3}$ alkoxy, $C_{1-3}$ haloalkyl, acetamide, carboxylic acid, silyl, hydroxyl, cyano, nitro, and halogen.

In an embodiment, $R^3$ is $C_{1-6}$ alkyl optionally substituted, independently for each occurrence, one, two, or three times with $C_{1-3}$ alkyl, $C_{1-3}$ alkoxy, $C_{1-3}$ haloalkyl, acetamide, carboxylic acid, silyl, hydroxyl, cyano, nitro, and halogen.

In an embodiment, $R^3$ is $C_{1-6}$ alkyl optionally substituted, independently for each occurrence, one, two, or three times with acetamide and carboxylic acid.

In an embodiment, $R^3$ is $C_{1-6}$ alkyl optionally substituted, independently for each occurrence, one, two, or three times with silyl.

In an embodiment, $R^3$ is C(=O)—$C_{1-6}$ alkyl.
In an embodiment, $R^3$ is 5 to 15-membered heterocyclyl.
In an embodiment, $R^3$ is 5 to 10-membered heteroaryl optionally substituted, independently for each occurrence, one, two, or three times with $C_{1-3}$ alkyl, $C_{1-3}$ alkoxy, $C_{1-3}$ haloalkyl, acetamide, carboxylic acid, silyl, hydroxyl, cyano, nitro, and halogen.

In an embodiment, $R^3$ is 5 to 10-membered heteroaryl optionally substituted, independently for each occurrence, one, two, or three times with $C_{1-3}$ haloalkyl, carboxylic acid, and hydroxyl.

In some embodiments of the polymer of Formula (II), $R^1$ has a structure of one of the following:

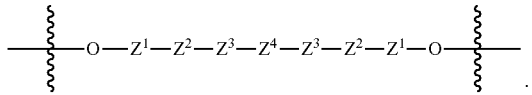 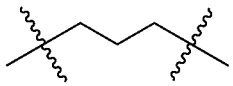

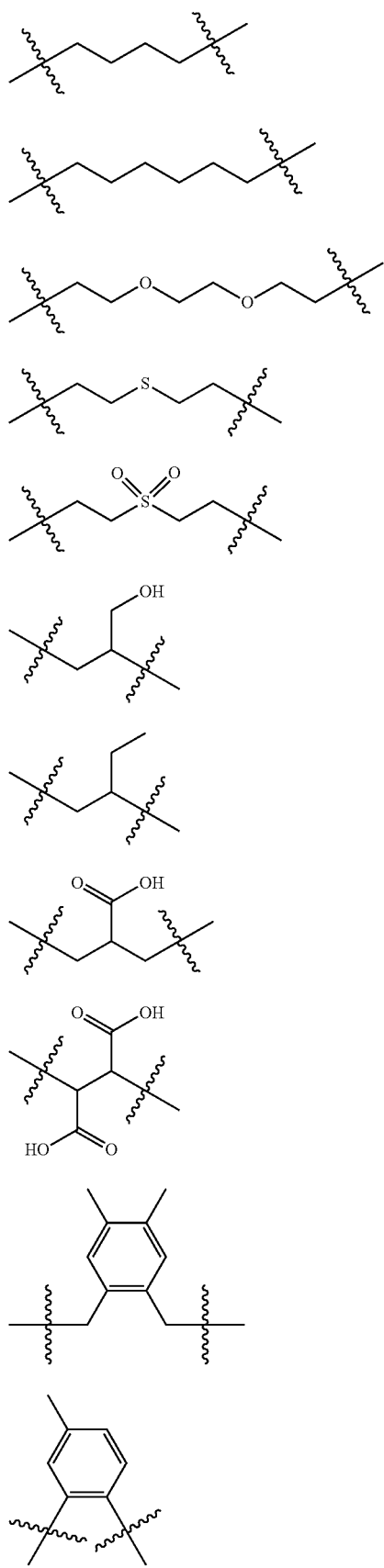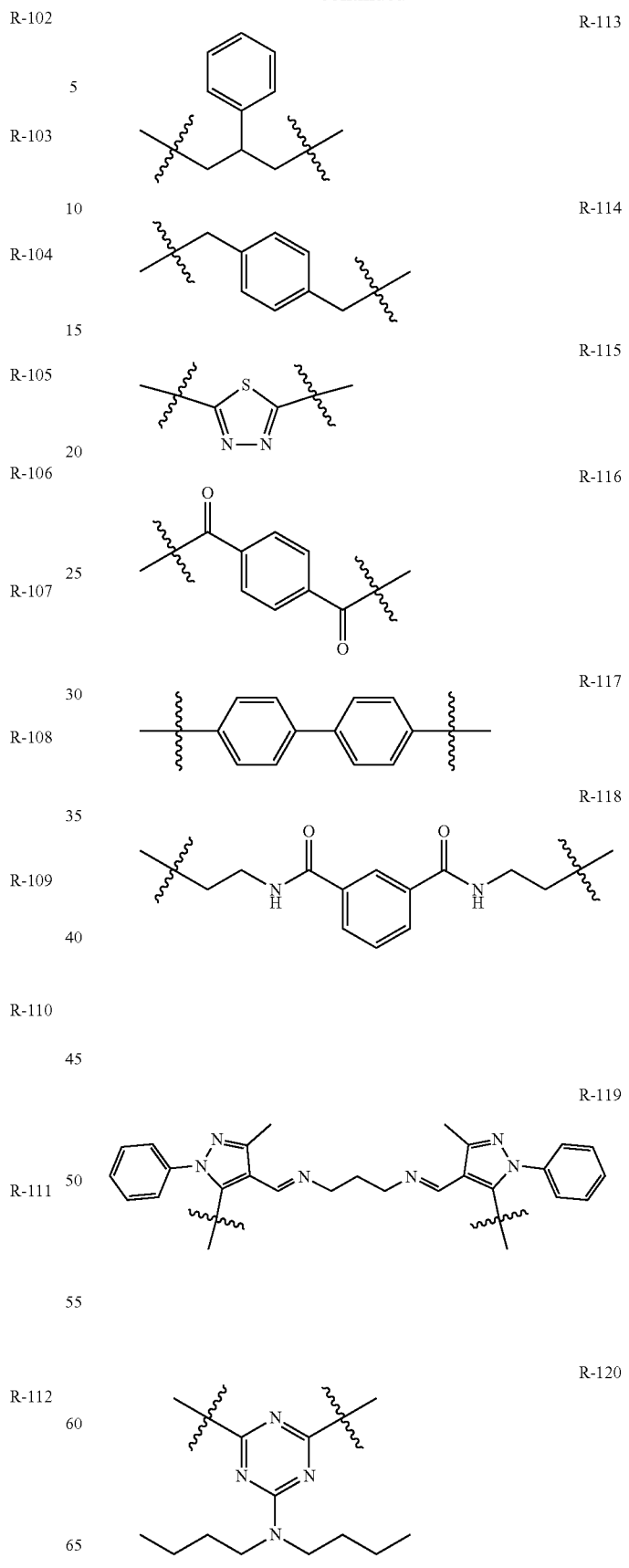

In some embodiments of the polymer of Formula (II), $R^2$ has a structure of one of the following:
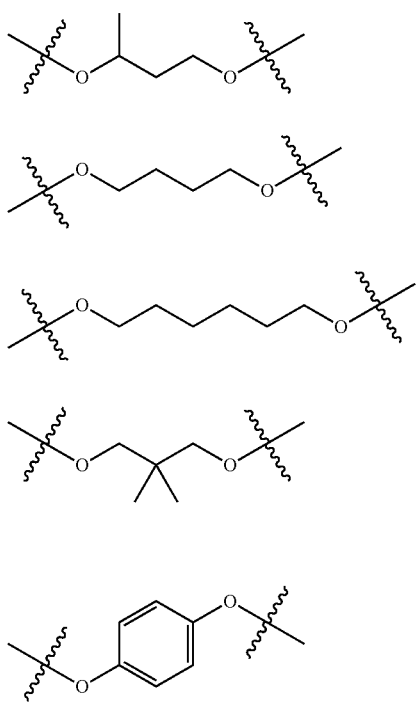
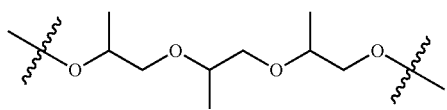
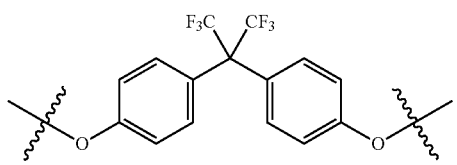

-continued
R-216
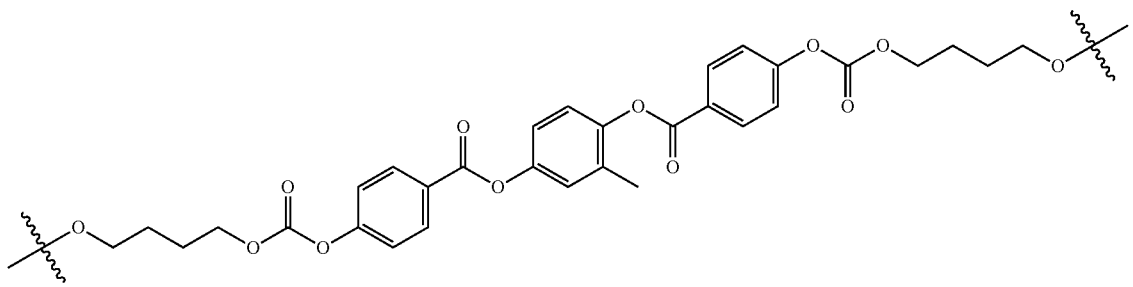
R-217
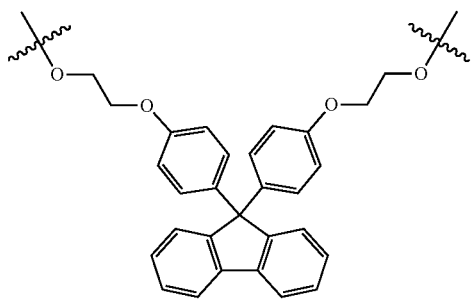
In some embodiments of the polymer of Formula (II), $R^3$ has a structure of one of the following:
R-301
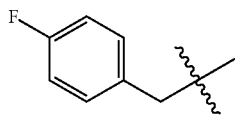
R-302
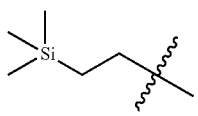
R-303
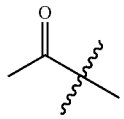
R-304
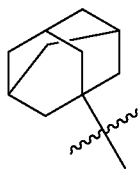
R-305
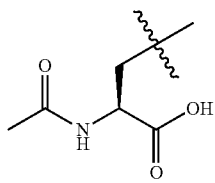
-continued
R-306
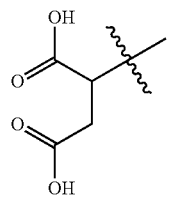
R-307
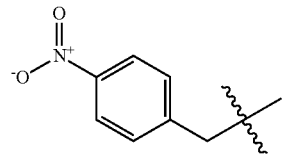
R-308
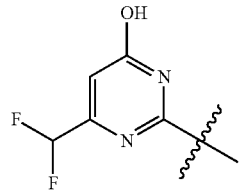
R-309
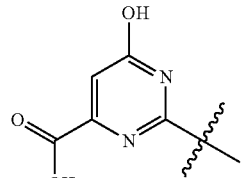
Non-limiting illustrative compounds of Formula (II) are exemplified in Table 2.

TABLE 2

| Peptide Identifier | $R^1$ | $R^2$ | $R^3$ |
|---|---|---|---|
| B1 | R-113 | R-202 | R-301 |
| B2 | R-105 | R-202 | R-301 |
| B3 | R-104 | R-202 | R-301 |
| B4 | R-103 | R-202 | R-301 |
| B5 | R-113 | R-211 | R-301 |
| B6 | R-105 | R-211 | R-301 |
| B7 | R-104 | R-211 | R-301 |
| B8 | R-103 | R-211 | R-301 |
| B9 | R-113 | R-201 | R-301 |
| B10 | R-105 | R-201 | R-301 |
| B11 | R-104 | R-201 | R-301 |
| B12 | R-103 | R-201 | R-301 |
| B13 | R-101 | R-202 | R-305 |
| B14 | R-107 | R-202 | R-305 |
| B15 | R-102 | R-202 | R-305 |
| B16 | R-101 | R-211 | R-305 |
| B17 | R-107 | R-211 | R-305 |
| B18 | R-102 | R-211 | R-305 |
| B19 | R-101 | R-201 | R-305 |
| B20 | R-107 | R-201 | R-305 |
| B21 | R-102 | R-201 | R-305 |
| B22 | R-101 | R-217 | R-301 |
| B23 | R-107 | R-217 | R-301 |
| B24 | R-102 | R-217 | R-301 |
| B25 | R-104 | R-217 | R-301 |
| B26 | R-105 | R-217 | R-301 |
| B27 | R-115 | R-201 | R-305 |
| B28 | R-115 | R-205 | R-305 |
| B29 | R-115 | R-211 | R-305 |
| B30 | R-115 | R-207 | R-305 |
| B31 | R-115 | R-214 | R-305 |
| B32 | R-111 | R-209 | R-303 |
| B33 | R-115 | R-213 | R-302 |
| B34 | R-115 | R-213 | R-303 |
| B35 | R-106 | R-213 | R-303 |
| B36 | R-106 | R-213 | R-307 |
| B37 | R-106 | R-213 | R-302 |
| B38 | R-106 | R-215 | R-301 |
| B39 | R-106 | R-215 | R-303 |
| B40 | R-106 | R-215 | R-302 |
| B41 | R-106 | R-215 | R-307 |
| B42 | R-106 | R-215 | R-308 |
| B43 | R-118 | R-216 | R-302 |
| B44 | R-118 | R-216 | R-303 |
| B45 | R-119 | R-217 | R-301 |
| B46 | R-118 | R-216 | R-307 |
| B47 | R-118 | R-216 | R-301 |
| B48 | R-119 | R-217 | R-303 |
| B49 | R-119 | R-217 | R-307 |
| B50 | R-119 | R-217 | R-302 |
| B51 | R-119 | R-217 | R-308 |
| B52 | R-111 | R-209 | R-308 |
| B53 | R-106 | R-213 | R-301 |
| B54 | R-115 | R-213 | R-308 |
| B55 | R-110 | R-209 | R-308 |
| B56 | R-117 | R-212 | R-303 |
| B57 | R-116 | R-208 | R-303 |
| B58 | R-107 | R-208 | R-303 |
| B59 | R-114 | R-211 | R-305 |
| B60 | R-111 | R-205 | R-306 |
| B61 | R-109 | R-211 | R-305 |
| B62 | R-111 | R-205 | R-305 |
| B63 | R-101 | R-211 | R-306 |
| B64 | R-107 | R-208 | R-302 |
| B65 | R-107 | R-207 | R-303 |
| B66 | R-111 | R-205 | R-308 |
| B67 | R-111 | R-203 | R-301 |
| B68 | R-120 | R-208 | R-306 |
| B69 | R-108 | R-206 | R-303 |
| B70 | R-109 | R-211 | R-301 |
| B71 | R-107 | R-207 | R-301 |
| B72 | R-111 | R-205 | R-301 |
| B73 | R-111 | R-203 | R-309 |
| B74 | R-111 | R-203 | R-307 |
| B75 | R-108 | R-207 | R-301 |
| B76 | R-116 | R-211 | R-307 |
| B77 | R-107 | R-207 | R-305 |
| B78 | R-111 | R-209 | R-302 |
| B79 | R-108 | R-212 | R-305 |
| B80 | R-111 | R-215 | R-305 |
| B81 | R-108 | R-201 | R-305 |
| B82 | R-107 | R-208 | R-305 |
| B83 | R-114 | R-211 | R-303 |
| B84 | R-112 | R-201 | R-301 |

A preferred polymer of the disclosure is B18, wherein $R^1$ is R-102, $R^2$ is R-211, and $R^3$ is R-305.

A third aspect of the disclosure relates to compounds of Formula (III):

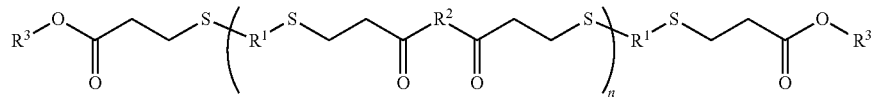

or a pharmaceutically acceptable salt thereof, wherein, $R^1$ is

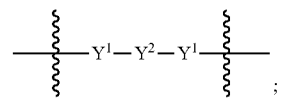

$Y^1$ is $C_{1-3}$ alkyl, $(C_{1-6}$ alkyl)-NHC(=O), C=O, 5 to 10-membered heteroaryl, or absent, wherein heteroaryl is optionally substituted, independently for each occurrence, one, two, or three times with $C_{1-3}$ alkyl, $C_{1-3}$ alkoxy, $C_{1-3}$ haloalkyl, halogen, or 6 to 10-membered aryl;

$Y^2$ is $C_{1-6}$ alkyl, 6 to 10-membered aryl, biphenyl, 5 to 10-membered heteroaryl, $(CH_2CH_2O)_pCH_2CH_2$, C=N—($C_{1-6}$ alkyl)-N=C, O, S, or $SO_2$, wherein the alkyl, aryl, biphenyl, and heteroaryl are optionally substituted, independently for each occurrence, one, two, or three times with $C_{1-6}$ alkyl, $C_{1-6}$ alkoxy, $C_{1-6}$ haloalkyl, ($C_{0-3}$ alkyl)-OH, $NH_2$, $NH(C_{1-6}$ alkyl), $N(C_{1-6}$ alkyl)$_2$, halogen, or carboxylic acid;

$R^2$ is $C_{1-6}$ alkyl, 6 to 10-membered aryl, O, or

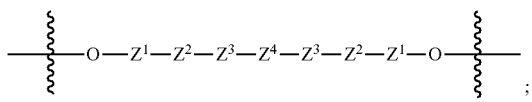

;

$Z^1$ is $C_{1-6}$ alkyl or 6 to 10-membered aryl;

$Z^2$ is O, O(C=O)O, or absent;

$Z^3$ is 6 to 10-membered aryl, 5 to 10-membered heteroaryl, or absent;

$Z^4$ is $C_{1-6}$ alkyl, 5 to 15-membered cycloalkyl, 5 to 15-membered heterocyclyl, 6 to 14-membered aryl, 5 to 15-membered heteroaryl, or (C=O)O-(6 to 10-membered aryl)-O(C=O), each of which are optionally substituted, independently for each occurrence, one, two, or three times with $C_{1-3}$ alkyl, $C_{1-3}$ haloalkyl, or halogen;

n is 25-250;

p is 1, 2, 3, or 4; and wherein $R^1$, $R^2$, $Y^1$, $Y^2$, $Z^1$, $Z^2$, $Z^3$, and $Z^4$ are each, independently, the same for every occurrence in the polymer.

The polymers of Formulae (I), (II), and (III), as well as the polymers of Tables 1 and 2 are also referred to herein as "polymers of the disclosure."

Polymers of the disclosure may have a molecular weight ranging from about 1000 Da to about 100000 Da.

The disclosure includes all tautomers and optical isomers (e.g., enantiomers, diastereomers, diastereomeric mixtures, racemic mixtures, and the like) of the polymers of the disclosure.

In another aspect, the present disclosure relates to a population of nanoparticles. The polymeric nanoparticles of the disclosure comprise one or more polymers of the disclosure and an additional polymer.

Ideally, the additional polymer is biodegradable. Example additional polymers of the polymeric nanoparticles of the disclosure include polylactic acid (PLA), poly-L-lysine (PLL), polyglutamic acid (PGluA), polyglycolic acid (PGA), polyethylene glycol (PEG), polycaprolactone (PCL), polyaspartate (PAA), poly(D,L-lactide-co-glycolic) acid (PLGA), cyclodextrins (CD), N-(2-hydroxypropyl)-methacrylamide copolymer (HPMA), and copolymers thereof. An exemplary copolymer is PLGA-PEG.

In an embodiment, the polymeric nanoparticles comprise a polymer of Formula (I), (II), or (III) and an additional polymer. In another embodiment, the polymeric nanoparticles comprise a polymer of Formula (I), (II), or (III) and an additional polymer, wherein the additional polymer is a copolymer. In yet another embodiment, the polymeric nanoparticles comprise a polymer of Formula (I), (II), or (III) and PLGA-PEG.

In an embodiment, the polymeric nanoparticles comprise a polymer of Formula (I) and an additional polymer. In another embodiment, the polymeric nanoparticles comprise a polymer of Formula (I) and an additional polymer, wherein the additional polymer is a copolymer. In yet embodiment, the polymeric nanoparticles comprise a polymer of Formula (I) and PLGA-PEG. In still another embodiment, the polymeric nanoparticles comprise a polymer selected from the group consisting of A1-A80 and PLGA-PEG.

In an embodiment, the polymeric nanoparticles comprise a polymer of Formula (II) and an additional polymer. In another embodiment, the polymeric nanoparticles comprise a polymer of Formula (II) and an additional polymer, wherein the additional polymer is a copolymer. In yet embodiment, the polymeric nanoparticles comprise a polymer of Formula (II) and PLGA-PEG. In still another embodiment, the polymeric nanoparticles comprise a polymer selected from the group consisting of B1-B84 and PLGA-PEG.

In an embodiment, the polymeric nanoparticles comprise a polymer of Formula (III) and an additional polymer. In another embodiment, the polymeric nanoparticles comprise a polymer of Formula (III) and an additional polymer, wherein the additional polymer is a copolymer. In yet embodiment, the polymeric nanoparticles comprise a polymer of Formula (III) and PLGA-PEG.

Polymeric nanoparticles of the disclosure may have particle sizes ranging from about 20 nm to about 200 nm; from about 30 nm to about 190 nm; from about 40 nm to about 180 nm; from about 50 nm to about 170 nm; and more preferably from about 60 nm to about 160 nm.

Nanoparticles comprising one or more polymers of Formulae (I), (II), and (III), as well as nanoparticles comprising polymers of Tables 1 and 2 are referred to herein as "nanoparticles of the disclosure" or "polymeric nanoparticles of the disclosure."

Compositions and Combinations

In another aspect, the present disclosure relates to pharmaceutical compositions comprising a polymer of the disclosure, or a pharmaceutically acceptable salt thereof, and a pharmaceutically acceptable carrier. The present disclosure also relates to pharmaceutical compositions comprising a population of nanoparticles of the disclosure and a pharmaceutically acceptable carrier.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound provided herein within or to a patient such that it can perform its intended function. Typically, such constructs are carried or transported from one organ, or portion of the body, to another organ, or portion of the body. Each carrier must be "acceptable" in the sense of being compatible with the other ingredients of the formulation, including the polymer of polymeric nanoparticles provided herein, and not injurious to the patient. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol;

phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound provided herein, and are physiologically acceptable to the patient. Other additional ingredients that can be included in the pharmaceutical compositions provided herein are known in the art and described, for example in Remington's Pharmaceutical Sciences (Genaro, Ed., Mack Publishing Co., 1985, Easton, PA), which is incorporated herein by reference.

A "pharmaceutically acceptable excipient" refers to a substance that is biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols. Pharmaceutically acceptable excipients for use in vaccines are known in the art and include, by non-limiting example, monosodium glutamate, sucrose, mannose, fructose, dextrose, human serum albumin, potassium phosphate, lactose, cellulose, magnesium stearate, alcohol, acetone, castor oil, aluminum hydroxide, sodium chloride, benzethonium chloride, formaldehyde, glycerin, asparagine, citric acid, aluminum phosphate, Tween 80, Tween 20, histidine, and ammonium sulfate.

Delivery forms of the pharmaceutical compositions containing one or more dosage units of the polymers or polymeric nanoparticles may be prepared using suitable pharmaceutical excipients and compounding techniques known or that become available to those skilled in the art. The compositions may be administered in the inventive methods by a suitable route of delivery, e.g., oral, aerosol, parenteral, ophthalmic, pulmonary, and topical administration. Preferably, the polymers and polymeric nanoparticles of the disclosure are administered parenterally.

For parenteral use, including intravenous, intramuscular, intraperitoneal, or subcutaneous routes, the polymers and polymeric nanoparticles of the disclosure may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

The polymers or polymeric nanoparticles may be administered, by nonlimiting example, in the form of a vaccine, a capsule or tablet, a suppository, or an implant. Preferably, the polymers and nanoparticles disclosed herein are administered in the form of a vaccine.

In another aspect, provided herein are pharmaceutical combinations comprising a polymer or population of nanoparticles of the disclosure and a second agent as a combined preparation for simultaneous, separate, or sequential use in the prevention or treatment of cancer, an infectious disease, or an autoimmune disorder in a subject in need thereof.

Certain properties of the polymeric nanoparticles of the disclosure allow them to act as adjuvants in vaccines. For example, the nanoparticles of the disclosure can effectively deliver adsorbed antigen to immune cells. Moreover, the polymers of the disclosure, of which the polymeric nanoparticles are comprised, have an intrinsic immune-stimulating effect. Accordingly, in a preferred embodiment, the disclosure relates to a vaccine comprising an adjuvant and an antigen, wherein the adjuvant is a polymer or a population of polymeric nanoparticles of the disclosure. In some embodiments, the antigen is a peptide antigen. In some embodiments, the antigen is a fragment of mutated KIF18B protein. In some embodiments, the antigen is a fragment of mutated KIF18B protein specific to B16/F10 cells. In some embodiments, the antigen is OVA257-264 peptide.

In some embodiments, the disclosure relates to a vaccine comprising an adjuvant and an antigen, wherein the adjuvant is a population of polymeric nanoparticles comprising a polymer of Formula (I). In some embodiments, the vaccine comprises an adjuvant and an antigen, wherein the adjuvant is a population of polymeric nanoparticles comprising a polymer selected from the group consisting of A1-A80. In some embodiments, the adjuvant is a population of polymeric nanoparticles comprising a polymer of Formula (I), and the antigen is a peptide antigen. In some embodiments, the adjuvant is a population of polymeric nanoparticles comprising a polymer selected from the group consisting of A1-A80, and the antigen is a peptide antigen. In some embodiments, the adjuvant is a population of polymeric nanoparticles comprising a polymer of Formula (I), and the antigen is a fragment of mutated KIF18B protein. In some embodiments, the adjuvant is a population of polymeric nanoparticles comprising a polymer selected from the group consisting of A1-A80, and the antigen is a fragment of mutated KIF18B protein. In some embodiments the adjuvant is a population of polymeric nanoparticles comprising a polymer of Formula (I), and the antigen is a fragment of mutated KIF18B protein specific to B16/F10 cells. In some embodiments, the adjuvant is a population of polymeric nanoparticles comprising a polymer selected from the group consisting of A1-A80, and the antigen is a fragment of mutated KIF18B protein specific to B16/F10 cells. In some embodiments, the adjuvant is a population of polymeric nanoparticles comprising a polymer of Formula (I), and the antigen is OVA257-264 peptide. In some embodiments, the adjuvant is a population of polymeric nanoparticles comprising a polymer selected from the group consisting of A1-A80, and the antigen is OVA257-264 peptide.

In some embodiments, the disclosure relates to a vaccine comprising an adjuvant and an antigen, wherein the adjuvant is a population of polymeric nanoparticles comprising a polymer of Formula (II). In some embodiments, the vaccine comprises an adjuvant and an antigen, wherein the adjuvant is a population of polymeric nanoparticles comprising a polymer selected from the group consisting of B1-B84. In some embodiments, the adjuvant is a population of polymeric nanoparticles comprising a polymer of Formula (II), and the antigen is a peptide antigen. In some embodiments, the adjuvant is a population of polymeric nanoparticles comprising a polymer selected from the group consisting of B1-B84, and the antigen is a peptide antigen. In some embodiments, the adjuvant is a population of polymeric nanoparticles comprising a polymer of Formula (II), and the antigen is a fragment of mutated KIF18B protein. In some embodiments, the adjuvant is a population of polymeric nanoparticles comprising a polymer selected from the group consisting of B1-B84, and the antigen is a fragment of mutated KIF18B protein. In some embodiments the adjuvant is a population of polymeric nanoparticles comprising a polymer of Formula (II), and the antigen is a fragment of mutated KIF18B protein specific to B16/F10 cells. In some embodiments, the adjuvant is a population of polymeric nanoparticles comprising a polymer selected from the group consisting of B1-B84, and the antigen is a fragment of mutated KIF18B protein specific to B16/F10 cells. In some embodiments, the adjuvant is a population of polymeric nanoparticles comprising a polymer of Formula (II), and the antigen is OVA257-264 peptide. In some embodiments, the adjuvant is a population of polymeric nanoparticles comprising a polymer selected from the group consisting of B1-B84, and the antigen is OVA257-264 peptide.

In some embodiments, the disclosure relates to a vaccine comprising an adjuvant and an antigen, wherein the adjuvant is a population of polymeric nanoparticles comprising a polymer of Formula (III). In some embodiments, the adjuvant is a population of polymeric nanoparticles comprising a polymer of Formula (III), and the antigen is a peptide antigen. In some embodiments, the adjuvant is a population of polymeric nanoparticles comprising a polymer of Formula (III), and the antigen is a fragment of mutated KIF18B protein. In some embodiments the adjuvant is a population of polymeric nanoparticles comprising a polymer of Formula (III), and the antigen is a fragment of mutated KIF18B protein specific to B16/F10 cells. In some embodiments, the adjuvant is a population of polymeric nanoparticles comprising a polymer of Formula (III), and the antigen is OVA257-264 peptide.

In another aspect, the polymers and polymeric nanoparticles of the disclosure may be co-administered with a second agent that is an anti-cancer agent. Example anti-cancer agents include chemotherapeutic agents, cytotoxic agents, radio-therapeutic agents, anti-neoplastic agents, and anti-proliferative agents.

Methods of Using the Polymers and Nanoparticles of the Disclosure

The disclosure also provides therapeutic methods, which include administering to a subject a polymer or a population of nanoparticles of the disclosure.

In an aspect the disclosure relates to a polymer or a population of nanoparticles of the disclosure for use as a medicament.

In another aspect, the disclosure relates to a method of treating cancer by administering a polymer or a population of nanoparticles of the disclosure to a subject in need thereof. The term "cancer" refers to a condition characterized by the proliferation of malignant neoplastic cells, such as tumors, neoplasms, carcinomas, sarcomas, leukemias, lymphomas and the like.

The term "cancer" includes, but is not limited to, the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, colorectal, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colonrectum, large intestine, rectum, brain and central nervous system, chronic myeloid leukemia (CML), and leukemia.

In an embodiment, the polymers or polymeric nanoparticles of the disclosure may be administered to a subject in need thereof for the treatment of breast cancer, lung cancer, prostate cancer, colorectal cancer, skin cancer (e.g., melanoma), bladder cancer, non-Hodgkin's lymphoma, kidney cancer (e.g., renal cell carcinoma), uterine cancer (e.g., endometrial cancer), leukemia, pancreatic cancer, thyroid cancer, and liver cancer (e.g., hepatocellular carcinoma).

In an embodiment, the polymers or polymeric nanoparticles of the disclosure may be administered to a subject for the treatment of skin cancer. In a preferred embodiment, the polymers or polymeric nanoparticles may be administered for the treatment of melanoma.

In another aspect, the disclosure relates to a method of treating or preventing an infectious disease by administering a polymer or a population of nanoparticles of the disclosure to a subject in need thereof. Infectious diseases that can be treated or prevented by the polymers and polymeric nanoparticles of the disclosure are caused by infectious agents, including but not limited to bacteria, fungi, or viruses. Thus, in embodiments of this aspect of the disclosure, the polymers and polymeric nanoparticles are useful in the prevention or treatment of a bacterial, viral, or fungal infectious disease. Preferably, the polymers and polymeric nanoparticles of the disclosure are useful in the treatment or prevention of a viral infection.

By nonlimiting example, viral infections that may be treated or prevented by the polymers or polymeric nanoparticles of the disclosure include hepatitis virus (e.g., hepatitis A, hepatitis B, hepatitis C, hepatitis D), influenza, varicella, adenovirus, herpes virus (e.g., HSV-1, HSV-II), rinderpest, rhinovirus, echovirus, rotavirus, respiratory syncytial virus, papillomavirus, papova virus, cytomegalovirus, echinovirus, arbovirus, huntvirus, coxsackie virus, mumps virus, measles virus, rubella virus, polio virus, small pox, Epstein Barr virus, human immunodeficiency virus (HIV), and agents of viral diseases such as viral meningitis, encephalitis, dengue, and small pox.

Exemplary fungal infections which may be treated using the polymers or polymeric nanoparticles of the disclosure include, but are not limited to, aspergillosis, blastomycosis, candidiasis, coccidioidomycosis, cryptococcosis, histoplasmosis, mucormycosis, paracoccidioidomycosis, and sporotrichosis.

In another aspect, the disclosure relates to a method of treating an autoimmune disorder by administering a polymer or a population of nanoparticles of the disclosure to a subject in need thereof. Nonlimiting examples of autoimmune disorders treatable by the materials of the disclosure include multiple sclerosis, rheumatoid arthritis, stomatitis, Crohn's disease, and lupus erythematosus.

In another aspect, the disclosure relates to a method of modulating the immune system of a subject, comprising administering to the subject a polymer or a population of polymeric nanoparticles of the disclosure. Modulation of the immune system may, for example, be accomplished by upregulation or downregulation of the activity of dendritic cells. For example, the polymers or polymeric nanoparticles of the disclosure may, though contacting one or more dendritic cells, stimulate an immune activation pathway through upregulation of one or more immunoregulatory genes (e.g., MHCI, MHCII, CD40, CD80, and CD86). By further example, the polymers or polymeric nanoparticles of the disclosure may, by contacting one or more dendritic cells, stimulate the production of T cells.

In another aspect, the disclosure relates to a method of increasing expression of CD86, CD80, and/or CD40 in a subject in need thereof, the method comprising administering to the subject a polymer or a population of polymeric nanoparticles of the disclosure. In some embodiments, the disclosure relates to a method of increasing expression of CD86. In some embodiments, the disclosure relates to a method of increasing expression of CD80. In some embodiments, the disclosure relates to a method of increasing expression of CD40. In some embodiments, the increased expression occurs in dendritic cells.

In another aspect, the disclosure related to a method of increasing cross-presentation of antigen in a subject in need thereof, the method comprising administering to the subject a polymer or a population of polymeric nanoparticles of the disclosure. In some embodiments, the increased cross-presentation of antigen occurs in dendritic cells. In some embodiments, the increased cross-presentation occurs through increased cell surface presentation of antigen in an MHCI molecule on the surface cells. In some embodiments, the cells with increased presentation of antigen in an MHCI molecule on their surface are dendritic cells.

In another aspect, the disclosure relates to a method of increasing the levels interferon-γ in a subject in need thereof, the method comprising administering to the subject a polymer or a population of polymeric nanoparticles of the disclosure. In an embodiment, the levels of interferon-γ are increased in the subject's spleen. In an embodiment, the levels of interferon-γ are increased in CD8+ T cells.

In another aspect, the disclosure relates to a method of increasing the fraction of antigen-specific CD8+ T cells in a subject in need thereof, the method comprising administering to the subject a polymer or a population of polymeric nanoparticles of the disclosure. In an embodiment, the CD8+ T cells are specific to the antigen SIINFEKL. In an embodiment, the fraction of antigen-specific CD8+ T cells is increased in the subject's spleen.

In some embodiments of the above methods, the subject is a cancer patient. In some embodiments, the cancer patient is being administered a checkpoint inhibitor therapy. In some embodiments, the cancer patient lacks CD8+ cytotoxic T lymphocytes.

Methods of Making the Polymers and Polymeric Nanoparticles of the Disclosure

The disclosure also provides methods of synthesizing the polymers and the polymeric nanoparticles of the disclosure.

In one aspect, the disclosure relates to a method of synthesizing a polymer of the disclosure. In an embodiment, the method comprises selecting a dithiol and a diacrylate.

In an embodiment, the method further comprises reacting the dithiol and the diacrylate with triethylamine to produce a polymer. The reaction may be performed in solvent or under solventless conditions. Exemplary solvents for the synthesis of the polymer include THF, pyrimidine, dichloromethane, DMF, and DMSO. Preferably, the synthesis is conducted in THF. In an embodiment, the reaction is conducted at 50° C. In another embodiment, the reaction is performed under basic conditions. In yet another embodiment, the reaction is performed with triethylamine. In an embodiment, the ratio of dithiol:diacrylate:triethylamine is 1:1.05:0.2. In another embodiment, the ratio of dithiol:diacrylate:triethylamine is 1.05:1:0.2.

In an embodiment, the method further comprises precipitating the polymer. Precipitation can be performed in any solvent or combination of solvents that differ from the solvent of the previous step. In an embodiment, the polymer is precipitated in water, methanol, petroleum ether, or diethyl ether.

In an embodiment, the method further comprises washing the polymer. Ideally, washing is performed in a solvent differing from that used during the synthesis step. Exemplary solvents for washing the polymer include water, methanol, petroleum ether, or diethyl ether.

Capped polymers may be synthesized by further preparing the polymer following the washing step.

In an embodiment, the method of preparing a capped polymer further comprises selecting a monothiol or monoacrylate.

In an embodiment, the method of preparing a capped polymer further comprises reacting the washed polymer with the monothiol or monoacrylate to produce a capped polymer. The reaction may be performed in solvent or under solventless conditions. Exemplary solvents for the synthesis of the polymer include THF, pyrimidine, dichloromethane, DMF, and DMSO. Preferably, the synthesis is conducted in THF. In an embodiment, the reaction is conducted at 50° C. In another embodiment, the reaction is performed under basic conditions. In yet another embodiment, the reaction is performed with triethylamine.

In an embodiment, the method of preparing a capped polymer further comprises precipitating the capped polymer. Precipitation can be performed in any solvent or combination of solvents that differ from the solvent of the previous step. In an embodiment, the capped polymer is precipitated in water, methanol, petroleum ether, or diethyl ether.

In an embodiment, the method of preparing a capped polymer further comprises washing the capped polymer. Ideally, washing is performed in a solvent differing from that used during the synthesis step. Exemplary solvents for washing the capped polymer include water, methanol, petroleum ether, or diethyl ether.

In a preferred embodiment, the method of synthesizing an uncapped polymer comprises: selecting a dithiol and a diacrylate; reacting the dithiol and the diacrylate with triethylamine to produce a polymer; precipitating the polymer; and washing the polymer.

In a preferred embodiment, the method of synthesizing a capped polymer comprises: selecting a dithiol and a diacrylate; reacting the dithiol and the diacrylate with triethylamine to produce a polymer; precipitating the polymer; washing the polymer; selecting a monothiol; reacting the polymer with the monothiol and triethylamine to produce a capped polymer; precipitating the capped polymer; and washing the capped polymer.

In an embodiment, the polymer is not centrifuged.

In another aspect, the disclosure relates to a high throughput method of synthesizing a library of polymers of the disclosure. The method comprises the steps described herein to synthesize an individual polymer with the option to select a new combination of dithiol and diacrylate (for uncapped polymers) or dithiol, diacrylate, and monothiol/monoacrylate (for capped polymers) and repeat the steps of reacting, precipitating, and washing.

In a preferred embodiment, the high throughput method of synthesizing a library of uncapped polymers comprises: (1) selecting a dithiol and a diacrylate; (2) reacting the dithiol and the diacrylate with triethylamine to produce a polymer; (3) precipitating the polymer; (4) washing the polymer; and (5) repeating steps 2-4 at least one more time, selecting, during each repetition, a different combination of dithiol and diacrylate.

In a preferred embodiment, the high throughput method of synthesizing a library of capped polymers comprises: (1) selecting a dithiol and a diacrylate; (2) reacting the dithiol and the diacrylate with triethylamine to produce a polymer;

(3) precipitating the polymer; (4) washing the polymer; (5) selecting a monothiol; (6) reacting the polymer with the monothiol and triethylamine to produce a capped polymer; (7) precipitating the capped polymer; (8) washing the capped polymer; and (9) repeating steps 2-8 at least one more time, selecting, during each repetition, a different combination of dithiol, diacrylate, and monothiol.

In another aspect, the disclosure relates to a method of synthesizing a population of polymeric nanoparticles of the disclosure. In an embodiment, the method comprises obtaining a polymer of the disclosure. Methods of synthesizing the polymers of the disclosure are disclosed herein.

In an embodiment, the method further comprises preparing a mixture comprising the polymer and PLGA-PEG in solvent. Exemplary solvents include DMSO, DMF, acetone, acetonitrile, and THF. In a preferred embodiment, the solvent is DMSO.

In an embodiment, the method further comprises precipitating the mixture to produce nanoparticles. Precipitation may be performed, for example, in water, or in water containing one or more surfactants. Exemplary surfactants include Tween 80, Tween 20, and poly(vinyl alcohol).

In a preferred embodiment, the method of synthesizing a population of nanoparticles comprising an uncapped polymer comprises: selecting a dithiol and a diacrylate; reacting the dithiol and the diacrylate with triethylamine to produce a polymer; precipitating the polymer; washing the polymer; preparing a mixture comprising the polymer and PLGA-PEG in solvent; and precipitating the mixture to produce nanoparticles.

In a preferred embodiment, the method of synthesizing a population of nanoparticles comprising a capped polymer comprises: selecting a dithiol and a diacrylate; reacting the dithiol and the diacrylate with triethylamine to produce a polymer; precipitating the polymer; washing the polymer; selecting a monothiol; reacting the polymer with the monothiol and triethylamine to produce a capped polymer; precipitating the capped polymer; washing the capped polymer; preparing a mixture comprising the capped polymer and PLGA-PEG in solvent; and precipitating the mixture to produce nanoparticles.

In another aspect, the disclosure relates to a high throughput method of synthesizing a library of polymeric nanoparticles of the disclosure. The method comprises the steps described herein to synthesize an individual population of nanoparticles with the option to select a new combination of dithiol and diacrylate (for populations comprising uncapped polymers) or dithiol, diacrylate, and monothiol/monoacrylate (for populations comprising capped polymers) and repeat the steps of reacting, polymer precipitation, washing, mixture preparation, and nanoparticle precipitation.

In a preferred embodiment, the high throughput method of synthesizing a library of polymeric nanoparticles comprising uncapped polymers comprises: (1) selecting a dithiol and a diacrylate; (2) reacting the dithiol and the diacrylate with triethylamine to produce a polymer; (3) precipitating the polymer; (4) washing the polymer; (5) preparing a mixture comprising the polymer and PLGA-PEG in solvent; (6) precipitating the mixture to produce nanoparticles; and (7) repeating steps 2-6 at least one more time, selecting, during each repetition, a different combination of dithiol and diacrylate.

In a preferred embodiment, the high throughput method of synthesizing a library of polymeric nanoparticles comprising capped polymers comprises: (1) selecting a dithiol and a diacrylate; (2) reacting the dithiol and the diacrylate with triethylamine to produce a polymer; (3) precipitating the polymer; (4) washing the polymer; (5) selecting a monothiol; (6) reacting the polymer with the monothiol and triethylamine to produce a capped polymer; (7) precipitating the capped polymer; (8) washing the capped polymer; (9) preparing a mixture comprising the capped polymer and PLGA-PEG in solvent; (10) precipitating the mixture to produce nanoparticles; and (11) repeating steps 2-10 at least one more time, selecting, during each repetition, a different combination of dithiol, diacrylate, and monothiol.

Machine Learning Approaches to Identifying Polymers of the Disclosure

The disclosure also provides a method of identifying novel cancer vaccine adjuvants by constructing a quantitative structure-property relationship (QSPR) model on the immunomodulatory properties of a family of polymers predicted from the chemical structures and anticipated physicochemical properties of the polymers as well as the utilized monomers.

Machine learning is a branch of artificial intelligence which employs statistical pattern recognition algorithms to discern empirical mathematical relationships between observations of materials and extrapolate them to predict the physical, chemical, and biological properties of novel materials. One of the primary application areas of ML has been quantitative structure-property relationship (QSPR) modelling, which can accurately predict in silico how chemical modifications influence biological behavior.

In one aspect, the present disclosure provides a method of predicting the biological activity of a test polymer. The biological activity to be predicted may be, for example, the upregulation of a specific gene or a cluster of genes, the activation of a specific receptor or a cluster of receptors, the activation of a cell, or the production of a cell. In a preferred embodiment, the biological activity to be predicted is the activation of a dendritic cell.

In an embodiment, the method comprises identifying the monomeric units of the test polymer and of a training set of polymers. In another embodiment, the training set of polymers has known biological activity, wherein said biological activity was determined experimentally. In yet another embodiment, the training set of polymers has known activity in at least one immune activation pathway. Example immune activation pathways include MHCI upregulation, MHCII upregulation, CD40 upregulation, CD80 upregulation, and CD86 upregulation.

In an embodiment, the method further comprises categorization of the monomeric units into chemically distinct groups. The chemically distinct groups may be determined based on the moieties in each respective monomer that react with other monomers to form a polymer. Accordingly, chemically distinct groups may include monomers containing one reactive electrophilic moiety, monomers containing two reactive electrophilic moieties, monomers containing one nucleophilic moiety, and monomers containing two nucleophilic moieties. In a preferred embodiment, the chemically distinct groups are acrylates, diacrylates, thiols, and dithiols.

In an embodiment, the method further comprises generating a set of molecular descriptors of the monomeric units in the training set. The molecular descriptors may be 0D, 1D, 2D, 3D, or 4D descriptors. Preferably, the descriptors are 0D, 1D, or 2D.

In an embodiment, the method further comprises deriving an algorithm for each chemically distinct group, wherein each algorithm determines the ability of the monomeric units to activate a dendritic cell by configuring the molecular descriptors of the monomeric units with experimentally derived biological data for the polymers in the training set.

Several types of machine learning algorithms exist. The selection of a given algorithm is based on the nature of the data and the properties of the model to be built. Where QSPR models have been applied in biomaterials design, multiple different machine learning algorithms have been applied including but not limited to linear regression, support-vector machines, random forest models, artificial neural networks, decision trees, naïve Bayes. The choice of machine learning model will impact model performance and abilities of secondary data evaluation. In a preferred embodiment, the algorithms are derived using a random forest model, which enables one to quantify predictive uncertainty, to re-prioritize predictions according to high or low confidence, to increase the predictive performance, and to generate knowledge-rich data to improve the machine learning model.

The experimentally derived biological data may be represented using various metrics. In one embodiment, the data may be represented as "percentage activation compared to positive control" using equation (I):

$$\frac{[\% \text{ activated cells}]_{polymer} - [\% \text{ activated cells}]_{antigen}}{[\% \text{ activated cells}]_{LPS} - [\% \text{ activated cells}]_{antigen}} \quad (I)$$

wherein, [% activated cells]$_{polymer}$ is defined as the percentage of dendritic cells exhibiting activation of the at least one immune activation pathway upon stimulation with a polymer of the training set; [% activated cells]$_{antigen}$ is defined as the percentage of dendritic cells exhibiting activation of the at least one immune activation pathway upon stimulation with an antigen; and [% activated cells]$_{LPS}$ is defined as the percentage of dendritic cells exhibiting activation of the at least one immune activation pathway upon stimulation with lipopolysaccharide.

In another embodiment, the data may be represented as "absolute activation" using equation (II):

$$[\% \text{ activated cells}]_{polymer} - [\% \text{ activated cells}]_{antigen} \quad (II)$$

wherein, [% activated cells]$_{polymer}$ is defined as the percentage of dendritic cells exhibiting activation of the at least one immune activation pathway upon stimulation with a polymer of the training set, and [% activated cells]$_{antigen}$ is defined as the percentage of dendritic cells exhibiting activation of the at least one immune activation pathway upon stimulation with an antigen.

In a preferred embodiment, the data may be represented as "relative activation" using equation (III):

$$\frac{[\% \text{ activated cells}]_{polymer}}{[\% \text{ activated cells}]_{antigen}} \quad (III)$$

wherein, [% activated cells]$_{polymer}$ is defined as the percentage of dendritic cells exhibiting activation of the at least one immune activation pathway upon stimulation with a polymer of the training set, and [% activated cells]$_{antigen}$ is defined as the percentage of dendritic cells exhibiting activation of the at least one immune activation pathway upon stimulation with an antigen.

In an embodiment, the method further comprises combining the algorithms for each chemically distinct group into a combined algorithm. In a preferred embodiment, the combined algorithm is a random forest ensemble model.

In an embodiment, the method further comprises determining a set of molecular descriptors for the test polymer.

In an embodiment, the method further comprises predicting dendritic cell activation of the test polymer using the combined algorithm. In a preferred embodiment of the method, the activity of the test polymer can be predicted based on the experimentally-determined activity of the training set of polymers.

In a preferred embodiment, the disclosure relates to a method of predicting dendritic cell activation by a test polymer comprising: identifying the monomeric units of the test polymer and of a training set of polymers, wherein the training set of polymers have known activity in at least one immune activation pathway; categorizing the monomeric units into chemically distinct groups; generating a set of molecular descriptors of the monomeric units in the training set; deriving an algorithm for each chemically distinct group, wherein each algorithm determines the ability of the monomeric units to activate a dendritic cell by configuring the molecular descriptors of the monomeric units with experimentally derived biological data for the polymers in the training set; combining the algorithms for each chemically distinct group into a combined algorithm; determining a set of molecular descriptors for the test polymer; and predicting dendritic cell activation of the test polymer using the combined algorithm.

In another aspect, the disclosure relates to a method of identifying a polymer-based adjuvant for a vaccine. In an embodiment, the vaccine is for the treatment of cancer. In another embodiment, the cancer is skin cancer. In yet another embodiment, the cancer is melanoma.

In an embodiment, the method comprises selecting one or more test polymers with unknown activity in the activation of dendritic cells. The unknown activity may, for instance, be the activation of an associate immune pathway. Example immune activation pathways include MHCI upregulation, MHCII upregulation, CD40 upregulation, CD80 upregulation, and CD86 upregulation. In a preferred embodiment, the test polymer comprises monomeric units selected from the group consisting of diacrylates, dithiols, acrylates, and monothiols.

In an embodiment, the method further comprises determining a set of molecular descriptors for the one or more test polymers. The molecular descriptors may be 0D, 1D, 2D, 3D, or 4D descriptors. Preferably, the descriptors are the same as those previously generated for a set of training polymers used in a subsequent step. Preferably, the descriptors are 0D, 1D, or 2D.

In an embodiment, the method further comprises, by machine, accessing a body of data comprising molecular descriptors and dendritic cell activation data of a set of training polymers, wherein the body of data has been configured to derive an algorithm for determining the ability of a polymer to activate a dendritic cell based on its molecular descriptors.

In an embodiment, the method further comprises applying the set of molecular descriptors for the one or more test polymers to the algorithm.

In an embodiment, the method further comprises identifying a polymer from the one or more test polymers for development into an adjuvant for a vaccine.

In a preferred embodiment, the disclosure relates to a method of identifying a polymer-based adjuvant for a vaccine comprising: selecting one or more test polymers with unknown activity in the activation of dendritic cells; determining a set of molecular descriptors for the one or more test polymers; by machine, accessing a body of data comprising molecular descriptors and dendritic cell activation data of a set of training polymers, wherein the body of data has been configured to derive an algorithm for determining the ability of a polymer to activate a dendritic cell based on its molecular descriptors; applying the set of molecular descriptors for the one or more test polymers to the algorithm; and identifying a polymer from the one or more test polymers for development into an adjuvant for a vaccine.

In another aspect, the disclosure relates to a machine-assisted method of preparing an adjuvant for a vaccine. In an embodiment, the vaccine is for the treatment of cancer. In another embodiment, the cancer is skin cancer. In yet another embodiment, the cancer is melanoma.

In an embodiment, the method comprises, by machine, accessing a body of data comprising molecular descriptors and dendritic cell activation data of a set of training polymers, wherein the body of data has been configured to derive an algorithm for predicting the ability of a polymer to activate a dendritic cell based on its molecular descriptors.

In an embodiment, the method further comprises using said algorithm to select a polymer with predicted activity in the activation of dendritic cells. In a preferred embodiment, the selected polymer comprises monomeric units selected from the group consisting of diacrylates, dithiols, acrylates, and monothiols.

In an embodiment, the method further comprises synthesizing the polymer. Methods for preparing polymers of the disclosure are provided herein.

In an embodiment, the method further comprises precipitating the polymer into nanoparticles. Methods for preparing polymeric nanoparticles of the disclosure are provided herein.

In an embodiment, the method further comprises validating the ability of the nanoparticles to activate dendritic cells. In an embodiment, the validation step comprises in vitro determination of the activation of an immune activation pathway. Preferred immune activation pathways include MHCI activation, MHCII activation, CD40 activation, CD80 activation, and CD86 activation.

In a preferred embodiment, the disclosure relates to a method of preparing an adjuvant for a vaccine comprising: by machine, accessing a body of data comprising molecular descriptors and dendritic cell activation data of a set of training polymers, wherein the body of data has been configured to derive an algorithm for predicting the ability of a polymer to activate a dendritic cell based on its molecular descriptors; using said algorithm to select a polymer with predicted activity in the activation of dendritic cells; synthesizing the polymer; and precipitating the polymer into nanoparticles.

EXAMPLES

The following examples are merely illustrative and are not intended to limit the disclosure to the materials, conditions, or process parameters set forth therein.

Example 1: Database Curation

In order to generate a computational library of polymers, monomers were aggregated and verified for commercial availability. The databases of several chemical vendors (Molport, Enamine, eMolecules) were downloaded, aggregated and imported into RDKit. Molecules were stripped of salts using the RDKit salt stripper node and subsequently separated according to substructures for dithiols (2×[*][S;H1]), terminal diacrylates (2×[*]OC(=O)C=C) and monothiols (1×[*][S;H1]) using the RDKit Functional Group Filter node. Primary amines and aliphatic halogens were filtered from each database; nucleophilic nitrogen-containing heterocycles were also removed from the dithiol database. After curation of the libraries, the dithiol and diacrylate libraries were validated for commercial availability. A corresponding validation step was not performed on the monothiol library due to its large size. The RDKit Canon SMILES node was used to return a database of unique and standardized 26 dithiols, 149 diacrylates and 29586 monothiols, which allows for the synthesis of approximately 120 million unique polymers through all possible combinatorial combinations.

Example 2: Polymer Selection

Owing to the excessively large size of the polymer chemical space identified during data curation (120 million unique compounds), a substructure-based polymer diversity selection protocol was devised. This allowed the selection of a representative but small subset of polymers which could be experimentally synthesized and screened for immunomodulatory properties. Critically, the subset of polymers spanned the entire polymer chemical space and thereby will enable the re-prioritization of chemical subspaces for further testing.

Using the curated diacrylates and dithiol databases, MACCS keys were generated using the RDKit Fingerprint node. A total of 14 diacrylates and 37 dithiols were then selected using the RDKit diversity picker node. Monomers were then reacted together in all combinations in a Michael Addition (Reaction SMARTS=[*:1]OC(=O)C=C.[S;H1][*:2]>>[*:1]OC(=O)CCS[*:2]) with the RDKit Two Component Reaction node to yield a diacrylate-dithiol (AB) repeat unit. This repeat unit was then reacted with the same diacrylate to yield a diacrylate-dithioldiacrylate trimer (ABA). This provided a selection of 1144 possible polymer trimers, which were used to generate MACCS keys. A total of 40 polymers were selected for synthesis using the RDKit Diversity Picker Node. Diversity of the selected polymer library was calculated using the Similarity Fingerprint (CDK Toolkit) node to calculate the maximum and average Tanimoto coefficient.

By proceeding via the above-described divide-and-conquer approach (monomer selection followed by polymer selection rather than direct polymer selection), a high diversity of the polymer set was achieved using a minimum number of necessary monomers. Ultimately, the number of diacrylates and thiols required to synthesize the selected polymers were 13 diacrylates and 32 dithiols. Selection of the minimum number of compounds is essential due to the time investment associated with establishing reaction conditions (reaction solvent and concentration) and a successful workup procedure. Comparison of the chemical diversity of polymer libraries, curated using the two procedures, demonstrates only a minimal difference in the calculated Tanimoto average and maximum (Table 3).

TABLE 3

| Diversity Selection | Tanimoto Average | Tanimoto Maximum |
|---|---|---|
| Direct polymer selection | 0.48 | 0.667 |
| Monomer selection followed by polymer selection | 0.493 | 0.661 |

Visualization of the selected polymer library was achieved using principal component analysis. FIG. 1 demonstrates how the 40 selected base polymers adequately represent the chemical diversity of the entire polymer library.

Figure 2:
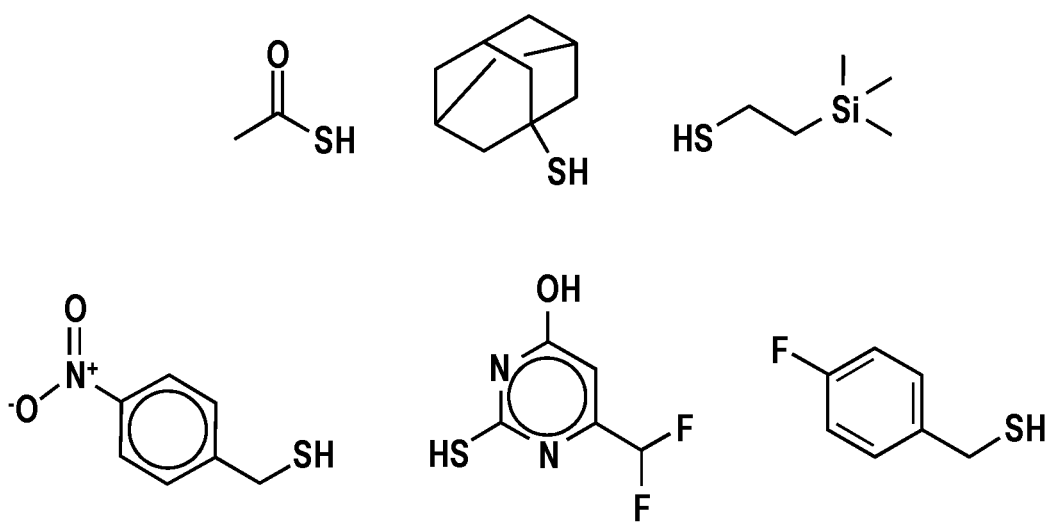
FIG. 2 shows the set of end-caps selected via Diversity Picking for base polymer capping.

End-caps were selected using a similar procedure, wherein MACCS keys were generated and caps were selected using Diversity Picking. Selected end-caps are depicted in FIG. 2.

Example 3: High Throughput Synthesis Design

To allow the rapid synthesis of the selected polymer library, a generalized high throughput reaction procedure compatible with a range of monomers/polymers was developed.

Time Series Polymerization and Capping 1,3-Propanedithiol (1 mol eq.) and 1,6-Hexanediol diacrylate (1.05 mol eq.) were dissolved in THF and Triethylamine (0.2 mol. eq) was added. The reaction mixture was transferred to an NMR tube and reacted at room temperature; $^1$H NMR was taken at 3-hour intervals over 30 hours, after which 4-fluorobenzyl mercaptan (1 mol. eq) was added to the reaction and the reaction was monitored for a further 30 hours.

Figure 3:
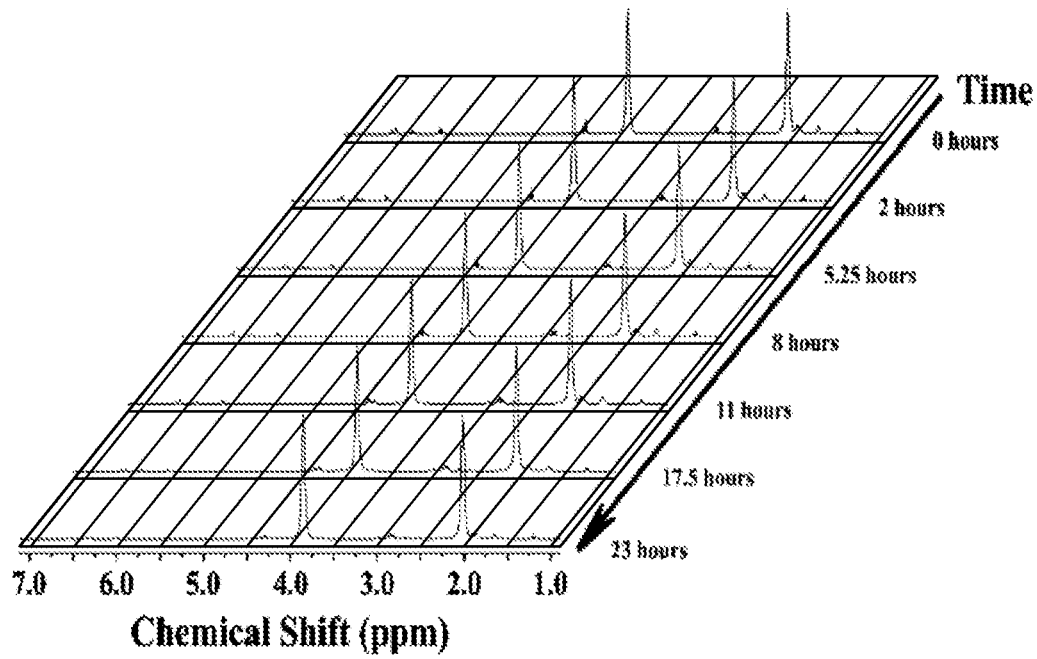
FIG. 3 is a time-resolved $^1$H NMR spectrum demonstrating occurrence of polymerization between 1,3-propanedithiol and 1,6-hexanediol diacrylate at room temperature, measured over 23 hours.

THF was determined to be the preferential solvent, due to its ability to dissolve the majority of monomers and polymers at high concentrations (100-200 mg mL$^{-1}$). Reactions at high concentrations were preferential owing to the requirement for downstream polymer precipitation in water; lower reaction concentrations would increase the solubility of the polymer during precipitation, therefore reducing yield. Triethylamine was used as non-nucleophilic base to deprotonate the nucleophilic thiols. Reaction duration was determined using time-resolved resolved $^1$H NMR at room temperature; this provided an indication of reaction coordinate, which could be compared with an identical reaction at evaluated temperature (50° C.). Consequently, 17 hours at 50° C. was determined as an appropriate duration for the majority of polymerizations to occur. FIG. 3 shows the $^1$H NMR time series between 1,6-hexanediol diacrylate and 1,3-propanedithiol at room temperature. Polymerization is observed by decreasing diacrylate peak intensity with time, found at ~6.5 ppm.

Figure 4:
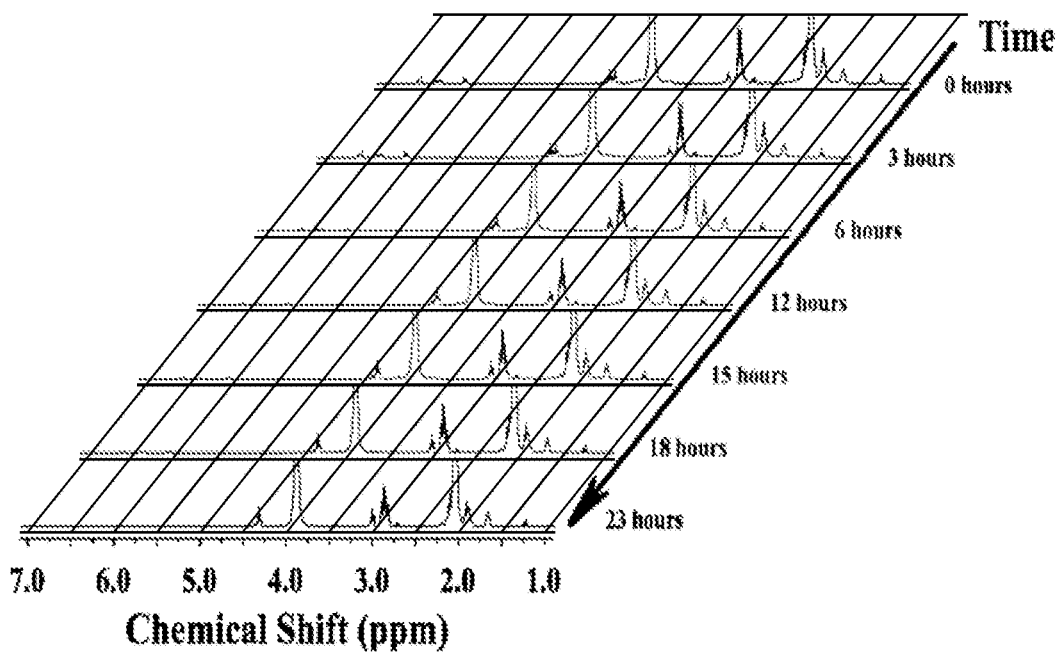
FIG. 4 is a time-resolved $^1$H NMR spectrum demonstrating the occurrence of capping between poly(hexanediol diacrylate-alt-propanedithiol) and 4-fluorobeznyl mercaptan, measured over 23 hours at room temperature.

Reaction duration of base polymer capping was determined using a similar procedure. A minimum of 18-hours reaction duration at 50° C. was determined to be adequate for complete reaction. FIG. 4 shows the capping reaction between poly(hexanediol diacrylate-alt-propanedithiol) and 4-fluorobeznyl mercaptan at room temperature by time resolved $^1$H NMR. Diacrylate peak intensity at 6.5 ppm is observed to decrease with time, indicating successful reaction between polymer and end-cap.

Optimization of Workup Procedure

In alignment with the generalized synthesis protocol, a generalized workup procedure was developed to facilitate preparation of the polymers in a high throughput manner. Initial attempts at polymer workup utilized polymer precipitation in methanol followed by repeated centrifugation and washing. Centrifugation was significantly rate-limitation, and thus a workup procedure which obviated centrifugation was developed. This process involved precipitation of polymer in water, which forced formation of large polymer aggregates (cf. methanol). Subsequently, these aggregates could be washed in methanol, to remove excess monomer and end-cap, without the requirement for centrifugation. This procedure consequently expedited the process of polymer workup.

Protocol Adaption

Owing to the demand for the parallel synthesis of many different polymers, each utilizing different monomers with different physiochemical properties, the high throughput protocol was adapted as necessary. For example, in situations where monomers could not be dissolved in THF at high concentrations, the synthesis procedure was adapted to use DMF and/or pyrimidine. These solvents were selected due to their miscibility in water (for polymer precipitation) and low dielectric constant. Solvents with high dielectric constants (DMF and DMSO) were only used as a last resort due to the ability of these solvents to oxidize thiols.

Example 4: Synthesis of Polymers

Figure 5:
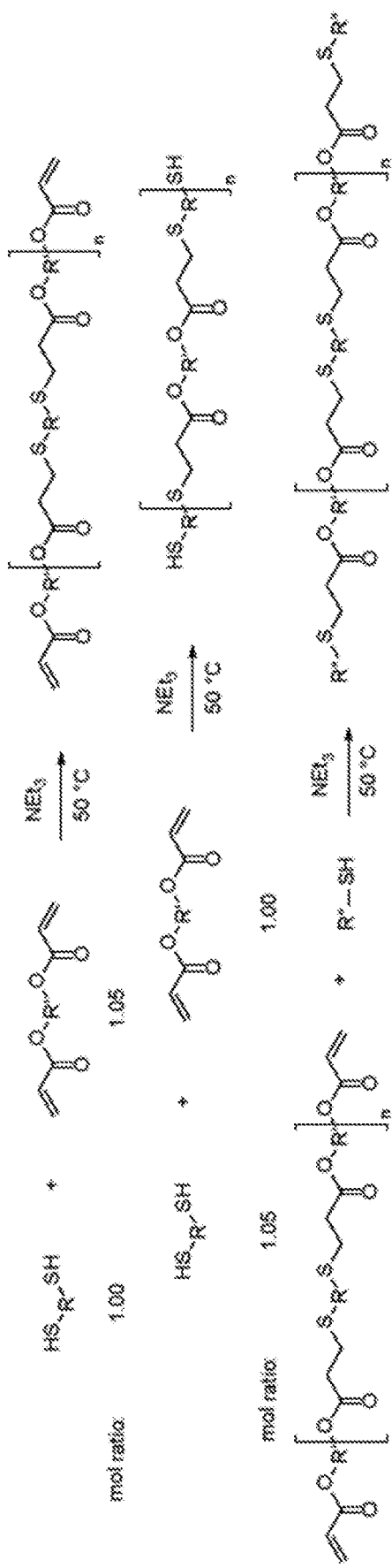
FIG. 5 is a schematic chemical reaction for the synthesis of the poly(β-thioesters).

A series of novel polymers were synthesized by combining two groups of monomers: dithiols and diacrylates. In some cases, the resultant polymers were reacted to a third group of compounds (thiols) to yield the final product. A general schematic reaction is shown in FIG. 5.

General Procedure

Diacrylate-capped polymers were prepared by reacting dithiols with diacrylates at a molar ratio of 1 to 1.05 using 0.2 equivalents of trimethylamine in THF. Dithiol-capped polymers
were prepared by reacting dithiols with diacrylates at a molar ratio of 1 to 1.05. Typically, reactions were conducted at final concentrations between 100-250 mg/mL$^{-1}$ in THF or pyrimidine. The reactions were carried out at 50° C., with 650 RPM stirring and left for 17 hours, or until the polymerization had completed. Polymerizations were monitored by $^1$H NMR spectroscopy, gel permeation chromatography and occurrence of polymer precipitation in water.

Polymers were precipitated by dropwise addition to 20 mL water in a 40 mL scintillation vial. This produced pearl-like globules of polymer which sink to the bottom of the vial. 20 mL of methanol was then added slowly and gently stirred. Supernatant was removed, using mild cooling to immobilize the polymer, when appropriate. The polymer was washed three times with 40 mL methanol, freeze dried for 48 hours and stored at –20° C. The polymer was characterized by $^1$H NMR and gel permeation spectroscopy.

Synthesis of Polymers B1-B12

The diacrylate was weighed in a 4 mL glass vial. The dithiol was dissolved in tetrahydrofuran (THF) at a concentration of 100 mg/mL and added to the diacrylate. THF was added to the mixture to get the concentration of the dithiol+diacrylate mixture to 200 mg/mL. Triethylamine was added to the reaction, the glass vial was transferred to a magnetic stir plate at 50 C. After an overnight reaction, the end-capping agent (4-fluorobenzyl mercaptan) was added to the mixture and the reaction was allowed to proceed for another 24 h at 50 C. The next day, the polymer was precipitated by adding to 50 mL methanol in a plastic Eppendorf tube. The mixture was cooled to –20 C overnight to aid precipitation and the methanol was decanted. The remaining polymer was dissolved in acetone and transferred to a pre-weighed glass vial. The acetone was evaporated.

Synthesis of Polymers B13-821

The diacrylate was weighed in a 4 mL glass vial. The dithiol was dissolved in tetrahydrofuran (THF) at a concentration of 100 mg/mL and added to the diacrylate. THF was added to the mixture to get the concentration of the dithiol+ diacrylate mixture to 200 mg/mL. Triethylamine was added to the reaction, the glass vial was transferred to a magnetic stir plate at 50 C and the reaction was allowed to proceed for 24 h. The end-capping agent (N-acetyl cysteine) was suspended in THF at a concentration 250 mg/mL. The suspension was added
to the reaction mixture and the reaction was allowed to proceed for 24 h. On the next day, the polymers were precipitated by adding to the THF solution to 40 mL water in a pre-weighed glass vial. The water was decanted and another 40 mL water was added to remove residues of the end-capping agent. The water was decanted, the vials were frozen to −80 C and the product was lyophilized for 2 days.

Synthesis of Polymers A1-A63

The diacrylates were weighed in 8 mL glass vials. To these, dithiol and triethylamine were added. The mixture was placed on a stir plate at 60 C, and the reaction was allowed to proceed for 18-24 h. No attempt was made to purify these polymers.

Synthesis of Polymers A64-A68

The diacrylate was transferred to a pre-weighed 20 mL glass vial, and dissolved in tetrahydrofuran (THF) at a concentration of 400 mg/mL. To enable dissolution, the mixture of the diacrylate and THF were placed on a shaker (at RT, protected from light) for 10-20 min. For the reaction, the correct volume of the dithiol was added to a 8 mL glass vial. To this, the diacrylate dissolved in THF was added. The reaction mixture was diluted to contain 200 mg polymer/mL by adding more THF. Triethylamine was added to the mixture, and the vial was placed on a stir-plate at 50 C. The reaction was allowed to proceed for ~24 h. On the next day, the polymer solutions were added to 20 mL water and mixed well. To this 20 mL methanol was added and the precipitates were allowed to settle. The mixture remained hazy, but these nanoprecipitates were deemed difficult to recover. Hence the supernatant was removed and 40 mL methanol was
added to clean the precipitates that collected at the bottom of the vial. After a quick stir, the methanol was discarded. The vials were frozen at −80 C and lyophilized.

Synthesis of Polymers A22-A26

The diacrylate was transferred to a pre-weighed 20 mL glass vial, and dissolved in tetrahydrofuran (THF) at a concentration of 400 mg/mL. To enable dissolution, the mixture of the diacrylate and THF were placed on a shaker (at RT, protected from light) for 10-20 min. For the reaction, the correct volume of the dithiol was added to a 8 mL glass vial. To this, the diacrylate dissolved in THF was added. The reaction mixture was diluted to contain 200 mg polymer/mL by adding more THF. Triethylamine was added to the mixture, and the vial was placed on a stir-plate at 50 C. The reaction was allowed to proceed for ~24 h. After 24 h, the end-capping agent was added to the reaction, and the reaction was allowed to proceed for another day.

Synthesis of Polymers A69-A73

The dithiol was dissolved in THF at a concentration of 300 mg/mL. The diacrylates were weighed into 8 mL glass vials. Stir bars were added to the glass vials and the dithiol solution was added to the vial. THF was added to the reaction mixture to bring the total concentration of the monomers to 200 mg/mL. Triethylamine was added to the mixture and the vials were placed at 50 C on a stir-plate. The reaction was allowed to proceed for 24 h. At the end of this period, the THF solution was added to 10-15 mL chilled water in a 40 mL glass vial. The vial was placed on ice at this point. Upon complete polymer precipitation, water was added to fill the vial. The contents were mixed, and the polymer precipitates were allowed to settle. The supernatant water was removed and the polymer was washed further with 40 mL water. The polymers were then frozen to −80 C and lyophilized for 2 days.

Synthesis of Polymers A27-A31

The dithiol was dissolved in THF at a concentration of 300 mg/mL. The diacrylates were weighed into 8 mL glass vials. Stir bars were added to the glass vials and the dithiol solution was added to the vial. THF was added to the reaction mixture to bring the total concentration of the monomers to 200 mg/mL. Triethylamine was added to the mixture and the vials were placed at 50 C on a stir-plate. The reaction was allowed to proceed for 24 h. At the end of the 24 h period, the endcap was suspended in THF at a concentration of 250 mg/mL and added to the reaction mixture. The reaction was allowed to proceed for 24 h. After 24 h, the THF solution was added to 10-15 mL chilled water in a 40 mL glass vial. The vial was placed on ice at this point. Upon complete polymer precipitation, water was added to fill the vial. The contents were mixed, and the polymer precipitates were allowed to settle. The supernatant water was removed and the polymer was washed further with 40 mL water. The polymers were then frozen to −80 C and lyophilized for 2 days.

Synthesis of Polymers A74-A80 and B32-B84

Diacrylate-capped polymers were prepared by reacting dithiols with diacrylates at a molar ratio of 1 to 1.05 using 0.2 equivalents of trimethylamine in THF. Dithiol-capped polymers were prepared by reacting dithiols with diacrylates at a molar ratio of 1 to 1.05. Typically, reactions were conducted at final concentrations between 100-250 mg mL$^{-1}$ in THF or pyrimidine. The reactions were carried out at 50° C., with 650 RPM stirring and left for 17 hours, or until the polymerization had completed. Polymerizations were monitored by $^1$H NMR spectroscopy, gel permeation chromatography and occurrence of polymer precipitation in water.

Example 5: Synthesis of Nanoparticles

General Procedure

Polymer nanoparticles were precipitated by preparing a mixture of polymer (16 mg mL$^{-1}$) and PLGA-PEG (4 mg mL$^{-1}$) in DMSO, which was added dropwise to a 10× excess of water, with stirring at 650 RPM. The mixture was stirred for 6 hours, after which nanoparticles were characterized using Dynamic Light Scattering. Particles were typically screened immediately following synthesis.

Synthesis of Nanoparticles A1-A31 and B64-B73

One milliliter solution of PTE polymers and poly(lactide-co-glycolide)-b-poly(ethylene glycol) (PLGA-PEG; 50:50: lactide:glycolide; 15 KDa-2 KDa, PLGA-PEG) was prepared in DMSO. The total polymer concentration was 20 mg/mL. The ratio of PBTE:PLGA was 16 mg:4 mg. One milliliter of the polymer solution was added to 10 mL of stirring water in a 20 mL glass vial. The stirring speed was ~600 RPM. The mixture was stirred for another 6 h. The nanoparticles hence formed were characterized for size using the dynamic light scattering.

Synthesis of Nanoparticles B1-B63

One milliliter solution of polymers and PLGA-PEG was prepared in DMSO. The polymers were dissolved in DMF at a concentration of 100 mg/mL. PLGA-PEG was dissolved in DMSO at a concentration of 20 mg/mL. One hundred and sixty microliters of the polymers were mixed with 200 uL of PLGA-PEG in a 4 mL glass vial. Six-hundred and forty microliters of DMSO were added to bring the volume of the mixture to 1 mL. Ten milliliters of deionized water was added to a 20 mL glass vial, which was placed on a stir-plate at a stirring speed of 650 RPM. The polymer solution was added to water while stirring. Six hours later, the size of the nanoparticles was measured using dynamic light scattering.

Polymers B26, B27, B34, B35, B39, B43, B44, B45 were heated to 60 C to dissolve them, then diluted in DMSO and used. Polymers B5, B21, B23, B24, B25, B26, B32, B39, B43, B44, and B45 formed hazy solutions when diluted in DMSO with PLGA-PEG. Hence, these polymer solutions were heated to 60 C. Polymers B5, B21, B24, B25, B32, B39, B43, B44, and B45 made clear solutions and were added to water in that form. Polymers B23 and B26 retained their haziness, and they were added to water in that form.

Example 5: Physicochemical Characterization of the Polymers and Nanoparticles Polymers were characterized using gel permeation chromatography (GPC) and nuclear magnetic resonance (NMR) as follows. The molecular weight of the polymers was determined using an Agilent® GPC coupled with a triple detector array 305 (Malvern, USA). A LT6000L mixed high organic column (Malvern, USA) was used as a stationary phase. The occurrence of the end-capping reaction was confirmed using $^1$H-NMR and $^{19}$F-NMR analysis.

Figure 6:
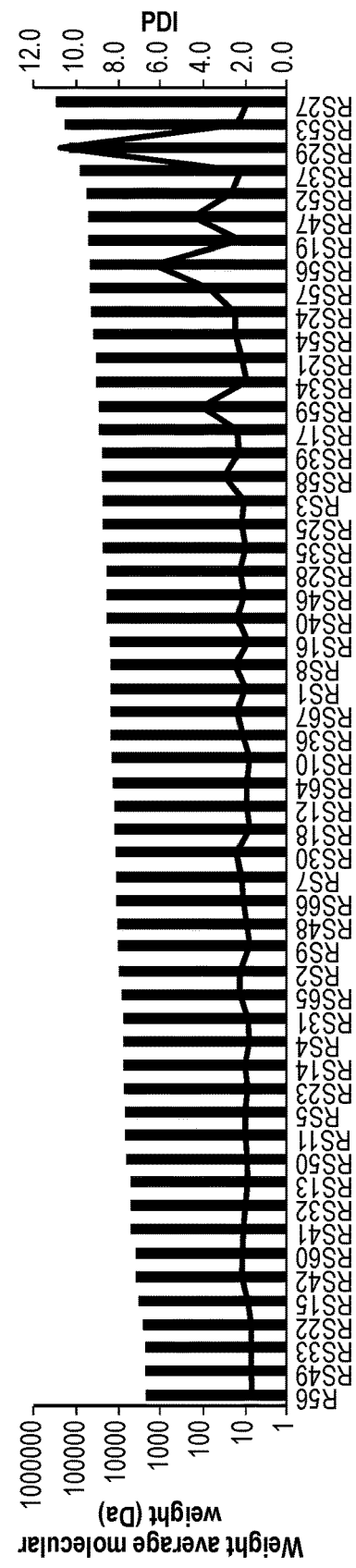
FIG. 6 is a graph showing the GPC analysis of synthesized polymers. The bars indicate molecular weight (left Y-axis); the line indicates polydispersity index (right Y-axis).

The results of the GPC analysis of a subset of polymers is shown in FIG. 6. Polymers ranged in molecular weight from 1000-100000 Da, and a polydispersity index of 2-3. Some polymers did show a larger polymer dispersity index.

Figure 7:
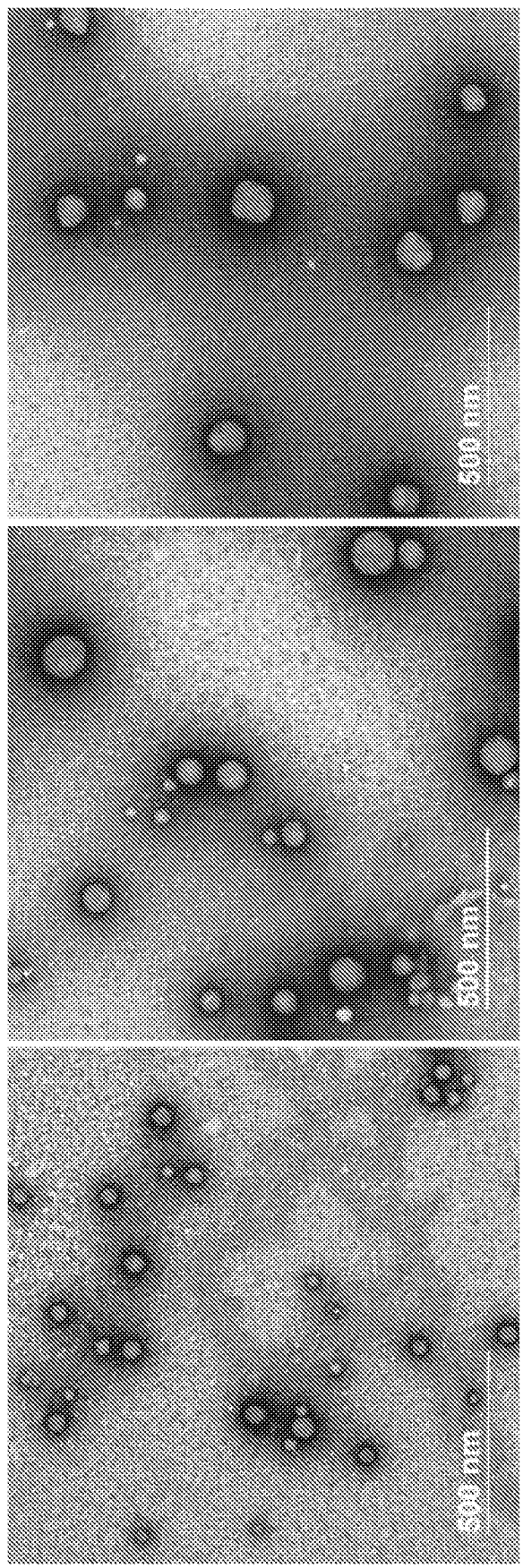
FIG. 7 shows transmission electron microscopy analysis of the polymeric nanoparticles.

To determine the size of nanoparticles, ~50 µL of the 2 mg/mL nanoparticle dispersion was added to 1 mL deionized water and the samples were analyzed using dynamic light scattering. Additionally, size and surface morphology of the nanoparticles was determined using transmission electron microscopy (TEM). TEM analysis of the nanoparticles is shown in FIG. 7.

Figure 8:
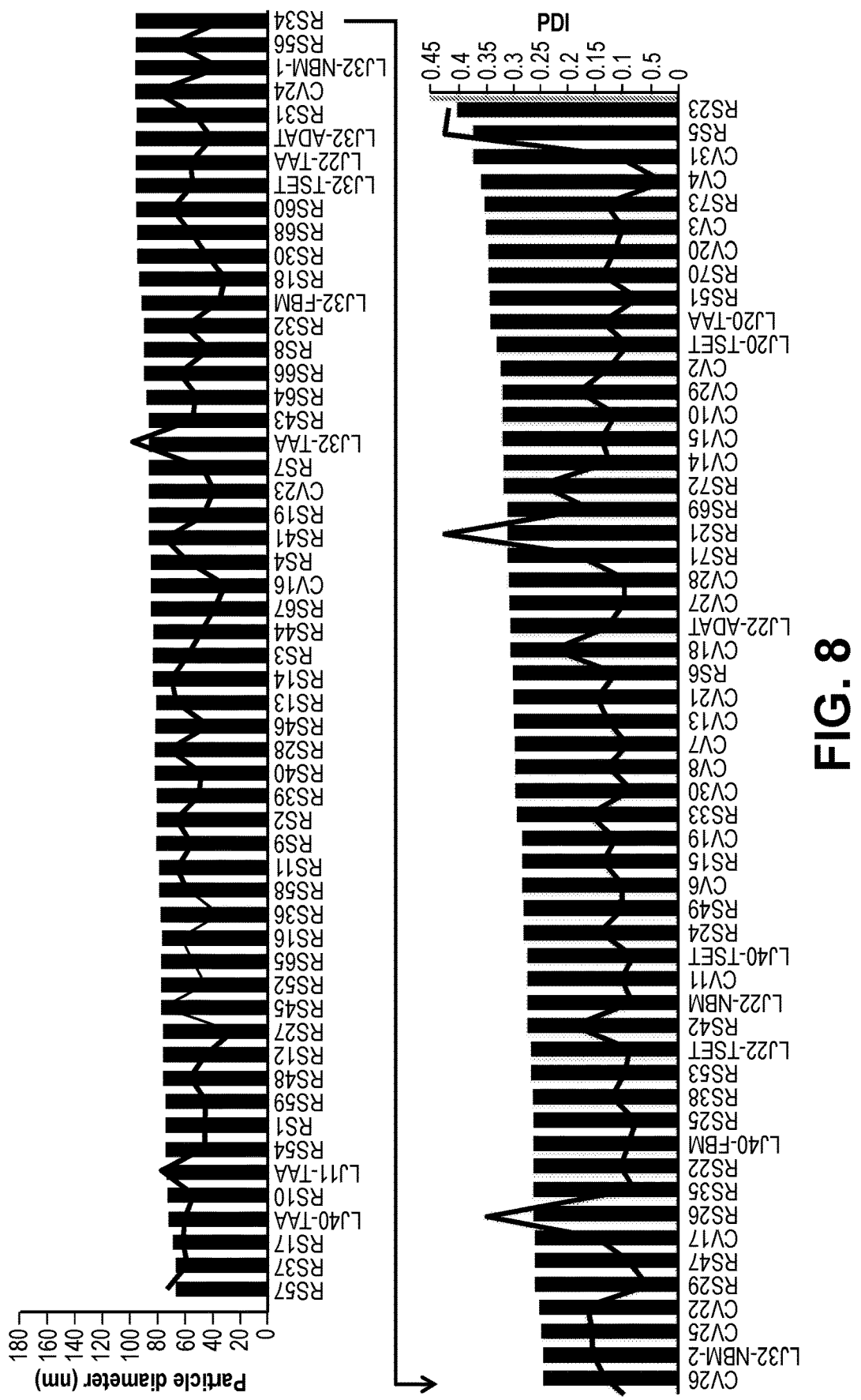
FIG. 8 is a graph showing the dynamic light scattering analysis of synthesized nanoparticles. The bars indicate particle size (left Y-axis); the line indicates polydispersity index (right Y-axis).

The particle size of the nanoparticles used in our studies was measured using dynamic light scattering and shown in FIG. 8. Particle size ranged from 60-160 nm and generally had a polydispersity index of ~0.1-0.25. Most formulations had a unimodal particle size distribution.

Example 6: High Throughput Characterization of Dendritic Cell Response

Cultivation of Bone Marrow-Derived Dendritic Cells

Mouse bone marrow-derived dendritic cells (BMDCs) were harvested from immunocompetent C57BL/6 mice using protocols known in the art. Briefly, tibias and femurs were collected from euthanized mice and bone marrow cells were flushed with PBS. Red blood cells were removed by ACK Lysis buffer (Invivogen) and cells were washed with PBS. Cells were resuspended in complete RPMI media (10% fetal bovine serum, 100 µg/mL streptomycin and 100 U/mL penicillin) supplemented with 20 ng/mL granulocyte-macrophage colony-stimulating factor (GMCSF) (PeproTech, Rocky Hill, NJ) and 50 µM 2-mercaptoethanol (Sigma). Fresh cell media was replenished on d3 and cells were harvested on d6 for experiments.

In Vitro BMDC Activation Assays

BMDCs ($1\times10^5$) were seeded in a 96 well plate. After a 2 hr incubation, cells were treated with 0.1 mg/ml of nanoparticles and 2.5 µg/ml of OVA257-264 (SIINFEKL) peptides. Lipopolysaccharide (LPS, 10 µg/ml) was used as positive control for in vitro assays. Cells were collected 48 hr after incubation with treatments, stained with fluorophore bound Abs to label dendritic cells (CD11c), co-stimulatory molecules (CD40, CD80, CD86 and MHC II), and antigen presentation (OVA257-264 peptide bound to H-2 Kb). Stained cells were analyzed using flow cytometry (BD LSR Fortessa).

Characterization of Dendritic Cell Response to Nanoparticles

The response of dendritic cells to ~130 new polymers was characterized in vitro using high throughput flow cytometry. Dendritic cell response was measured using 5 activation markers, and for each activation marker, a polymer score was assigned to the polymer. Polymer score was calculated using equation (I):

$$\frac{[\% \text{ activated cells}]_{polymer} - [\% \text{ activated cells}]_{antigen}}{[\% \text{ activated cells}]_{LPS} - [\% \text{ activated cells}]_{antigen}} \quad (I)$$

Figure 9:
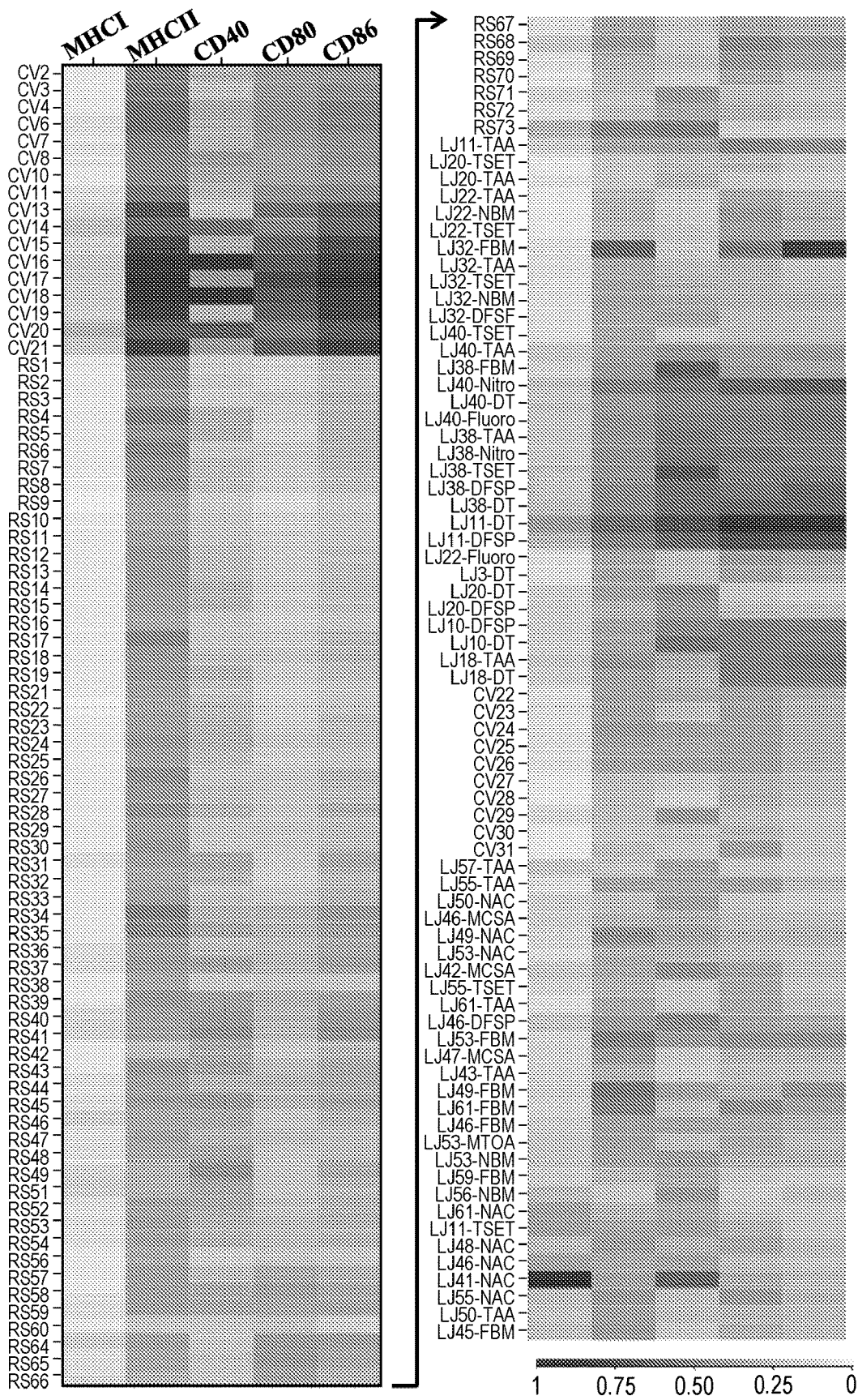
FIG. 9 is a heatmap showing dendritic cell response to all synthesized polymers. Values are expressed as a proportion of the maximum discovered activation for that pathway.

The results of these studies are shown in FIG. 9. Several polymers showed extensive upregulation of all five activation markers. Specifically, A76, B15, B16, B17, B18, B19, B20, and B38 showed promising activity.

Mechanism of Upregulation of MHCI:SIINFEKL

Figure 10:
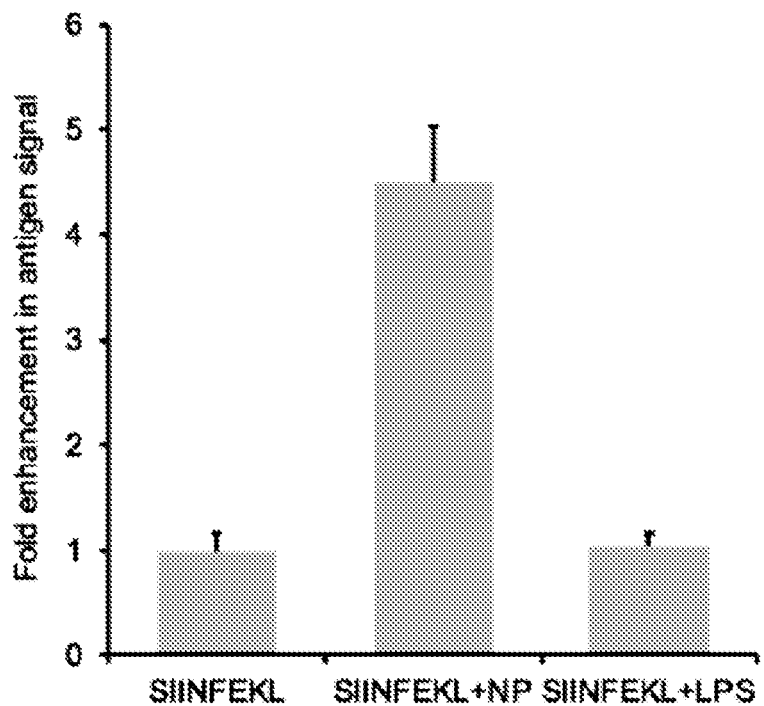
FIG. 10 is a graph showing results of a BCA assay, indicating that adsorption of peptide on nanoparticles leads to increased protein signal.

Interestingly, dendritic cells treated with the nanoparticles of the disclosure showed significant upregulation of MHCI: SIINFEKL. This is likely due to their ability to activate the dendritic cells and efficiently deliver the antigen intracellularly. With regards to the latter phenomenon, it was hypothesized that mixing the antigen with the nanoparticles led to the adsorption of the antigen on the nanoparticle surface, which ultimately led to its better cell uptake. To determine surface adsorption of antigen on nanoparticle surface, a bicinchoninic acid (BCA) assay was performed. Results of the BCA assay are shown in FIG. 10.

Example 7: Computational Polymer Representation and QSPR Model Construction

Data Aggregation and Analysis

Figure 11:
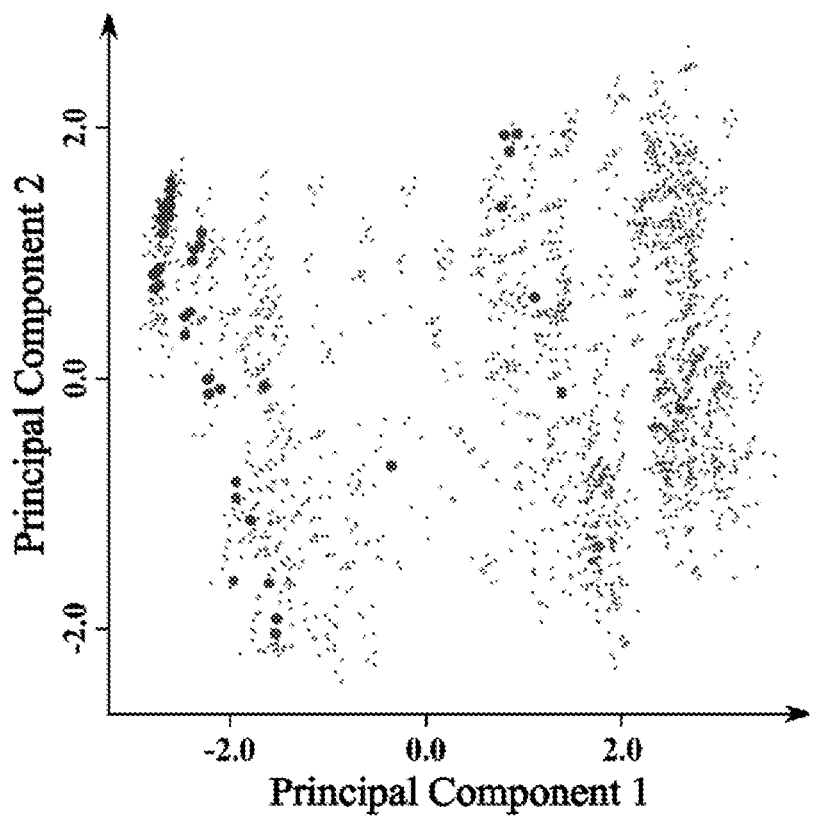
FIG. 11 is a plot displaying principal component analysis of an initial set of synthesized and screened polymers. Diversity selected polymers (light big dots) and other polymers (dark big dots) are shown. Principal component analysis calculated in 2 dimensions using MACCS key fingerprints on diacrylate-dithiol-diacrylate units.

From the library of diversity-selected polymers identified in Example 2, an initial set of 9 base polymers were synthesized, which were derivitized with 5 different end-caps to yield a total of 33 unique polymers. These polymers were used to synthesize nanoparticles, which were incubated with dendritic cells. The dendritic cells were profiled for expression of MHCI, MHCII, CD40, CD80 and CD86 markers using high-throughput flow cytometry as described in Example 6. This data was aggregated alongside a previous prepared dataset of 83 polymers. This dataset consisted of the activation data of polymers which were synthesized using readily available building blocks (cf. diversity selection). FIG. 11 shows a principal component analysis plot of the synthesized base polymers, highlighting the difference between the two polymer datasets.

Computational Polymer Representation

QSPR seek to identify correlations between the numerical representations and descriptions of molecules and the quantified properties of interest. Consequently, the chemical structures of molecules must be converted to mathematical representations which capture the underlying structural— and physiochemical—properties of the molecule that are likely to govern the property of interest such as their biological activity. These numerical representations can be derived experimentally (e.g. measured size or zeta potential of nanoparticles) or computationally (e.g. predicted size or zeta potential), depending on the available data and infrastructure, importance, and accessibility of selected properties, and the requirements of the approach and model.

In order to rapidly screen a variety of polymer structures to establish a QSPR model to predict the immunomodulatory properties of millions of virtual polymeric biomaterials, the polymer structure was represented using exclusively computationally calculated molecular descriptors, although the approach could easily be extended to incorporate measured properties for potentially increased accuracy. This computationally-derived property profile calculation requires that the polymer is represented as a defined chemical structure, which is imported into molecular descriptor calculator software. However, polymers are challenging to represent by defined chemical structures owing to their structural heterogeneity.

Furthermore, even if an entire polymer chain could accurately be represented virtually, molecular descriptor software is adapted to the calculation of small molecule structures. To address this challenge, several different polymer representations were constructed, which could be successfully converted into molecular descriptors. Alongside the previously attained in vitro data, these descriptors were used to construct different machine learning classifiers, which were evaluated based on their predictive capacity. This allowed for the selection of virtual polymer representations which yielded the most useful molecular descriptors for constructing a predictive QSPR model.

Figure 12:
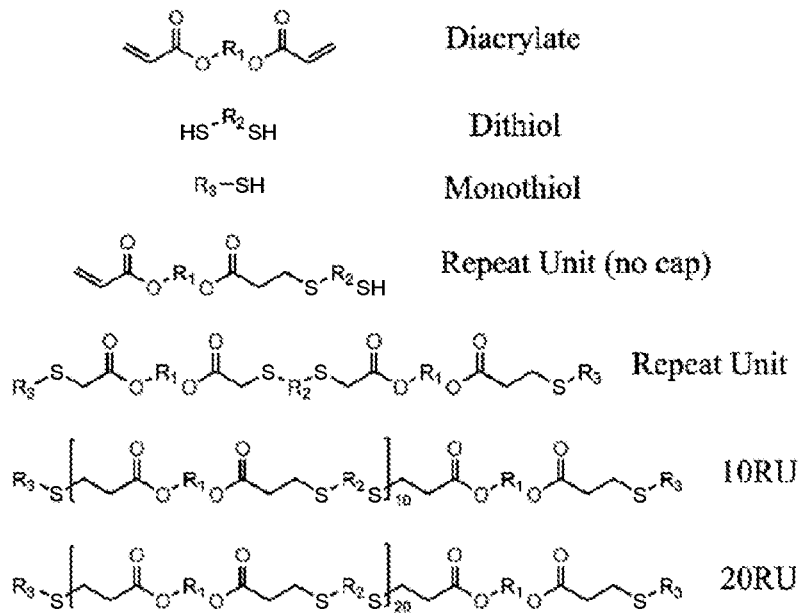
FIG. 12 is an illustration of the various polymer representations used in the molecular descriptor calculation and QSPR model construction.

The selected polymer representations were determined by previously established polymer representations (e.g. repeat unit (RU)) alongside increasingly realistic representations (10 RUs, 20 RUs). Further, some representations included or excluded the presence of the end-cap, thus shifting the weighting of the backbone vs. end-cap in the resultant descriptor calculation. The different representations used are illustrated in FIG. 12.

Molecular Descriptor Calculation

The polymer representations selected in the previous step were imported into two different software to calculate molecular descriptors: PaDEL and Mordred. Molecular descriptors were successfully calculated in both software using the low molecular weight polymer representations (e.g. monomers). However, use of larger polymer representations (RU, 10 RU and 20 RU) led to crashes and stalling in the PaDEL software since this software was designed with property calculation for small molecules with low molecular weight in mind. Conversely, descriptor calculation using the Mordred software is typically fast and error-free. Therefore, Mordred became the chosen software for molecular descriptor calculations. Attempts at calculating descriptors for the largest polymer representation (20 RU) were successful for a subset of polymers, but excessive software stalling prevented descriptor calculation on all polymers. Therefore, the 20 RU representation was not utilized further.

Several different types of molecular descriptor exist: 0D, 1D, 2D, 3D and 4D. Of these, 0D, 1D and 2D descriptors were calculated for the models described herein. Random forest models perform an automated feature selection, such that a large set of computationally derived properties can be selected for the model without the need for pre-filtering.

Model Construction and Evaluation of Polymer Representations

Figure 13:
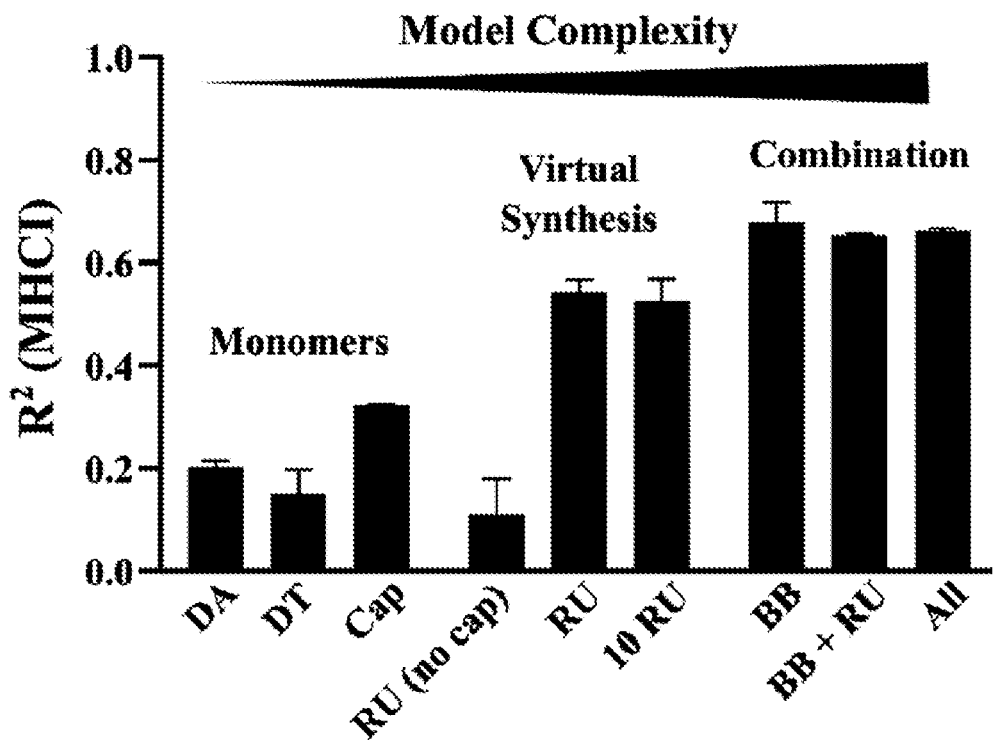
FIG. 13 is a graph showing the predictive capacity of machine learning models constructed using molecular descriptors from different polymer representations. $R^2$ was calculated on MHCI random forest regression models using 10-fold cross validation. (DA=diacrylate, DT=dithiol, RU=repeat unit, BB=building block)

Using the calculated molecular descriptors and in vitro screening data, machine learning classifiers were constructed to predict MHCI, MHCII, CD40, CD80 and CD86 marker expression. This was achieved by first eliminating constant and highly correlated descriptors (to reduce the computational resources needed as well as the probability of model overfitting), which left several hundred different descriptors for model construction. Owing to the large number of molecular descriptors and (predictably) noisy nature of our biological data, a random forest regression model was constructed. Importantly, random forest models are simple to implement (due to unneeded parameter tuning) and exhibit a reduced tendency to overfit noisy data. To evaluate the predictive capacity of the constructed machine learning models, 10-fold cross validation was performed and statistical measures for goodness-of-fit were calculated. This allowed a robust evaluation of the polymer representations which captured the most useful molecular descriptors. FIG. 13 compares the goodness-of-fit of different models constructed using different polymer representations on MHCI activation.

Nine different machine learning models were constructed, six using the previously described polymer representations, and three using different combinations of these representations. $R^2$, the correlation coefficient, was used to evaluate model goodness-of-fit as it measures the strength of the relationship between the predicted and measured data. Each of the monomer descriptors exhibit poor $R^2$ values, indicating that they are poor polymer representations. Interestingly, there is notable variance in the $R^2$ values between the monomers, indicating differential importance of the diacrylate, dithiol and end-cap on MHCI activation. Regarding virtually synthesized polymer representations, both capped representations of the polymer (RU and 10 RU) yield good model predictive capacity. Surprisingly, conjugation of the diacrylate to dithiol (RU (no cap)) does not offer any significant increase in $R^2$ over monomers alone. Finally, all of the combination models are observed to have high model predictive capacity, with little difference between model which utilize only the monomers (BB), or monomers and virtually synthesized representations (BB+RU, AII).

It was concluded that the most practical polymer representation is the Building Block (BB) model, owing to the high predictability of the model, alongside use of unmodified monomers as polymer representations and therefore rapid accessibility; this avoids the combinatorial explosion associated with the calculation of the virtually synthesized representations. This is because monomer descriptors are simply reused in different combinations to represent different polymers. This obviates the requirement for virtual polymer synthesis, and limits the number of calculations required to obtain molecular descriptors.

Initial Model Predictions

Using the previously constructed random forest regression models, the immunomodulatory properties of all polymers which could be immediately synthesized from an inventory of monomers was predicted. Further, owing to the observed impact of end-capping on marker expression, the pathway activation of all monothiols in the database was predicted. From these predictions, 27 base polymers were selected to synthesize, and two additional end-caps (mercaptoorotic acid and mercaptosuccinic acid) were obtained.

Figure 14:
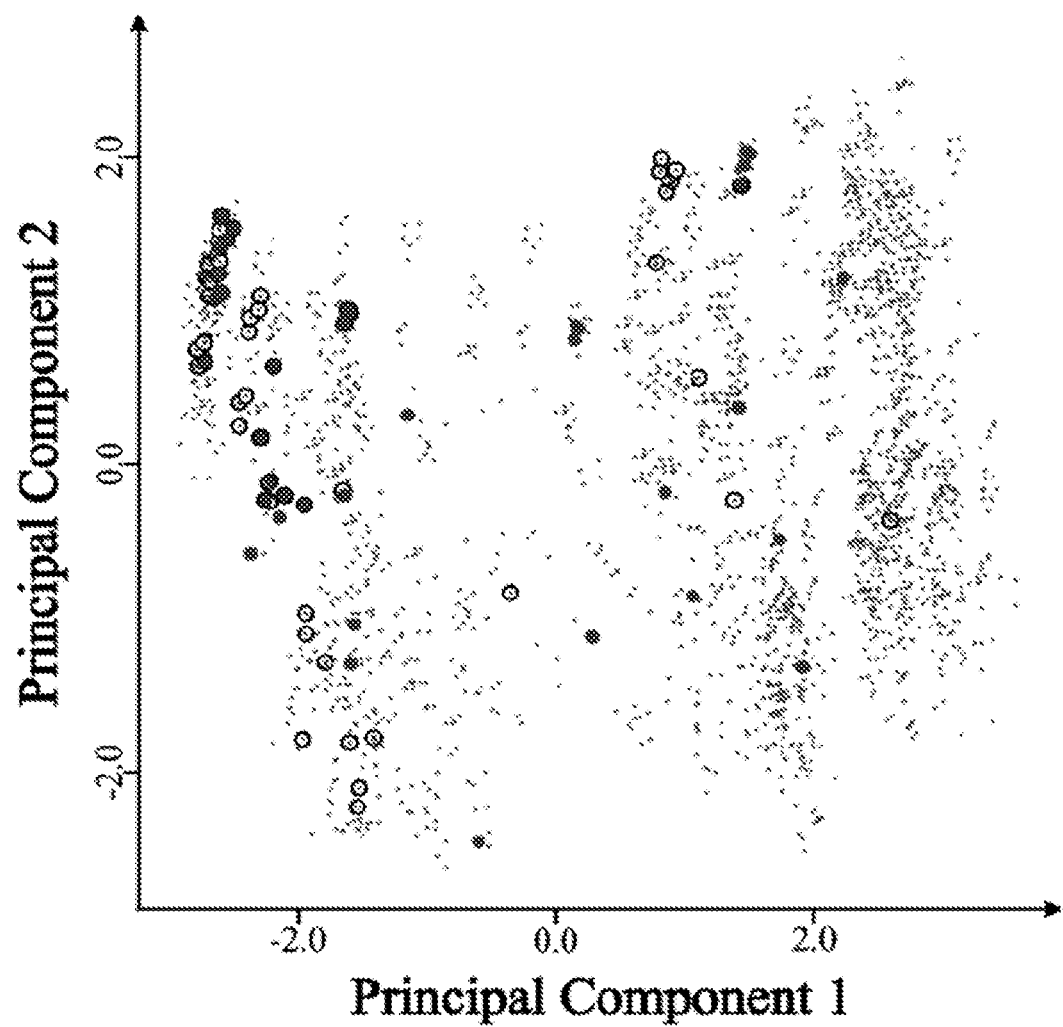
FIG. 14 is a plot displaying principal component analysis of base polymers selected for synthesis using machine learning. Polymers for synthesis (filled in circles), successfully synthesized polymers (empty circles), and all base polymers (gray) are shown. Principal component analysis was calculated in 2 dimensions using MACCS key fingerprints on diacrylate-dithiol-diacrylate units.

Base polymer selection was conducted according to maximum activation across all immune pathways and prediction variance. The rationale for this active learning approach was to select polymers which could be potential hits while also sampling diverse polymers and rapidly increasing the knowledge of the model. FIG. 14 shows a principal component analysis plot of the newly selected base polymers, as compared to the previously synthesized polymers.

Example 8: Preliminary Model Evaluation

Model Predictive Capacity

Figure 15:
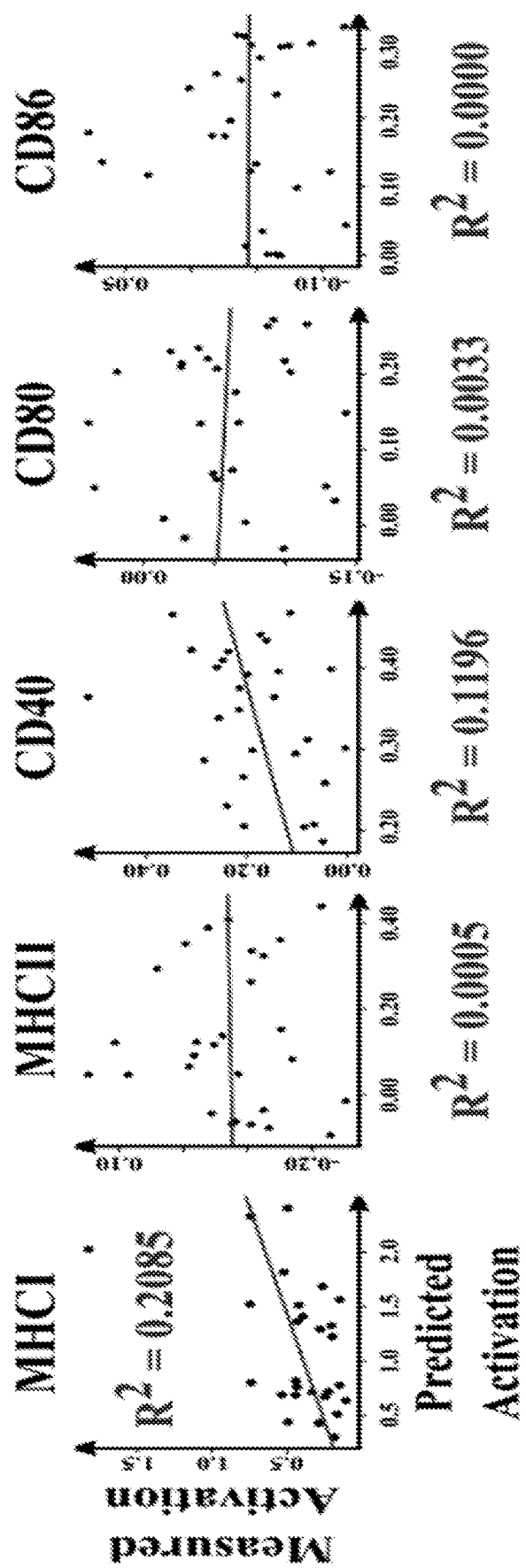
FIG. 15 is a series of plots comparing measured vs predicted activation for polymers selected using preliminary machine learning models.

The novel polymers were selected with maximum predictive uncertainty for model improvement, which meant that high predictive power was not to be expected. Nevertheless, to contextualize the predictive ability of the model on these test polymers, evaluation of the predictive capacity of preliminary machine learning models was performed. Predicted activation values were compared with measured activation values for the selected polymers. FIG. 15 provides this comparison for each QSPR model.

Figure 16:
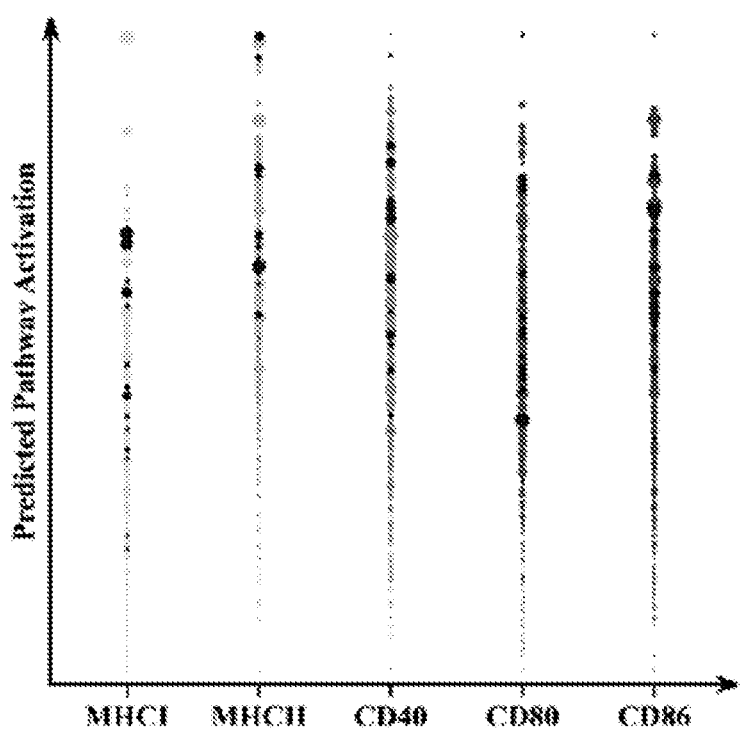
FIG. 16 shows a distribution of the predicted immunomodulatory properties of polymers. Polymers selected for synthesis are dark. Sizes show uncertainty of prediction.

With respect to these predictions, both of the preliminary MHCI and CD40 models show the expected limited predictability with low $R^2$ values. Further, the preliminary MHCII, CD80 and CD86 models did not appear to be predictive, with $R^2$ values close to zero, indicating that low confidence predictions are even less tractable for these specific pathways. These observations contrast with previous evaluation, whereas all models exhibited $R^2$ values between 0.4-0.8. This discrepancy between model goodness-of-fit likely arises due to the high predictive uncertainty of the selected polymers. Further, the polymer selection mechanism (maximizing immune activation and prediction variance) led to the selection of polymers with predicted activation values that were close to the mean expected activation. FIG. 16 shows how the predicted activation values of the selected polymers are distributed relative to the predicted activation values of all polymers.

Across all pathways, the selection of polymers is biased toward average activation values. This is particularly pronounced in the MHCI, CD80 and CD86 pathways. Whilst this close-to-average selection appears to have been less problematic in the case of activation pathways with large values over the negative control (MHCI and CD40), it may explain poor model performance for the other pathways. This is because the selected polymers exhibit activation values which are closer to the background noise of the screen (negative control) and are thus more difficult to accurately predict, leading to poor model performance. Table 4 shows the differences in maximum polymer activation across each of the performed biological screens. Screens 1 and 2 consist of polymers selected according to commercial availability. Screen 3 consists of polymers selected according to diversity selection, and screen 4 consists of polymers selected using the guidance of the QSPR model. Whilst MHCI and CD40 maximum activation values are similar across all screens, MHCII, CD80 and CD86 values vary greatly, potentially highlighting the impact of background noise upon the measurement of these markers.

TABLE 4

| Screen | MHCI | MHCII | CD40 | CD80 | CD86 |
|---|---|---|---|---|---|
| 1 | 3.24 | 0.62 | 0.58 | 0.41 | 0.51 |
| 2 | 1.89 | 0.13 | 0.47 | 0.08 | 0.08 |
| 3 | 2.55 | 0.40 | 0.76 | 0.52 | 0.45 |
| 4 | 1.82 | 0.15 | 0.51 | 0.04 | 0.08 |

While low pathway activation values from polymers in Screen 2 was expected, it was surprising to observe low activation values for polymers selected using the constructed QSPR model. It was hypothesized that the numerical representation was not accurate yet. As multiple representations of the polymers had already been explored, it was assumed that the representation of the biological data might adversely impact model predictability. Consequently, the manner in which biological data was represented was considered with respect to its potential contribution to the poor ability of the model to predict MHCII, CD80, and CD86 activation.

Biological Data Representations

In previous screens, all immune activation data was converted to a Polymer Score (% activation of positive control) according to equation (I):

$$\frac{[\% \text{ activated cells}]_{polymer} - [\% \text{ activated cells}]_{antigen}}{[\% \text{ activated cells}]_{LPS} - [\% \text{ activated cells}]_{antigen}} \quad (I)$$

The Polymer Score is a value between 0-1 which represented the normalized pathway activation. This scoring function allowed for the aggregation and comparison of data between different biological screens, each with different positive and negative control values. Normalization was achieved by subtracting the negative control and representing activation as a function of the positive control.

This normalization method required the assumption that the positive control (lipopolysaccharide) represented maximum activation across all pathways. However, in previous polymer screen data, several polymers achieved greater than 3-fold activation over lipopolysaccharide for the MHCI pathway, thereby calling into question the utility of lipopolysaccharide as an appropriate positive control for each of the immune pathways.

Figure 17:
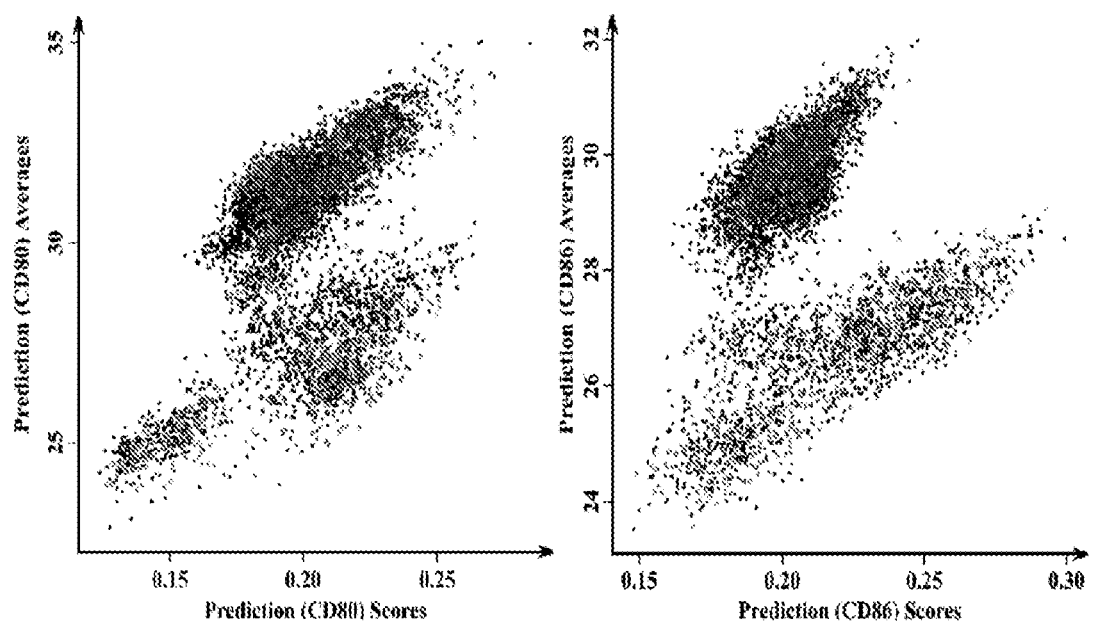
FIG. 17 shows plots illustrating the predicted averages vs scores for the top 10% of polymers in the CD80 and CD86 models. Screen 1 is shown in light dots; screen 2 is shown in dark dots; and screen 3 is shown in medium-colored dots.

To evaluate the use of the Polymer Score as a normalized representation of pathway activation, additional machine learning models the for CD80 and CD86 pathways were constructed using data from screens 1-3. These model were constructed using activation data which was not normalized between screens. Using these models, the activation of the top 10% of polymers was predicted. This allowed for the evaluation of differences between predictions made with normalized vs unnormalized data. FIG. 17 shows the predictions of the top 10% of polymers for the CD80 and CD86 pathways, alongside the screen which each prediction is based upon.

Figure 18:
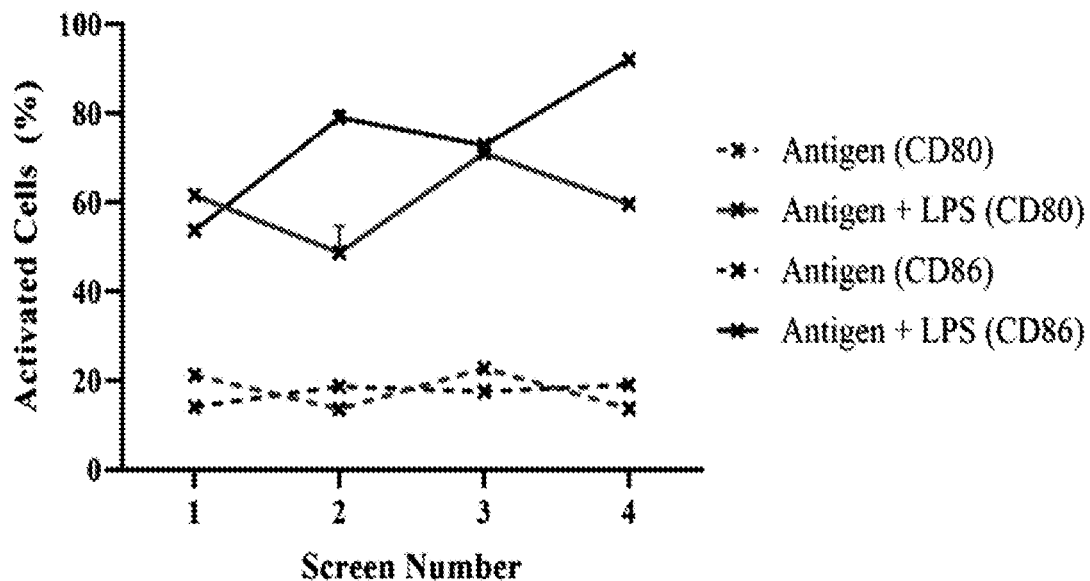
FIG. 18 is a plot showing the comparison of cell activation values for positive and negative controls for CD80 and CD86.

The CD80 and CD86 predictions are grouped into two distinct clusters; this indicates a consistent numerical discrepancy between the predicted values. Furthermore, each cluster contains polymers with high structural similarity to one (or two) of the three in vitro screens. This provides an indication of which polymer from the training data and from which screen the prediction was based upon. The upper cluster contains polymers which exhibit high structural similarity to polymers in screens 1 & 3, whilst the lower cluster contains polymers similar to those in screens 1 & 2. Therefore, it appears that clustering occurs due to numerical differences between the different screens, particularly screen 1 vs. screen 3. Comparison of experimental activation values reveals notable differences in the activation values for the activation values of the negative (antigen alone) and positive (antigen+lipopolysaccharide) controls during these screens. This is shown in FIG. 18.

Greater variation is observed in cell activation values with the positive control (Antigen+LPS), over the negative control (Antigen alone). This variation, combined with the poor utility of LPS in determining maximum cell activation, prompted a search for alternative metrics to represent the biological data. The utility of two metrics, represented by equation (II) (absolute activation):

$$[\% \text{ activated cells}]_{polymer} - [\% \text{ activated cells}]_{antigen} \quad (II)$$

and by equation (III) (relative activation):

$$\frac{[\% \text{ activated cells}]_{polymer}}{[\% \text{ activated cells}]_{antigen}} \quad \text{(III)}$$

were evaluated. Both of these metrics avoid LPS activation as a variable.

These data representations were used to construct further machine learning models, using data from screens 1-3. The immunomodulatory properties for the polymers in screen 4 were then predicted. This allowed us to compare model goodness-of-fit between the different biological data metrics. The evaluation was based on CD40 activation, owing to the previous moderate predictability of this model using Polymer Scores.

Figure 19:
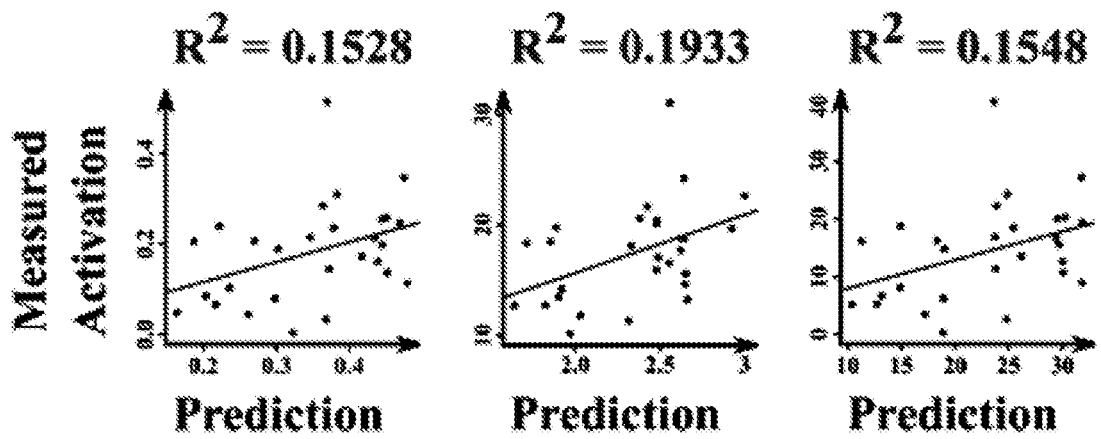
FIG. 19 is a series of plots depicting measured vs predicted activation of CD40. Three machine learning models were constructed using different representations of biological data represented by the metrics of equation (I) (left), equation (III) (middle), and equation (II) (right). These models were used to predict the activity of polymers screened during screen 4.

As evidenced by FIG. 19, the use of the metric described by equation (III) offers an improvement in model goodness-of-fit over the previous utilized Polymer Scores. Use of the metric described by equation (II) leads to similar goodness-of-fit to Polymer Scores. Consequently, the metric of equation (III) was utilized in future model evaluations, and to identify promising CD80 and CD86 pathway activators for a future screen.

Model Feature Importance and Active Learning

Figure 20:
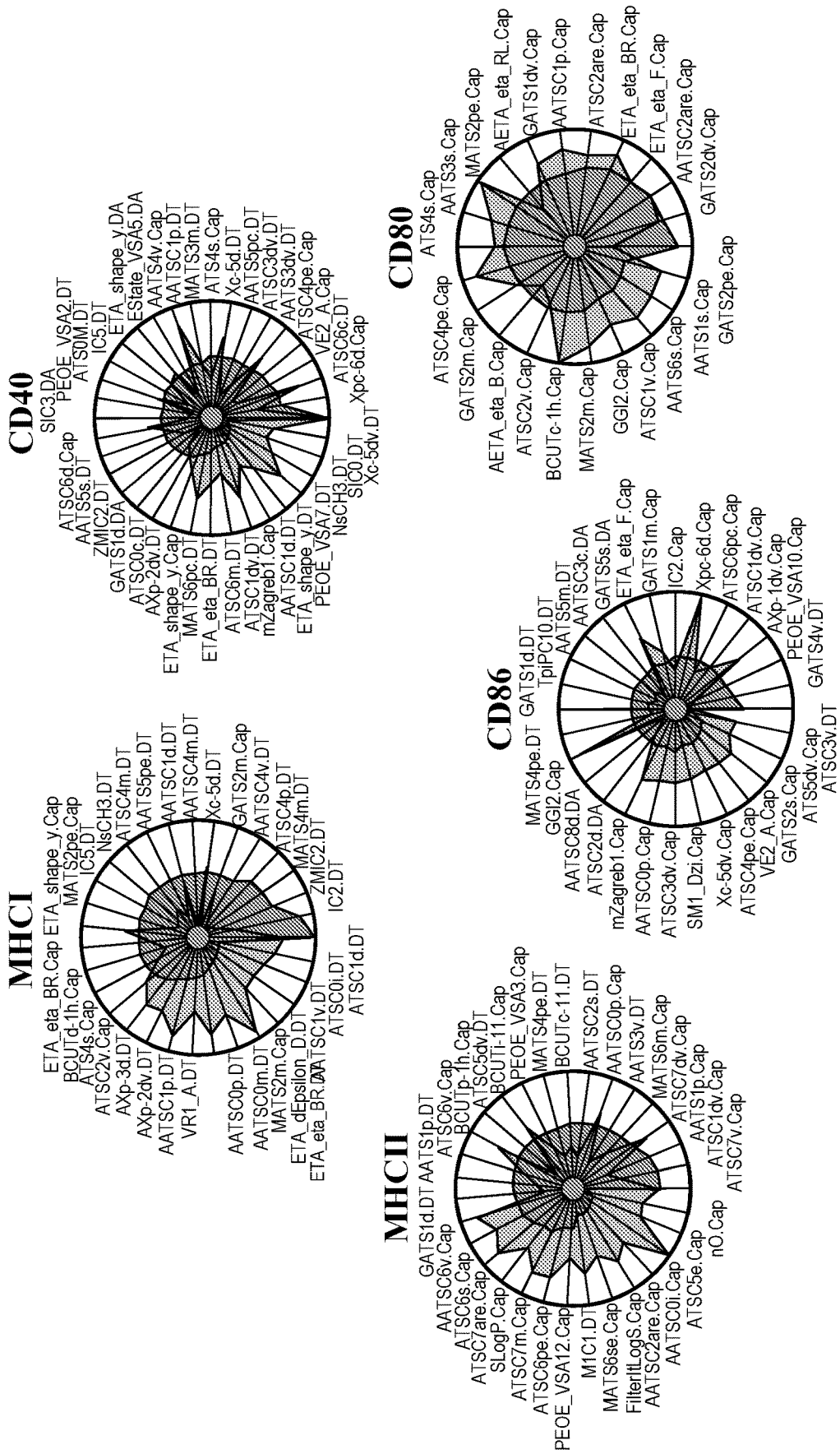
FIG. 20 is a series of radar plots showing random forest model feature importance. Features were extracted from the machine learning models for each immune pathway.

To evaluate whether the active learning approach successfully improved model performance, the random forest feature importance was calculated across the two model iterations. Feature importance is a fractional value of attribute importance, which are molecular descriptors in the models. Therefore, if a model is successful in explaining the underlying SAR, one would expect the most important features to remain consistent, potentially with increasing descriptor importance. Conversely, if a model does not explain the underlying SAR, one would expect descriptor importance to change between model iterations. FIG. 20 shows radar plots of the most important descriptors across the different model iterations.

Across all of the pathways, notable changes in feature importance were observed. This is particularly true in the case of the MHCI model, whereas the second model deprioritizes many of the features which were important in the preliminary model. This occurs alongside a concomitant increase in new features. Regardless, several features remain important between the two models. A similar pattern of changing feature importance is observed in the CD40, MHCII, and CD86 models. The CD80 model features appear to be the most consistent between the two model iterations. Importantly, the descriptors which have the highest feature importance in the second screen also exhibit high feature importance in the first model. This is true of the MHCI, CD40 and MHCII models, conversely, the CD86 and CD80 models exhibit changes of the most important descriptor. Together, these observations suggest that the employed active learning strategy served to enhance the ability of the model to explain the underlying SAR.

Regarding occurrence of molecular descriptors between the different activation pathways, dithiol and cap descriptors appear approximately equally weighted between the pathways, with few diacrylate features occurring. This is particularly true in the MHCI and MHCII descriptors, where no diacrylate descriptors are featured. Interestingly, the CD80 model exhibits only cap descriptors. Together, these observations suggest that each of the polymer building blocks has differential importance in determining immune pathway activation. In terms of descriptor interpretation, topological descriptors (autocorrelation (ATCS . . . , GATS . . . ) and others (ETA, Chi indices (Xp . . . , Xc . . . )), which have limited interpretability in terms of simple physiochemical properties predominated. This is because topological descriptors are calculated upon graphical representations of the molecules (matrices) using algebraic operators.

To assess whether the changes in descriptor importance corresponded to altered polymer activity predictions, the activation values of the top 100 polymers for each immune pathway were predicted with each model iteration.

Figure 21:
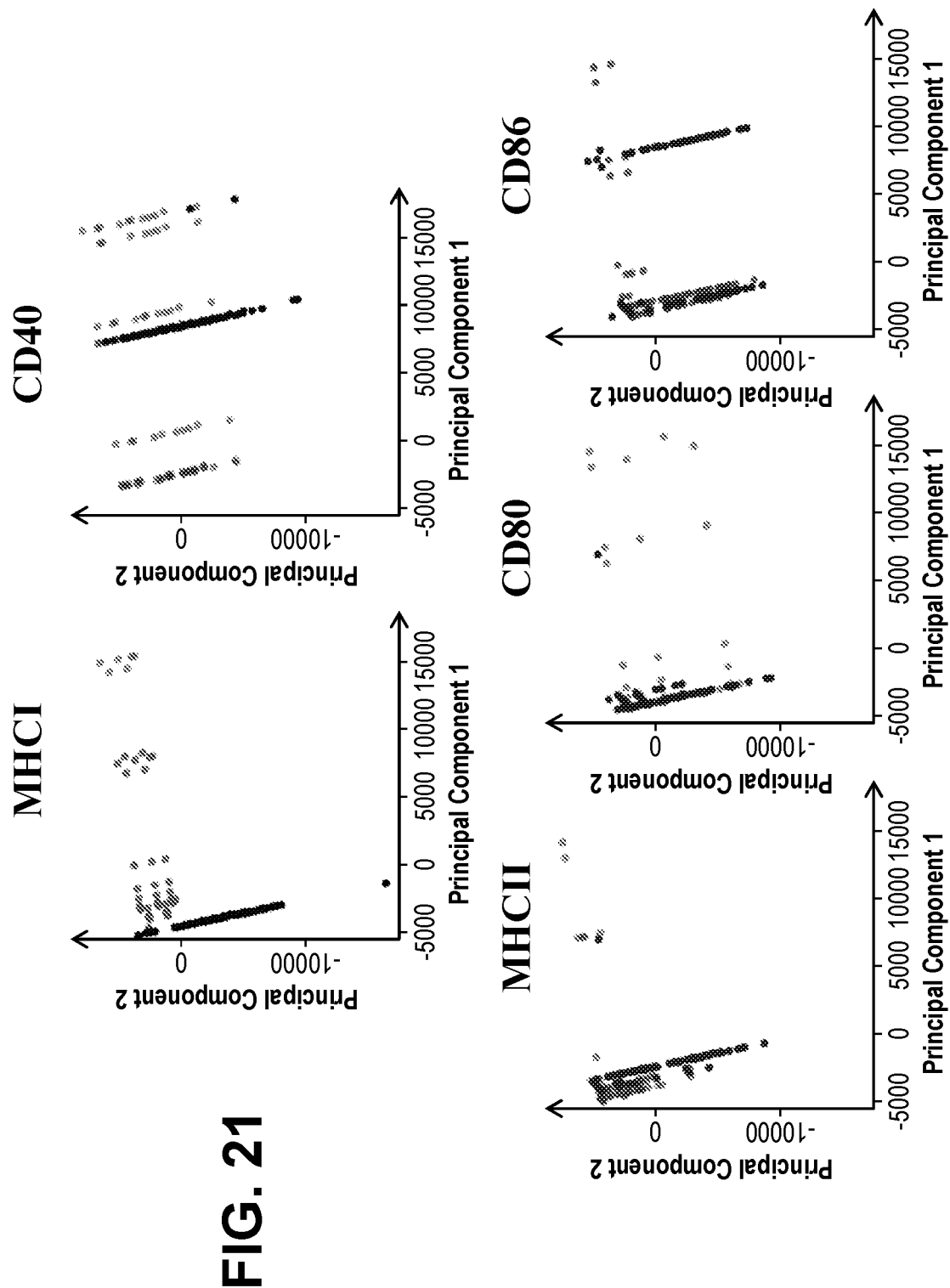
FIG. 21 is a series of plots displaying principal component analysis of the position of the top 100 predicted polymers from two model iterations. Later model iterations are shown by darker colored dots. The feature space was generated as the first two principal components of the molecular descriptors.

As illustrated in FIG. 21, across each of the activation pathways, the initial model predictions occurred in 3-4 clusters, with very different molecular descriptors. Conversely, the second iteration of the models predict a single linear cluster of polymers, aside from the two clusters which are observed in the CD86 predictions. The linear nature of the clusters likely arises due to the presence of highly correlated principal components, which are molecular descriptors. Together, these observations suggest that the promising regions of chemical space identified by the machine learning model are increasingly defined in the second model, with several previous regions of interest being invalidated.

Evaluation of Final QSPR Model and Computational Workflow

Final Model Evaluation

Figure 22:
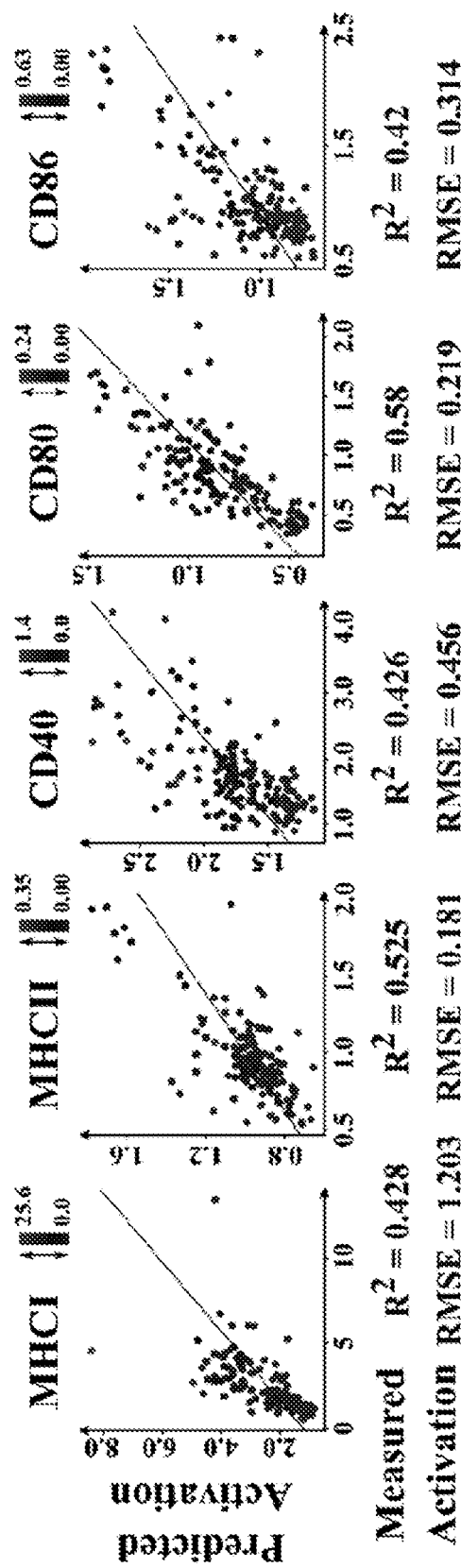
FIG. 22 is a series of plots illustrating the performance of final machine learning models.

To evaluate the ability of the QSPR model to identify promising activators of each immune pathway, models were constructed using all data from previous screens. These models were subject to 10-fold stratified cross validation, allowing for the evaluation of model performance. FIG. 22 shows the performance of each model, alongside associated $R^2$ and Root Mean Square Error (RMSE) values.

$R^2$ values remain relatively consistent between models, with the MHCII and CD80 models exhibiting the highest values. RMSE values vary to greater degree, with the MHCI model being highest, followed by the other models which have notably lower values. The predominant reason for this large difference in RMSE is due to the range of MHCI activation values, which are approximately 4-fold larger than the other pathways. Consequently, it is only appropriate to compare RMSE values between models with similar activation ranges (CD40, CD80, CD86 and MHCII). This comparison shows the highest RMSE in the CD40 model, followed by CD86 and CD80. This evaluation of model goodness-of-fit matches corresponds with visual evaluation of the data, whereas a more scattered correlation in the CD40 and CD86 models was observed. Interestingly, all models exhibit excellent goodness-of-fit at lower activation values, observed as linear clusters close to the graph origin. By progress to higher activation values, much greater deviation occurred, alongside an increase in predictive uncertainty. This indicates that whilst the models are effective at predicting polymers with lower activation values, their ability to accurately predict polymers with higher activation values is limited. Regardless, it is clear that these models are able to identify polymers of interest, which have high likelihood of above average activation values. Consequently, the constructed machine learning models appear to be useful tools in expediting the screening of the polymer chemical space, allowing for the identification of polymers with desired immunomodulatory properties.

Figure 23:
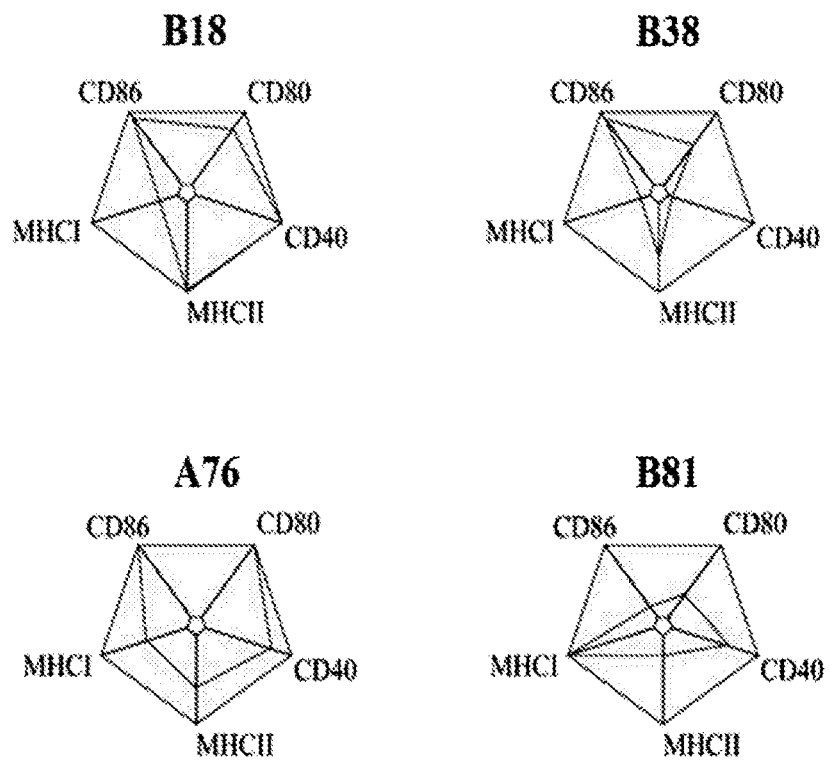
FIG. 23 is series of radar plots presenting screening data for four synthesized polymers using the metric defined in equation (III). Maximum values on plot are defined by maximum activations.

Each of the polymers screened appears to have a unique and independent capacity to activate each of the immune pathways, as depicted in FIG. 23. Generally, these polymers can be grouped into MHCI, MHCII/CD80/CD86 and CD40 activators. The correlations observed between MHCII/

Figure 24:
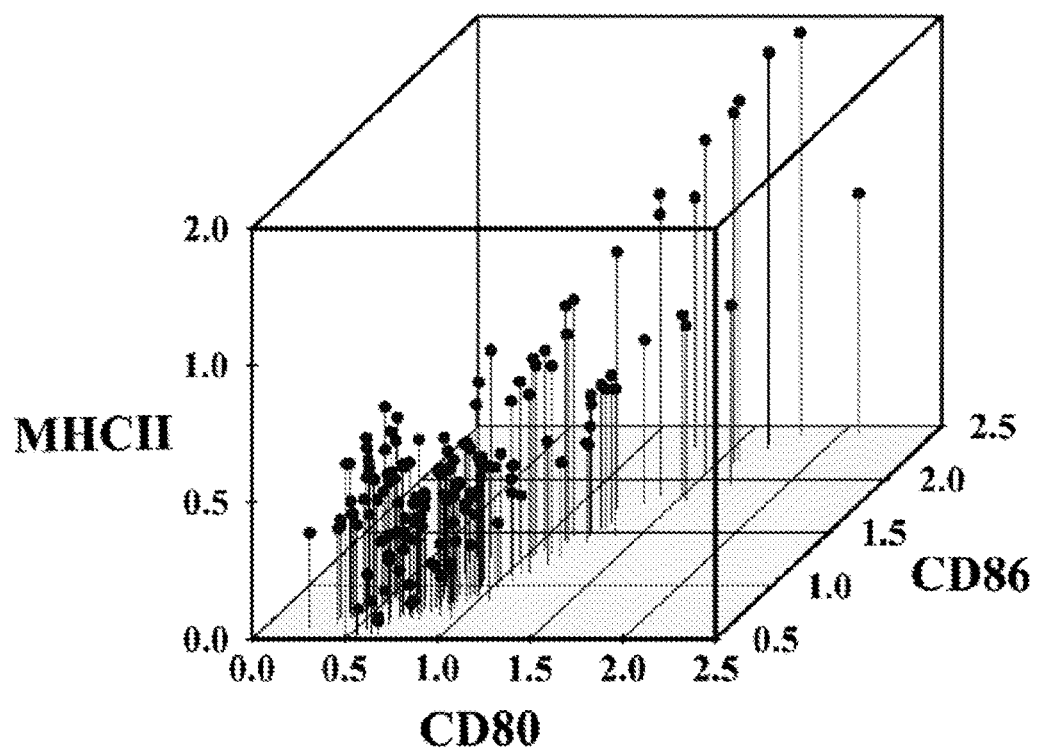
FIG. 24 is a 3D scatterplot of the MHCII, CD80, and CD86 activation values of screened polymers.

CD80/CD86 activation are also found to be persistent in the whole dataset, potentially indicating a mutual mechanism of marker upregulation. FIG. 24 shows the relationship between the activation values of these pathways.

Utility of Computational Workflow and QSPR Model

Figure 25:
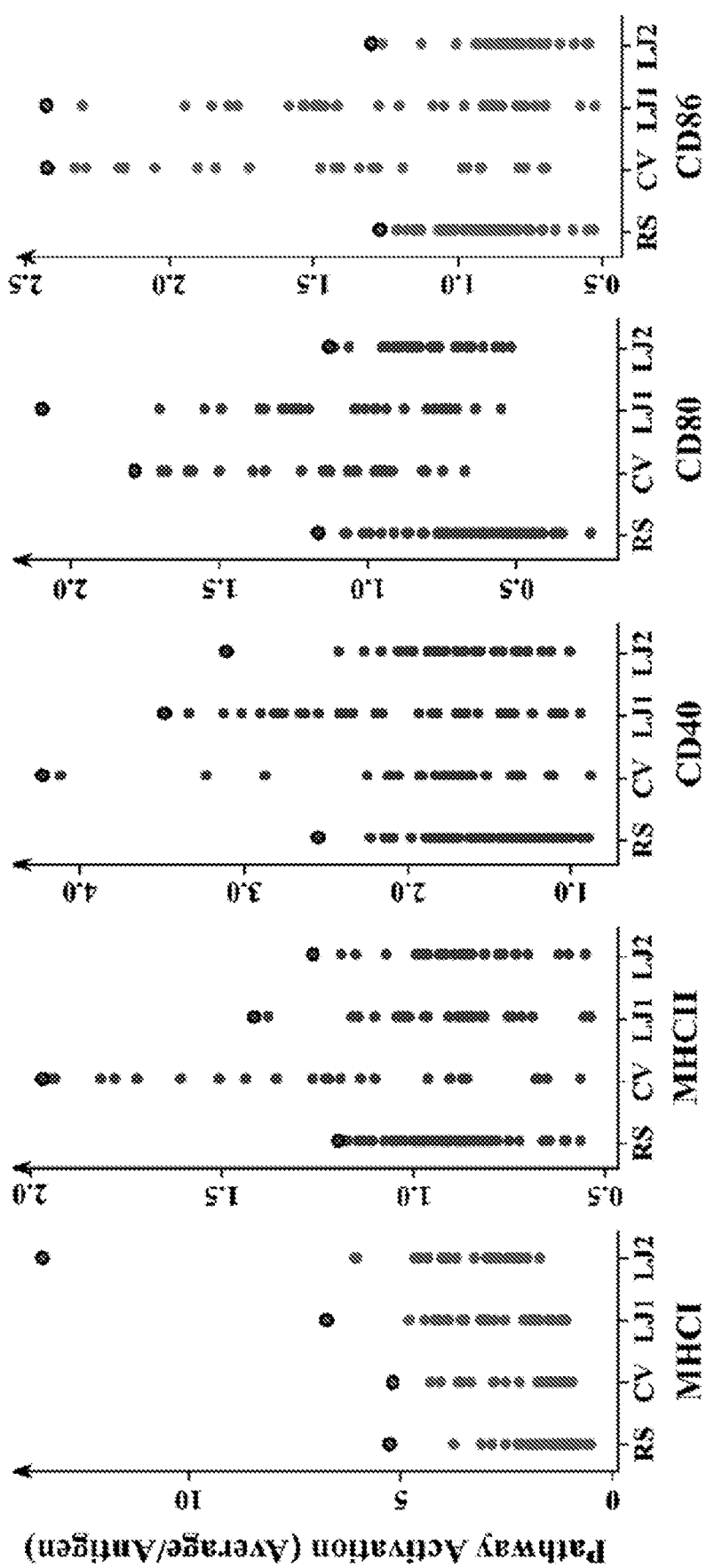
FIG. 25 is a series of graphs showing pathway activation across different polymer series.

To assess the utility of the computational workflow in identifying polymers with high immunomodulatory properties, a comparison of the maximum activation values achieved from each of the polymer series was performed. A comparison of commercially valuable (CV and RS), diversity selected (LJ1), and model selected (LJ2) activation values is shown in FIG. 25. Pathway activation was evaluated using the metric described in equation (III).

In the case of MHCI, the use of a computational workflow has facilitated the identification of polymers with increasing activation values (this observation is particularly true when transitioning from the RS, CV and LJ1 polymers to LJ2, wherein a large increase in maximal activation was noted). Surprisingly, in the case of MHCII, CD40 and CD86, a notable benefit in employing the computational workflow to identify activating polymers was not yet observed. Conversely, the CV (commercially available polymers, end-capped) achieve the greatest range of activation values. With respect to CD80 activation, the LJ1 polymers (diversity selected) achieve an increase in maximal activation, while the LJ2 (model selected) polymers exhibit a decrease.

Figure 26:
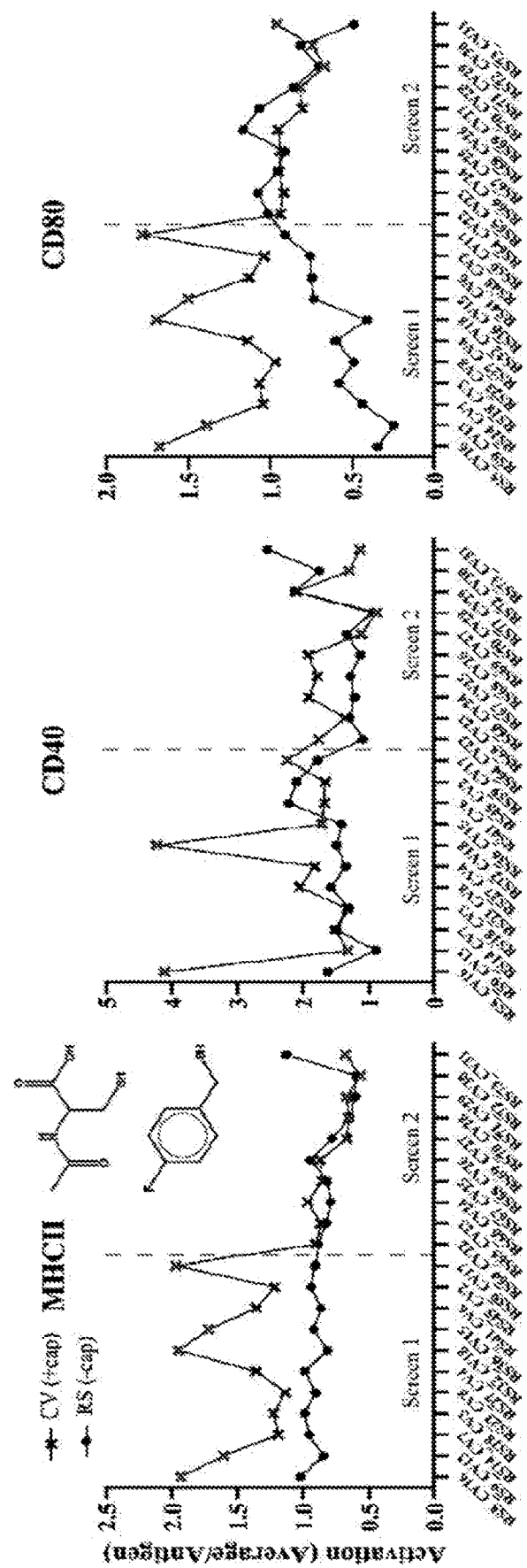
FIG. 26 is a series of graphs showing the impact of end-capping on dendritic cell activation. Polymers incorporating (CV) and excluding (RS) end-caps were screened for dendritic cell activation. Two end-caps were used: N-acetyl cysteine (dark Xs) and 4-fluorobenzyl mercaptan (light Xs). Data was aggregated across two different screens (line).

The high activation values of the CV polymers are surprising, particularly as the CV and RS polymers utilize the same base polymers, with only the incorporation of end-caps distinguishing the polymers. FIG. 26 compares the activation values of capped (CV) and uncapped (RS) polymers across two screens.

Polymer end-capping appears to greatly influence pathway activation. This modification appears to be dependent upon the end-cap structure, as higher activation values were observed from polymers capped with N-acetyl cysteine (NAC) over 4-fluorobenzyl mercaptan (FBM). Further, the impact of end-capping appears to be context dependent; this is observed across CD40 activation whereas capping with NAC does not always result in pathway marker upregulation. Interestingly, across the two screens, variance in the degree of pathway upregulation from NAC capping was observed. Specifically, in the first screen we observe greater marker upregulation from NAC capping. These differences may again indicate the context dependent nature of end-capping on marker expression, or it may highlight the (biological) degeneracy between screens.

In conclusion, the utility of the computational workflow appears most promising in the case of MHCI, as an increase in maximal pathway activation in MHCI, both in polymers selected using diversity selection and the QSPR model was achieved. A similar increase in pathway activation was not observed for the other pathways, though further screenings are expected to improve model performance.

Example 9: Validation of Polymeric Adjuvant B18 in a Mouse Model

Figure 27:
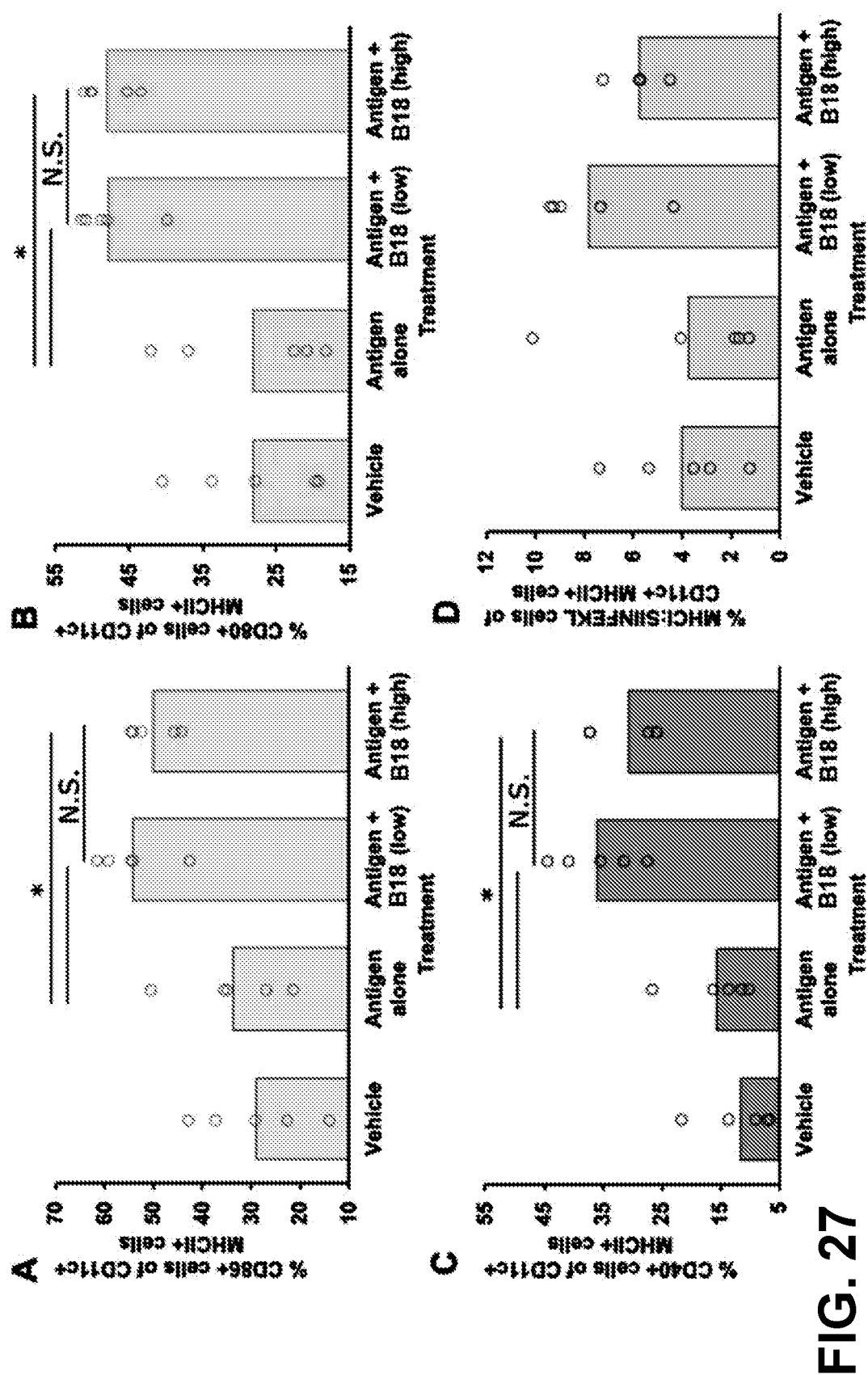
FIG. 27 is a series of graphs showing the expression of CD86 (FIG. 27A), CD80 (FIG. 27B), CD40 (FIG. 27C), and MHCI: SIINFEKL (FIG. 27D) on dendritic cells in a mouse model following administration of a low or high dose of B18-based polymer adjuvant mixed with antigen or administration of antigen alone.

The activity of the polymeric adjuvant B18 was assessed in C57BL/6J mice. Vaccines were prepared by admixing a model peptide antigen (SIINFEKL) with B18 nanoparticles and injected subcutaneously into mice. Following three injections placed three days apart, animals were sacrificed and dendritic cell phenotype in the draining lymph nodes were analyzed using flow cytometry. Treatment with antigen alone led to no appreciable dendritic cell activation as compared to vehicle-treated animals. Notably, B18-based vaccines led to a significant upregulation of activation markers (CD86, CD80, and CD40) as compared to antigen treated animals (*p<0.05, One-way ANOVA, post-hoc Bonferroni), see FIG. 27A-C. Moreover, there was an increase in cross-presentation of the antigen when delivered using B18-based vaccines; however, the cross-presentation did not reach statistical significance (FIG. 27D).

Figure 28:
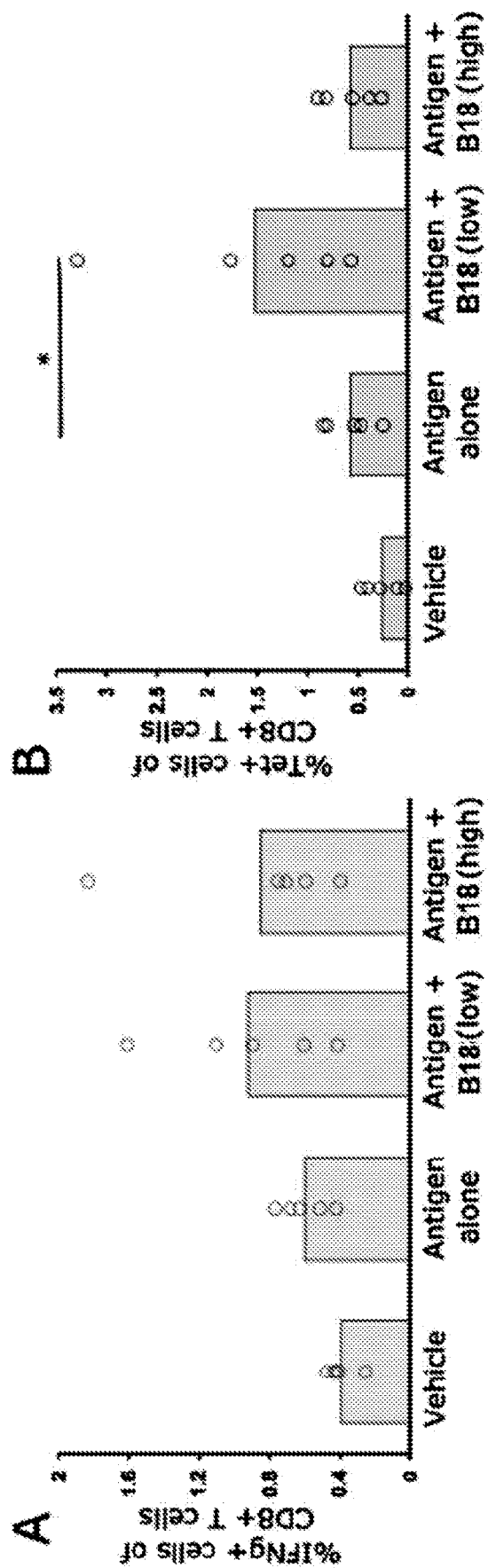
FIG. 28 is a set of graphs showing the levels of interferon γ (INF-γ) (FIG. 28A) and antigen-specific CD8+ T cells (FIG. 28B) in mice that were administered antigen alone or antigen combined with a high or low dose of the polymeric adjuvant B18.

The ability of B18 to increase the anti-tumor cytokine interferon-γ (INF-γ) in splenic CD8+ T cells was also assessed along with the adjuvant's ability to increase the fraction of CD8+ T cells specific to the antigen SIINFEKL. Mice were treated with vehicle control, antigen alone, or antigen combined with a high and low dose of the polymeric adjuvant B18. Mice were then challenged with the antigen prior to sacrifice. Levels of interferon-g (IFN-g) and antigen-specific CD8+ T cells were measured using flow cytometry (*p<0.05, One-way ANOVA, post-hoc Bonferroni). As shown in FIG. 28, treatment with a B18-based vaccine led to an increase in both IFN-g and the fraction of antigen-specific CD8+ T cells.

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

The invention claimed is:

1. A method of modulating the immune system, comprising administering to a subject a polymer of Formula (I):

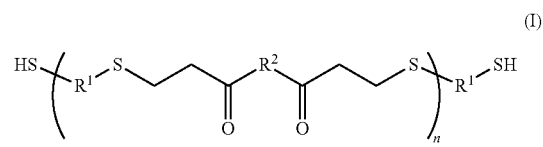

(I)

or a pharmaceutically acceptable salt thereof, wherein,
R$^1$ is

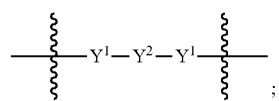

;

Y$^1$ is C$_{1-3}$ alkyl, (C$_{1-6}$ alkyl)-NHC(═O), C═O, 5 to 10-membered heteroaryl, or absent, wherein heteroaryl is optionally substituted, independently for each occurrence, one, two, or three times with C$_{1-3}$ alkyl, C$_{1-3}$ alkoxy, C$_{1-3}$ haloalkyl, halogen, or 6 to 10-membered aryl;

Y$^2$ is C$_{1-6}$ alkyl, 6 to 10-membered aryl, biphenyl, 5 to 10-membered heteroaryl, (CH$_2$CH$_2$O)$_p$CH$_2$CH$_2$, C═N—(C$_{1-6}$ alkyl)-N═C, O, S, or SO$_2$, wherein the alkyl, aryl, biphenyl, and heteroaryl are optionally substituted, independently for each occurrence, one, two, or three times with $C_{1-6}$ alkyl, $C_{1-6}$ alkoxy, $C_{1-6}$ haloalkyl, $(C_{0-3}$ alkyl)-OH, $NH_2$, $NH(C_{1-6}$ alkyl), $N(C_{1-6}$ alkyl)$_2$, halogen, or carboxylic acid;

$R^2$ is $C_{1-6}$ alkyl, 6 to 10-membered aryl, O, or

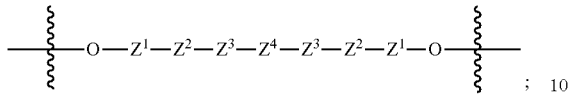

$Z^1$ is $C_{1-6}$ alkyl or 6 to 10-membered aryl;

$Z^2$ is O, $O(C=O)O$, or absent;

$Z^3$ is 6 to 10-membered aryl, 5 to 10-membered heteroaryl, or absent;

$Z^4$ is $C_{1-6}$ alkyl, 5 to 15-membered cycloalkyl, 5 to 15-membered heterocyclyl, 6 to 14-membered aryl, 5 to 15-membered heteroaryl, or $(C=O)O$-(6 to 10-membered aryl)-$O(C=O)$, each of which are optionally substituted, independently for each occurrence, one, two, or three times with $C_{1-3}$ alkyl, $C_{1-3}$ haloalkyl, or halogen;

n is 25-250;

p is 1, 2, 3, or 4; and wherein $R^1$, $R^2$, $Y^1$, $Y^2$, $Z^1$, $Z^2$, $Z^3$, and $Z^4$ are each, independently, the same for every occurrence in the polymer.

2. A method of inducing the expression of CD86, CD80, and/or CD40 in a subject in need thereof, the method comprising administering to the subject a polymer of Formula (I):

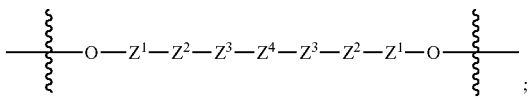

or a pharmaceutically acceptable salt thereof, wherein, $R^1$ is

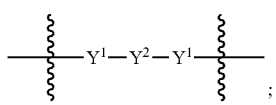

$Y^1$ is $C_{1-3}$ alkyl, $(C_{1-6}$ alkyl)-$NHC(=O)$, $C=O$, 5 to 10-membered heteroaryl, or absent, wherein heteroaryl is optionally substituted, independently for each occurrence, one, two, or three times with $C_{1-3}$ alkyl, $C_{1-3}$ alkoxy, $C_{1-3}$ haloalkyl, halogen, or 6 to 10-membered aryl;

$Y^2$ is $C_{1-6}$ alkyl, 6 to 10-membered aryl, biphenyl, 5 to 10-membered heteroaryl, $(CH_2CH_2O)_pCH_2CH_2$, $C=N-(C_{1-6}$ alkyl)-$N=C$, O, S, or $SO_2$, wherein the alkyl, aryl, biphenyl, and heteroaryl are optionally substituted, independently for each occurrence, one, two, or three times with $C_{1-6}$ alkyl, $C_{1-6}$ alkoxy, $C_{1-6}$ haloalkyl, $(C_{0-3}$ alkyl)-OH, $NH_2$, $NH(C_{1-6}$ alkyl), $N(C_{1-6}$ alkyl)$_2$, halogen, or carboxylic acid;

$R^2$ is $C_{1-6}$ alkyl, 6 to 10-membered aryl, O, or

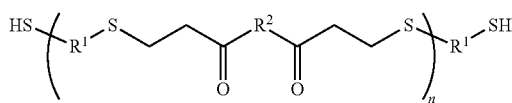

$Z^1$ is $C_{1-6}$ alkyl or 6 to 10-membered aryl;

$Z^2$ is O, $O(C=O)O$, or absent;

$Z^3$ is 6 to 10-membered aryl, 5 to 10-membered heteroaryl, or absent;

$Z^4$ is $C_{1-6}$ alkyl, 5 to 15-membered cycloalkyl, 5 to 15-membered heterocyclyl, 6 to 14-membered aryl, 5 to 15-membered heteroaryl, or $(C=O)O$-(6 to 10-membered aryl)-$O(C=O)$, each of which are optionally substituted, independently for each occurrence one, two, or three times with $C_{1-3}$ alkyl, $C_{1-3}$ haloalkyl, or halogen;

n is 25-250;

p is 1, 2, 3, or 4; and wherein $R^1$, $R^2$, $Y^1$, $Y^2$, $Z^1$, $Z^2$, $Z^3$, and $Z^4$ are each, independently, the same for every occurrence in the polymer.

3. A method of increasing the levels of interferon-γ in a subject in need thereof, the method comprising administering to the subject a polymer of Formula (I):

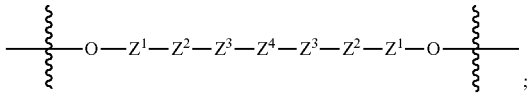

or a pharmaceutically acceptable salt thereof, wherein, $R^1$ is

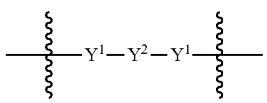

$Y^1$ is $C_{1-3}$ alkyl, $(C_{1-6}$ alkyl)-$NHC(=O)$, $C=O$, 5 to 10-membered heteroaryl, or absent, wherein heteroaryl is optionally substituted, independently for each occurrence, one, two, or three times with $C_{1-3}$ alkyl, $C_{1-3}$ alkoxy, $C_{1-3}$ haloalkyl, halogen, or 6 to 10-membered aryl;

$Y^2$ is $C_{1-6}$ alkyl, 6 to 10-membered aryl, biphenyl, 5 to 10-membered heteroaryl, $(CH_2CH_2O)_pCH_2CH_2$, $C=N-(C_{1-6}$ alkyl)-$N=C$, O, S, or $SO_2$, wherein the alkyl, aryl, biphenyl, and heteroaryl are optionally substituted, independently for each occurrence, one, two, or three times with $C_{1-6}$ alkyl, $C_{1-6}$ alkoxy, $C_{1-6}$ haloalkyl, $(C_{0-3}$ alkyl)-OH, $NH_2$, $NH(C_{1-6}$ alkyl), $N(C_{1-6}$ alkyl)$_2$, halogen, or carboxylic acid;

$R^2$ is $C_{1-6}$ alkyl, 6 to 10-membered aryl, O, or $Z^1$ is $C_{1-6}$ alkyl or 6 to 10-membered aryl;

$Z^2$ is O, O(C=O)O, or absent;

$Z^3$ is 6 to 10-membered aryl, 5 to 10-membered heteroaryl, or absent;

$Z^4$ is $C_{1-6}$ alkyl, 5 to 15-membered cycloalkyl, 5 to 15-membered heterocyclyl, 6 to 14-membered aryl, 5 to 15-membered heteroaryl, or (C=O)O-(6 to 10-membered aryl)-O(C=O), each of which are optionally substituted, independently for each occurrence, one, two, or three times with $C_{1-3}$ alkyl, $C_{1-3}$ haloalkyl, or halogen;

n is 25-250;

p is 1, 2, 3, or 4; and wherein $R^1$, $R^2$, $Y^1$, $Y^2$, $Z^1$, $Z^2$, $Z^3$, and $Z^4$ are each, independently, the same for every occurrence in the polymer.

* * * * *